(12) United States Patent
Nankervis

(10) Patent No.: US 11,795,432 B2
(45) Date of Patent: *Oct. 24, 2023

(54) PASSIVE REPLACEMENT OF MEDIA

(71) Applicant: Terumo BCT, Inc., Lakewood, CO (US)

(72) Inventor: Brian J. Nankervis, Golden, CO (US)

(73) Assignee: Terumo BCT, Inc., Lakewood, CO (US)

(*) Notice: Subject to any disclaimer, the term of this patent is extended or adjusted under 35 U.S.C. 154(b) by 715 days.

This patent is subject to a terminal disclaimer.

(21) Appl. No.: 15/849,309

(22) Filed: Dec. 20, 2017

(65) Prior Publication Data

US 2018/0119094 A1 May 3, 2018

Related U.S. Application Data

(62) Division of application No. 14/668,659, filed on Mar. 25, 2015, now Pat. No. 11,008,547.

(Continued)

(51) Int. Cl.
*C12N 5/071* (2010.01)
*C12M 1/34* (2006.01)
(Continued)

(52) U.S. Cl.
CPC ........... *C12N 5/0602* (2013.01); *C12M 25/10* (2013.01); *C12M 29/00* (2013.01); *C12M 29/16* (2013.01);
(Continued)

(58) Field of Classification Search
None
See application file for complete search history.

(56) References Cited

U.S. PATENT DOCUMENTS 2,997,077 A  8/1961  Rodrigues
3,013,435 A  12/1961  Rodrigues
(Continued)

FOREIGN PATENT DOCUMENTS

CA       1016332 A    8/1977
CN       102406926    4/2012
(Continued)

OTHER PUBLICATIONS

Communication pursuant to Article 94(3) EPC, European Patent Application No. 15718657.8, dated Jul. 21, 2017.
(Continued)

*Primary Examiner* — William H. Beisner
(74) *Attorney, Agent, or Firm* — Harness, Dickey & Pierce, P.L.C.

(57) ABSTRACT

Embodiments described herein generally relate to passively replacing media in a closed cell expansion system to reduce or prevent the dilution of chemical signaling used to inhibit signaling pathways that keep a cell population in the lag phase of cell growth. To prevent such dilution, active inlet fluid flow to the system may be halted. To replace fluid lost by the system, a bag containing media may be attached to the waste line in replacement of the waste or outlet bag connected thereto. By turning off one or more pumps, media from the replacement bag is added to the system at the rate of evaporation. Chemical signaling dilution may be prevented while conserving system resources. Enhancement of chemical signaling to reduce the lag phase of cell growth may further be accomplished by adding molecules, such as chemical-signaling proteins, from a direct source to the system.

20 Claims, 13 Drawing Sheets

Related U.S. Application Data

(60) Provisional application No. 61/970,274, filed on Mar. 25, 2014.

(51) Int. Cl.
*C12M 1/12* (2006.01)
*C12M 1/00* (2006.01)
*C12M 1/36* (2006.01)
*C12M 1/42* (2006.01)

(52) U.S. Cl.
CPC ............ *C12M 29/26* (2013.01); *C12M 35/08* (2013.01); *C12M 41/00* (2013.01); *C12M 41/48* (2013.01)

(56) References Cited

U.S. PATENT DOCUMENTS

| | | |
|---|---|---|
| 3,067,915 A | 12/1962 | Shapiro et al. |
| 3,191,807 A | 6/1965 | Rodrigues |
| 3,283,727 A | 11/1966 | Rodrigues |
| 3,701,717 A | 10/1972 | Ingvorsen |
| 3,821,087 A | 6/1974 | Knazek et al. |
| 3,896,061 A | 7/1975 | Tanzawa et al. |
| 4,173,415 A | 11/1979 | Wyatt |
| 4,301,010 A | 11/1981 | Eddleman et al. |
| 4,301,118 A | 11/1981 | Eddleman et al. |
| 4,391,912 A | 7/1983 | Yoshida et al. |
| 4,412,990 A | 11/1983 | Lundblad et al. |
| 4,418,691 A | 12/1983 | Yannas et al. |
| 4,439,322 A | 3/1984 | Sonoda et al. |
| 4,439,901 A | 4/1984 | Eddleman |
| 4,478,829 A | 10/1984 | Landaburu et al. |
| 4,486,188 A | 12/1984 | Altshuler et al. |
| 4,509,695 A | 4/1985 | Bessman |
| 4,585,654 A | 4/1986 | Landaburu et al. |
| 4,618,586 A | 10/1986 | Walker et al. |
| 4,629,686 A | 12/1986 | Gruenberg |
| 4,647,539 A | 3/1987 | Bach |
| 4,650,766 A | 3/1987 | Harm et al. |
| 4,670,544 A | 6/1987 | Schwinn et al. |
| 4,722,902 A | 2/1988 | Harm et al. |
| 4,727,059 A | 2/1988 | Binder et al. |
| 4,804,628 A | 2/1989 | Cracauer et al. |
| 4,828,706 A | 5/1989 | Eddleman |
| 4,885,087 A | 12/1989 | Kopf |
| 4,889,812 A | 12/1989 | Guinn et al. |
| 4,894,342 A | 1/1990 | Guinn et al. |
| 4,897,358 A | 1/1990 | Carrasco |
| 4,918,019 A | 4/1990 | Guinn |
| 4,960,521 A | 10/1990 | Keller |
| 4,973,558 A | 11/1990 | Wilson et al. |
| 4,988,623 A | 1/1991 | Schwarz et al. |
| 5,015,585 A | 5/1991 | Robinson |
| 5,019,054 A | 5/1991 | Clement et al. |
| 5,079,168 A | 1/1992 | Amiot |
| 5,126,238 A | 6/1992 | Gebhard et al. |
| 5,130,141 A | 7/1992 | Law et al. |
| 5,149,544 A | 9/1992 | Gentile et al. |
| 5,162,225 A | 11/1992 | Sager et al. |
| 5,169,930 A | 12/1992 | Ruoslahti et al. |
| 5,192,553 A | 3/1993 | Boyse et al. |
| 5,197,985 A | 3/1993 | Caplan et al. |
| 5,202,254 A | 4/1993 | Amiot |
| 5,225,346 A | 7/1993 | Matsumiya et al. |
| 5,226,914 A | 7/1993 | Caplan et al. |
| 5,240,614 A | 8/1993 | Ofsthun et al. |
| 5,240,861 A | 8/1993 | Bieri |
| 5,283,058 A | 2/1994 | Faustman |
| 5,310,676 A | 5/1994 | Johansson et al. |
| 5,324,428 A | 6/1994 | Flaherty |
| 5,330,915 A | 7/1994 | Wilson et al. |
| 5,342,752 A | 8/1994 | Platz et al. |
| 5,399,493 A | 3/1995 | Emerson et al. |
| 5,416,022 A | 5/1995 | Amiot |
| 5,422,197 A | 6/1995 | Zito |
| 5,436,151 A | 7/1995 | McGlave et al. |
| 5,437,994 A | 8/1995 | Emerson et al. |
| 5,439,757 A | 8/1995 | Zito |
| 5,459,069 A | 10/1995 | Palsson et al. |
| 5,460,964 A | 10/1995 | McGlave et al. |
| H1509 H | 12/1995 | Eran et al. |
| 5,478,739 A | 12/1995 | Slivka et al. |
| 5,486,359 A | 1/1996 | Caplan et al. |
| 5,496,659 A | 3/1996 | Zito |
| 5,507,949 A | 4/1996 | Ho |
| 5,510,257 A | 4/1996 | Sirkar et al. |
| 5,512,180 A | 4/1996 | Ho |
| 5,527,467 A | 6/1996 | Ofsthun et al. |
| 5,541,105 A | 7/1996 | Melink et al. |
| 5,543,316 A | 8/1996 | Zawadzka et al. |
| 5,545,492 A | 8/1996 | Zito |
| 5,549,674 A | 8/1996 | Humes et al. |
| 5,571,720 A | 11/1996 | Grandics et al. |
| 5,591,625 A | 1/1997 | Gerson et al. |
| 5,593,580 A | 1/1997 | Kopf |
| 5,595,909 A | 1/1997 | Hu et al. |
| 5,599,703 A | 2/1997 | Davis et al. |
| 5,605,822 A | 2/1997 | Emerson et al. |
| 5,605,829 A | 2/1997 | McGlave et al. |
| 5,605,835 A | 2/1997 | Hu et al. |
| 5,622,857 A | 4/1997 | Goffe |
| 5,626,731 A | 5/1997 | Cooley et al. |
| 5,627,070 A * | 5/1997 | Gruenberg ............. C12M 23/58 210/321.8 |
| 5,631,006 A | 5/1997 | Melink et al. |
| 5,635,386 A | 6/1997 | Palsson et al. |
| 5,635,387 A | 6/1997 | Fei et al. |
| 5,643,736 A | 7/1997 | Bruder et al. |
| 5,646,043 A | 7/1997 | Emerson et al. |
| 5,654,186 A | 8/1997 | Cerami et al. |
| 5,656,421 A | 8/1997 | Gebhard et al. |
| 5,658,995 A | 8/1997 | Kohn et al. |
| 5,667,985 A | 9/1997 | O'Leary et al. |
| 5,670,147 A | 9/1997 | Emerson et al. |
| 5,670,351 A | 9/1997 | Emerson et al. |
| 5,674,750 A | 10/1997 | Kraus et al. |
| 5,684,712 A | 11/1997 | Goffe et al. |
| 5,686,289 A | 11/1997 | Humes et al. |
| 5,688,687 A | 11/1997 | Palsson et al. |
| 5,695,989 A | 12/1997 | Kalamasz |
| 5,700,289 A | 12/1997 | Breitbart et al. |
| 5,705,534 A | 1/1998 | D'Agostino et al. |
| 5,707,859 A | 1/1998 | Miller et al. |
| 5,712,163 A | 1/1998 | Parenteau et al. |
| 5,728,581 A | 3/1998 | Schwartz et al. |
| 5,733,541 A | 3/1998 | Taichman et al. |
| 5,733,542 A | 3/1998 | Haynesworth et al. |
| 5,736,396 A | 4/1998 | Bruder et al. |
| 5,744,347 A | 4/1998 | Wagner et al. |
| 5,750,651 A | 5/1998 | Oppermann et al. |
| 5,753,506 A | 5/1998 | Johe |
| 5,763,194 A | 6/1998 | Slowiaczek et al. |
| 5,763,197 A | 6/1998 | Tsukamoto et al. |
| 5,763,261 A | 6/1998 | Gruenberg |
| 5,763,266 A | 6/1998 | Palsson et al. |
| 5,766,944 A | 6/1998 | Ruiz |
| 5,772,994 A | 6/1998 | Ildstad et al. |
| 5,783,075 A | 7/1998 | Eddleman et al. |
| 5,783,216 A | 7/1998 | Faustman |
| 5,785,912 A | 7/1998 | Cooley et al. |
| 5,804,446 A | 9/1998 | Cerami et al. |
| 5,806,529 A | 9/1998 | Reisner et al. |
| 5,807,686 A | 9/1998 | Wagner et al. |
| 5,811,094 A | 9/1998 | Caplan et al. |
| 5,811,397 A | 9/1998 | Francavilla et al. |
| 5,817,773 A | 10/1998 | Wilson et al. |
| 5,821,218 A | 10/1998 | Toback et al. |
| 5,827,735 A | 10/1998 | Young et al. |
| 5,827,740 A | 10/1998 | Pittenger |
| 5,830,921 A | 11/1998 | Cooley et al. |
| 5,833,979 A | 11/1998 | Schinstine et al. |
| 5,837,258 A | 11/1998 | Grotendorst |
| 5,837,539 A | 11/1998 | Caplan et al. |

(56) References Cited

U.S. PATENT DOCUMENTS

| | | |
|---|---|---|
| 5,840,502 A | 11/1998 | Van Vlasselaer |
| 5,840,576 A | 11/1998 | Schinstine et al. |
| 5,840,580 A | 11/1998 | Terstappen et al. |
| 5,842,477 A | 12/1998 | Naughton et al. |
| 5,843,633 A | 12/1998 | Yin et al. |
| 5,846,796 A | 12/1998 | Cerami et al. |
| 5,853,247 A | 12/1998 | Shroyer |
| 5,853,717 A | 12/1998 | Schinstine et al. |
| 5,855,608 A | 1/1999 | Brekke et al. |
| 5,855,613 A | 1/1999 | Antanavich et al. |
| 5,855,619 A | 1/1999 | Caplan et al. |
| 5,858,747 A | 1/1999 | Schinstine et al. |
| 5,858,782 A | 1/1999 | Long et al. |
| 5,861,315 A | 1/1999 | Nakahata |
| 5,866,115 A | 2/1999 | Kanz et al. |
| 5,866,420 A | 2/1999 | Talbot et al. |
| 5,868,930 A | 2/1999 | Kopf |
| 5,882,295 A | 3/1999 | Kope |
| 5,882,918 A | 3/1999 | Goffe |
| 5,882,929 A | 3/1999 | Fofonoff et al. |
| 5,888,807 A | 3/1999 | Palsson et al. |
| 5,902,741 A | 5/1999 | Purchio et al. |
| 5,906,827 A | 5/1999 | Khouri et al. |
| 5,906,934 A | 5/1999 | Grande et al. |
| 5,908,782 A | 6/1999 | Marshak et al. |
| 5,908,784 A | 6/1999 | Johnstone et al. |
| 5,912,177 A | 6/1999 | Turner et al. |
| 5,914,108 A | 6/1999 | Tsukamoto et al. |
| 5,922,597 A | 7/1999 | Verfaillie et al. |
| 5,922,847 A | 7/1999 | Broudy et al. |
| 5,925,567 A | 7/1999 | Kraus et al. |
| 5,928,945 A | 7/1999 | Seliktar et al. |
| 5,935,849 A | 8/1999 | Schinstine et al. |
| 5,938,929 A | 8/1999 | Shimagaki et al. |
| 5,939,323 A | 8/1999 | Valentini et al. |
| 5,942,225 A | 8/1999 | Bruder et al. |
| 5,955,353 A | 9/1999 | Amiot |
| 5,958,763 A | 9/1999 | Goffe |
| 5,965,436 A | 10/1999 | Thiede et al. |
| 5,972,703 A | 10/1999 | Long et al. |
| 5,980,795 A | 11/1999 | Klotzer et al. |
| 5,981,211 A | 11/1999 | Hu et al. |
| 5,981,708 A | 11/1999 | Lawman et al. |
| 5,985,653 A | 11/1999 | Armstrong et al. |
| 5,994,129 A | 11/1999 | Armstrong et al. |
| 5,998,184 A | 12/1999 | Shi |
| 6,001,585 A | 12/1999 | Gramer |
| 6,001,643 A | 12/1999 | Spaulding |
| 6,001,647 A | 12/1999 | Peck et al. |
| 6,004,743 A | 12/1999 | Kenyon et al. |
| 6,010,696 A | 1/2000 | Caplan et al. |
| 6,015,554 A | 1/2000 | Galy |
| 6,022,540 A | 2/2000 | Bruder et al. |
| 6,022,742 A | 2/2000 | Kopf |
| 6,022,743 A | 2/2000 | Naughton et al. |
| 6,027,743 A | 2/2000 | Khouri et al. |
| 6,030,836 A | 2/2000 | Thiede et al. |
| 6,040,180 A | 3/2000 | Johe |
| 6,045,818 A | 4/2000 | Cima et al. |
| 6,048,721 A | 4/2000 | Armstrong et al. |
| 6,048,727 A | 4/2000 | Kopf |
| 6,049,026 A | 4/2000 | Muschler |
| 6,054,121 A | 4/2000 | Cerami et al. |
| 6,060,270 A | 5/2000 | Humes |
| 6,066,317 A | 5/2000 | Yang et al. |
| 6,071,691 A | 6/2000 | Hoekstra et al. |
| 6,074,366 A | 6/2000 | Rogers et al. |
| 6,082,364 A | 7/2000 | Balian et al. |
| 6,083,747 A | 7/2000 | Wong et al. |
| 6,086,643 A | 7/2000 | Clark et al. |
| 6,087,113 A | 7/2000 | Caplan et al. |
| 6,096,532 A | 8/2000 | Armstrong et al. |
| 6,096,537 A | 8/2000 | Chappel |
| 6,103,117 A | 8/2000 | Shimagaki et al. |
| 6,103,522 A | 8/2000 | Torok-Storb et al. |
| 6,110,176 A | 8/2000 | Shapira |
| 6,110,482 A | 8/2000 | Khouri et al. |
| 6,114,307 A | 9/2000 | Jaspers et al. |
| 6,117,985 A | 9/2000 | Thomas et al. |
| 6,120,491 A | 9/2000 | Kohn et al. |
| 6,127,141 A | 10/2000 | Kopf |
| 6,129,911 A | 10/2000 | Faris |
| 6,143,293 A | 11/2000 | Weiss et al. |
| 6,146,360 A | 11/2000 | Rogers et al. |
| 6,146,888 A | 11/2000 | Smith et al. |
| 6,149,902 A | 11/2000 | Artavanis-Tsakonas et al. |
| 6,149,906 A | 11/2000 | Mosca |
| 6,150,164 A | 11/2000 | Humes |
| 6,152,964 A | 11/2000 | Van Blitterswijk et al. |
| 6,162,643 A | 12/2000 | Wille, Jr. |
| 6,165,225 A | 12/2000 | Antanavich et al. |
| 6,165,785 A | 12/2000 | Ogle et al. |
| 6,174,333 B1 | 1/2001 | Kadiyala et al. |
| 6,174,526 B1 | 1/2001 | Cerami et al. |
| 6,174,666 B1 | 1/2001 | Pavlakis et al. |
| 6,179,871 B1 | 1/2001 | Halpern |
| 6,197,325 B1 | 3/2001 | MacPhee et al. |
| 6,197,575 B1 | 3/2001 | Griffith et al. |
| 6,200,606 B1 | 3/2001 | Peterson et al. |
| 6,214,369 B1 | 4/2001 | Grande et al. |
| 6,214,574 B1 | 4/2001 | Kopf |
| 6,224,860 B1 | 5/2001 | Brown |
| 6,225,119 B1 | 5/2001 | Qasba et al. |
| 6,225,368 B1 | 5/2001 | D'Agostino et al. |
| 6,228,117 B1 | 5/2001 | De Bruijn et al. |
| 6,228,607 B1 | 5/2001 | Kersten et al. |
| 6,228,635 B1 | 5/2001 | Armstrong et al. |
| 6,238,908 B1 | 5/2001 | Armstrong et al. |
| 6,239,157 B1 | 5/2001 | Mbalaviele |
| 6,242,252 B1 | 6/2001 | Reid et al. |
| 6,248,319 B1 | 6/2001 | Zsebo et al. |
| 6,248,587 B1 | 6/2001 | Rodgers et al. |
| 6,255,112 B1 | 7/2001 | Thiede et al. |
| 6,258,597 B1 | 7/2001 | Bachovchin et al. |
| 6,258,778 B1 | 7/2001 | Rodgers et al. |
| 6,261,549 B1 | 7/2001 | Fernandez et al. |
| 6,280,718 B1 | 8/2001 | Kaufman et al. |
| 6,280,724 B1 | 8/2001 | Moore |
| 6,281,012 B1 | 8/2001 | McIntosh et al. |
| 6,281,195 B1 | 8/2001 | Rueger et al. |
| 6,287,864 B1 | 9/2001 | Bagnis et al. |
| 6,291,249 B1 | 9/2001 | Mahant et al. |
| 6,297,213 B1 | 10/2001 | Oppermann et al. |
| 6,299,650 B1 | 10/2001 | Van Blitterswijk et al. |
| 6,306,424 B1 | 10/2001 | Vyakarnam et al. |
| 6,306,575 B1 | 10/2001 | Thomas et al. |
| 6,322,784 B1 | 11/2001 | Pittenger et al. |
| 6,322,786 B1 | 11/2001 | Anderson |
| 6,326,198 B1 | 12/2001 | Emerson et al. |
| 6,326,201 B1 | 12/2001 | Fung et al. |
| 6,328,765 B1 | 12/2001 | Hardwick et al. |
| 6,328,960 B1 | 12/2001 | McIntosh et al. |
| 6,333,029 B1 | 12/2001 | Vyakarnam et al. |
| 6,335,195 B1 | 1/2002 | Rodgers et al. |
| 6,338,942 B2 | 1/2002 | Kraus et al. |
| 6,340,592 B1 | 1/2002 | Stringer |
| 6,342,370 B1 | 1/2002 | Connolly et al. |
| 6,355,239 B1 | 3/2002 | Bruder et al. |
| 6,358,252 B1 | 3/2002 | Shapira |
| 6,361,997 B1 | 3/2002 | Huss |
| 6,365,149 B2 | 4/2002 | Vyakarnam et al. |
| 6,368,636 B1 | 4/2002 | McIntosh et al. |
| 6,372,210 B2 | 4/2002 | Brown |
| 6,372,244 B1 | 4/2002 | Antanavich et al. |
| 6,372,494 B1 | 4/2002 | Naughton et al. |
| 6,372,892 B1 | 4/2002 | Ballinger et al. |
| 6,376,742 B1 | 4/2002 | Zdrahala et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,387,693 B2 | 5/2002 | Rieser et al. |
| 6,387,964 B1 | 5/2002 | D'Agostino et al. |
| 6,392,118 B1 | 5/2002 | Hammang et al. |
| 6,394,812 B1 | 5/2002 | Sullivan et al. |

(56) References Cited

U.S. PATENT DOCUMENTS

| | | |
|---|---|---|
| 6,399,580 B1 | 6/2002 | Elias et al. |
| 6,410,320 B1 | 6/2002 | Humes |
| 6,414,219 B1 | 7/2002 | Denhardt et al. |
| 6,416,496 B1 | 7/2002 | Rogers et al. |
| 6,417,205 B1 | 7/2002 | Cooke et al. |
| 6,419,829 B2 | 7/2002 | Ho et al. |
| 6,420,138 B1 | 7/2002 | Gentz et al. |
| 6,423,681 B1 | 7/2002 | Barasch et al. |
| 6,426,332 B1 | 7/2002 | Rueger et al. |
| 6,428,802 B1 | 8/2002 | Atala |
| 6,429,012 B1 | 8/2002 | Kraus et al. |
| 6,429,013 B1 | 8/2002 | Halvorsen et al. |
| 6,432,653 B1 | 8/2002 | Okarma |
| 6,432,711 B1 | 8/2002 | Dinsmore et al. |
| 6,440,407 B1 | 8/2002 | Bauer et al. |
| 6,440,734 B1 | 8/2002 | Pykett et al. |
| 6,451,562 B1 | 9/2002 | Ruben et al. |
| 6,454,811 B1 | 9/2002 | Sherwood et al. |
| 6,455,678 B1 | 9/2002 | Yin et al. |
| 6,458,585 B1 | 10/2002 | Vachula et al. |
| 6,458,589 B1 | 10/2002 | Rambhatla et al. |
| 6,461,495 B1 | 10/2002 | Morrissey et al. |
| 6,461,853 B1 | 10/2002 | Zhu |
| 6,464,983 B1 | 10/2002 | Grotendorst |
| 6,465,205 B2 | 10/2002 | Hicks, Jr. |
| 6,465,247 B1 | 10/2002 | Weissman et al. |
| 6,465,249 B2 | 10/2002 | Reya et al. |
| 6,468,794 B1 | 10/2002 | Uchida et al. |
| 6,472,200 B1 | 10/2002 | Mitrani |
| 6,475,481 B2 | 11/2002 | Talmadge |
| 6,479,064 B1 | 11/2002 | Atala |
| 6,482,231 B1 | 11/2002 | Abatangelo et al. |
| 6,482,411 B1 | 11/2002 | Ahuja et al. |
| 6,482,645 B2 | 11/2002 | Atala |
| 6,482,926 B1 | 11/2002 | Thomas et al. |
| 6,488,925 B2 | 12/2002 | Ruben et al. |
| 6,491,918 B1 | 12/2002 | Thomas et al. |
| 6,495,129 B1 | 12/2002 | Li et al. |
| 6,495,364 B2 | 12/2002 | Hammang et al. |
| 6,497,875 B1 | 12/2002 | Sorrell et al. |
| 6,498,034 B1 | 12/2002 | Strobl |
| 6,506,574 B1 | 1/2003 | Rambhatla et al. |
| 6,511,510 B1 | 1/2003 | de Bruijn et al. |
| 6,511,767 B1 | 1/2003 | Calver et al. |
| 6,511,958 B1 | 1/2003 | Atkinson et al. |
| 6,514,514 B1 | 2/2003 | Atkinson et al. |
| 6,524,452 B1 | 2/2003 | Clark et al. |
| 6,528,052 B1 | 3/2003 | Smith et al. |
| 6,528,245 B2 | 3/2003 | Sanchez-Ramos et al. |
| 6,531,445 B1 | 3/2003 | Cohen et al. |
| 6,534,084 B1 | 3/2003 | Vyakarnam et al. |
| 6,537,807 B1 | 3/2003 | Smith et al. |
| 6,541,024 B1 | 4/2003 | Kadiyala et al. |
| 6,541,249 B2 | 4/2003 | Wager et al. |
| 6,544,506 B2 | 4/2003 | Reisner |
| 6,548,734 B1 | 4/2003 | Glimcher et al. |
| 6,555,324 B1 | 4/2003 | Olweus et al. |
| 6,555,374 B1 | 4/2003 | Gimble et al. |
| 6,559,119 B1 | 5/2003 | Burgess et al. |
| 6,562,616 B1 | 5/2003 | Toner et al. |
| 6,565,843 B1 | 5/2003 | Cohen et al. |
| 6,566,126 B2 | 5/2003 | Cadwell |
| 6,569,421 B2 | 5/2003 | Hodges |
| 6,569,427 B1 | 5/2003 | Boyse et al. |
| 6,569,428 B1 | 5/2003 | Isner et al. |
| 6,569,654 B2 | 5/2003 | Shastri et al. |
| 6,576,188 B1 | 6/2003 | Rose et al. |
| 6,576,428 B1 | 6/2003 | Assenmacher et al. |
| 6,576,464 B2 | 6/2003 | Gold et al. |
| 6,576,465 B1 | 6/2003 | Long |
| 6,582,471 B1 | 6/2003 | Bittmann et al. |
| 6,582,955 B2 | 6/2003 | Martinez et al. |
| 6,586,192 B1 | 7/2003 | Peschle et al. |
| 6,589,728 B2 | 7/2003 | Csete et al. |
| 6,589,786 B1 | 7/2003 | Mangano et al. |
| 6,596,274 B1 | 7/2003 | Abatangelo et al. |
| 6,599,300 B2 | 7/2003 | Vibe-Hansen et al. |
| 6,599,520 B2 | 7/2003 | Scarborough et al. |
| 6,610,535 B1 | 8/2003 | Lu et al. |
| 6,613,798 B1 | 9/2003 | Porter et al. |
| 6,616,912 B2 | 9/2003 | Eddleman et al. |
| 6,617,070 B1 | 9/2003 | Morrissey et al. |
| 6,617,152 B2 | 9/2003 | Bryhan et al. |
| 6,617,159 B1 | 9/2003 | Cancedda et al. |
| 6,623,749 B2 | 9/2003 | Williams et al. |
| 6,623,942 B2 | 9/2003 | Ruben et al. |
| 6,624,108 B1 | 9/2003 | Clark et al. |
| 6,626,950 B2 | 9/2003 | Brown et al. |
| 6,627,191 B1 | 9/2003 | Bartelmez et al. |
| 6,632,425 B1 | 10/2003 | Li et al. |
| 6,632,620 B1 | 10/2003 | Makarovskiy |
| 6,632,934 B1 | 10/2003 | Moreadith et al. |
| 6,638,765 B1 | 10/2003 | Rosenberg |
| 6,642,019 B1 | 11/2003 | Anderson et al. |
| 6,642,048 B2 | 11/2003 | Xu et al. |
| 6,642,049 B1 | 11/2003 | Chute et al. |
| 6,642,201 B1 | 11/2003 | Khavinson et al. |
| 6,645,489 B2 | 11/2003 | Pykett et al. |
| 6,645,727 B2 | 11/2003 | Thomas et al. |
| 6,645,763 B2 | 11/2003 | Kobayashi et al. |
| 6,649,189 B2 | 11/2003 | Talmadge et al. |
| 6,649,595 B2 | 11/2003 | Clackson et al. |
| 6,649,631 B1 | 11/2003 | Orme et al. |
| 6,653,105 B2 | 11/2003 | Triglia et al. |
| 6,653,134 B2 | 11/2003 | Prockop et al. |
| 6,660,523 B2 | 12/2003 | Blom et al. |
| 6,662,805 B2 | 12/2003 | Frondoza et al. |
| 6,667,034 B2 | 12/2003 | Palsson et al. |
| 6,667,176 B1 | 12/2003 | Funk et al. |
| 6,670,169 B1 | 12/2003 | Schob et al. |
| 6,670,175 B2 | 12/2003 | Wang et al. |
| 6,673,603 B2 | 1/2004 | Baetge et al. |
| 6,673,606 B1 | 1/2004 | Tennekoon et al. |
| 6,677,306 B1 | 1/2004 | Veis et al. |
| 6,683,192 B2 | 1/2004 | Baxter et al. |
| 6,685,936 B2 | 2/2004 | McIntosh et al. |
| 6,685,971 B2 | 2/2004 | Xu |
| 6,686,198 B1 | 2/2004 | Melton et al. |
| 6,696,575 B2 | 2/2004 | Schmidt et al. |
| 6,699,716 B2 | 3/2004 | Sullivan et al. |
| 6,703,017 B1 | 3/2004 | Peck et al. |
| 6,703,209 B1 | 3/2004 | Baetscher et al. |
| 6,706,293 B1 | 3/2004 | Quintanilla Almagro et al. |
| 6,709,864 B1 | 3/2004 | Pittenger et al. |
| 6,712,850 B2 | 3/2004 | Vyakarnam et al. |
| 6,719,969 B1 | 4/2004 | Hogaboam et al. |
| 6,719,970 B1 | 4/2004 | Costantino et al. |
| 6,720,340 B1 | 4/2004 | Cooke et al. |
| 6,730,314 B2 | 5/2004 | Jeschke et al. |
| 6,730,315 B2 | 5/2004 | Usala et al. |
| 6,730,510 B2 | 5/2004 | Roos et al. |
| 6,733,746 B2 | 5/2004 | Daley et al. |
| 6,734,000 B2 | 5/2004 | Chin et al. |
| 6,740,493 B1 | 5/2004 | Long et al. |
| 6,759,039 B2 | 7/2004 | Tsang et al. |
| 6,759,245 B1 | 7/2004 | Toner et al. |
| 6,761,883 B2 | 7/2004 | Weissman et al. |
| 6,761,887 B1 | 7/2004 | Kavalkovich et al. |
| 6,767,699 B2 | 7/2004 | Polo et al. |
| 6,767,737 B1 | 7/2004 | Wilson et al. |
| 6,767,738 B1 | 7/2004 | Gage et al. |
| 6,767,740 B2 | 7/2004 | Sramek et al. |
| 6,770,478 B2 | 8/2004 | Crowe et al. |
| 6,777,227 B2 | 8/2004 | Ricci et al. |
| 6,777,231 B1 | 8/2004 | Katz et al. |
| 6,780,612 B1 | 8/2004 | Ford et al. |
| 6,787,355 B1 | 9/2004 | Miller et al. |
| 6,790,455 B2 | 9/2004 | Chu et al. |
| 6,793,939 B2 | 9/2004 | Badylak |
| 6,797,269 B2 | 9/2004 | Mosca et al. |
| 6,797,514 B2 | 9/2004 | Berenson et al. |
| 6,800,480 B1 | 10/2004 | Bodnar et al. |
| 6,802,971 B2 | 10/2004 | Gorsuch et al. |
| 6,805,860 B1 | 10/2004 | Alt |

(56) References Cited

U.S. PATENT DOCUMENTS

| | | |
|---|---|---|
| 6,809,117 B2 | 10/2004 | Enikolopov et al. |
| 6,811,773 B1 | 11/2004 | Gentz et al. |
| 6,811,776 B2 | 11/2004 | Kale et al. |
| 6,814,961 B1 | 11/2004 | Jensen et al. |
| 6,821,513 B1 | 11/2004 | Fleming |
| 6,821,790 B2 | 11/2004 | Mahant et al. |
| 6,828,145 B2 | 12/2004 | Avital et al. |
| 6,833,269 B2 | 12/2004 | Carpenter |
| 6,835,377 B2 | 12/2004 | Goldberg et al. |
| 6,835,566 B2 | 12/2004 | Smith et al. |
| 6,838,284 B2 | 1/2005 | de Bruijn et al. |
| 6,841,150 B2 | 1/2005 | Halvorsen et al. |
| 6,841,151 B2 | 1/2005 | Stringer |
| 6,841,294 B1 | 1/2005 | Morrissey et al. |
| 6,841,355 B2 | 1/2005 | Livant |
| 6,841,386 B2 | 1/2005 | Kraus et al. |
| 6,841,542 B2 | 1/2005 | Bartelmez et al. |
| 6,844,011 B1 | 1/2005 | Faustman |
| 6,844,187 B1 | 1/2005 | Weschler et al. |
| 6,849,051 B2 | 2/2005 | Sramek et al. |
| 6,849,255 B2 | 2/2005 | Gazit et al. |
| 6,849,454 B2 | 2/2005 | Kelly et al. |
| 6,849,662 B2 | 2/2005 | Enikolopov et al. |
| 6,852,308 B2 | 2/2005 | Kohn et al. |
| 6,852,321 B2 | 2/2005 | Colucci et al. |
| 6,852,533 B1 | 2/2005 | Rafii et al. |
| 6,855,242 B1 | 2/2005 | Comninellis et al. |
| 6,855,542 B2 | 2/2005 | DiMilla et al. |
| 6,863,900 B2 | 3/2005 | Kadiyala et al. |
| 6,866,843 B2 | 3/2005 | Habener et al. |
| 6,872,389 B1 | 3/2005 | Faris |
| 6,875,430 B2 | 4/2005 | McIntosh et al. |
| 6,887,600 B2 | 5/2005 | Morrissey et al. |
| 6,887,704 B2 | 5/2005 | Peled et al. |
| 6,908,763 B1 | 6/2005 | Akashi et al. |
| 6,911,201 B1 | 6/2005 | Merchav et al. |
| 6,914,279 B2 | 7/2005 | Lu et al. |
| 6,939,955 B2 | 9/2005 | Rameshwar |
| 6,943,008 B1 | 9/2005 | Ma |
| 6,965,018 B2 | 11/2005 | Mikesell et al. |
| 6,969,308 B2 | 11/2005 | Doi et al. |
| 6,979,308 B1 | 12/2005 | McDonald et al. |
| 6,979,321 B2 | 12/2005 | Geis et al. |
| 6,988,004 B2 | 1/2006 | Kanno et al. |
| 7,008,394 B2 | 3/2006 | Geise et al. |
| 7,015,037 B1 | 3/2006 | Furcht et al. |
| 7,029,666 B2 | 4/2006 | Bruder et al. |
| 7,033,339 B1 | 4/2006 | Lynn |
| 7,033,823 B2 | 4/2006 | Chang |
| 7,041,493 B2 | 5/2006 | Rao |
| 7,045,098 B2 | 5/2006 | Stephens |
| 7,052,517 B2 | 5/2006 | Murphy et al. |
| 7,056,493 B2 | 6/2006 | Kohn et al. |
| 7,112,441 B2 | 9/2006 | Uemura et al. |
| 7,118,672 B2 | 10/2006 | Husain et al. |
| 7,122,178 B1 | 10/2006 | Simmons et al. |
| 7,160,719 B2 | 1/2007 | Nyberg |
| 7,169,295 B2 | 1/2007 | Husain et al. |
| 7,172,696 B1 | 2/2007 | Martinez et al. |
| 7,175,763 B2 | 2/2007 | Husain et al. |
| 7,192,776 B2 | 3/2007 | Stephens |
| 7,195,711 B2 | 3/2007 | Gorsuch et al. |
| 7,250,154 B2 | 7/2007 | Kohn et al. |
| 7,270,996 B2 | 9/2007 | Cannon et al. |
| 7,271,234 B2 | 9/2007 | Kohn et al. |
| 7,294,259 B2 | 11/2007 | Cote et al. |
| 7,300,571 B2 | 11/2007 | Cote et al. |
| 7,303,676 B2 | 12/2007 | Husain et al. |
| 7,303,677 B2 | 12/2007 | Cote et al. |
| 7,341,062 B2 | 3/2008 | Chachques et al. |
| 7,358,001 B2 | 4/2008 | Morrissey et al. |
| 7,361,493 B1 | 4/2008 | Hammond et al. |
| 7,368,169 B2 | 5/2008 | Kohn et al. |
| 7,378,271 B2 | 5/2008 | Bader |
| 7,399,872 B2 | 7/2008 | Webster et al. |
| 7,416,884 B2 | 8/2008 | Gemmiti et al. |
| 7,425,440 B2 | 9/2008 | Malinge et al. |
| 7,435,586 B2 | 10/2008 | Bartlett et al. |
| 7,438,902 B2 | 10/2008 | Habener et al. |
| 7,439,057 B2 | 10/2008 | Frangos et al. |
| 7,452,529 B2 | 11/2008 | Brown, Jr. et al. |
| 7,491,388 B1 | 2/2009 | Mc Intosh et al. |
| 7,494,811 B2 | 2/2009 | Wolfinbarger, Jr. et al. |
| 7,514,074 B2 | 4/2009 | Pittenger et al. |
| 7,514,075 B2 | 4/2009 | Hedrick et al. |
| 7,524,676 B2 | 4/2009 | Reiter et al. |
| 7,531,351 B2 | 5/2009 | Marx et al. |
| 7,534,601 B2 | 5/2009 | Wikswo et al. |
| 7,534,609 B2 | 5/2009 | Merchav et al. |
| 7,572,374 B2 | 8/2009 | Gorsuch et al. |
| 7,579,179 B2 | 8/2009 | Bryhan et al. |
| 7,585,412 B2 | 9/2009 | Gorsuch et al. |
| 7,588,938 B2 | 9/2009 | Ma |
| 7,598,075 B2 | 10/2009 | Smith et al. |
| 7,608,447 B2 | 10/2009 | Cohen et al. |
| 7,659,118 B2 | 2/2010 | Furcht et al. |
| 7,678,573 B2 | 3/2010 | Merchav et al. |
| 7,682,822 B2 | 3/2010 | Noll et al. |
| 7,682,823 B1 | 3/2010 | Runyon |
| 7,718,430 B2 | 5/2010 | Antwiler |
| 7,722,896 B2 | 5/2010 | Kohn et al. |
| D620,732 S | 8/2010 | Andrews |
| 7,838,122 B2 | 11/2010 | Kohn et al. |
| 7,838,289 B2 | 11/2010 | Furcht et al. |
| 7,892,829 B2 | 2/2011 | Pittenger et al. |
| 7,919,307 B2 | 4/2011 | Klaus et al. |
| 7,927,587 B2 | 4/2011 | Blazer et al. |
| 7,989,851 B2 | 8/2011 | Lu et al. |
| 8,008,528 B2 | 8/2011 | Kohn et al. |
| 8,034,365 B2 | 10/2011 | Baluca |
| 8,075,881 B2 | 12/2011 | Verfaillie et al. |
| 8,147,824 B2 | 4/2012 | Maziarz et al. |
| 8,147,863 B2 | 4/2012 | Kohn et al. |
| 8,158,120 B2 | 4/2012 | Pittenger et al. |
| 8,158,121 B2 | 4/2012 | Pittenger et al. |
| 8,252,280 B1 | 8/2012 | Verfaillie et al. |
| 8,252,887 B2 | 8/2012 | Bolikal et al. |
| 8,288,159 B2 | 10/2012 | Warren et al. |
| 8,288,590 B2 | 10/2012 | Kohn et al. |
| 8,298,823 B2 | 10/2012 | Warren et al. |
| 8,309,347 B2 | 11/2012 | Antwiler |
| 8,361,453 B2 | 1/2013 | Uhrich et al. |
| 8,377,683 B2 | 2/2013 | Lu et al. |
| 8,383,397 B2 | 2/2013 | Wojciechowski et al. |
| 8,383,806 B2 | 2/2013 | Rameshwar |
| 8,399,245 B2 | 3/2013 | Leuthaeuser et al. |
| 8,415,449 B2 | 4/2013 | Kohn et al. |
| 8,435,781 B2 | 5/2013 | Kodama |
| 8,461,289 B2 | 6/2013 | Kohn et al. |
| 8,476,399 B2 | 7/2013 | Bolikal et al. |
| 8,486,621 B2 | 7/2013 | Luo et al. |
| 8,486,695 B2 | 7/2013 | Danilkovitch et al. |
| 8,492,140 B2 | 7/2013 | Smith et al. |
| 8,492,150 B2 | 7/2013 | Parker et al. |
| 8,524,496 B2 | 9/2013 | Meiron et al. |
| 8,529,888 B2 | 9/2013 | Meiron et al. |
| 8,540,499 B2 | 9/2013 | Page et al. |
| 8,551,511 B2 | 10/2013 | Brandom et al. |
| 8,580,249 B2 | 11/2013 | Blazer et al. |
| 8,678,638 B2 | 3/2014 | Wong |
| 8,785,181 B2 | 7/2014 | Antwiler |
| 8,852,570 B2 | 10/2014 | Pittenger et al. |
| 8,852,571 B2 | 10/2014 | Pittenger et al. |
| 8,852,572 B2 | 10/2014 | Pittenger et al. |
| 8,852,573 B2 | 10/2014 | Pittenger et al. |
| 8,852,574 B2 | 10/2014 | Pittenger et al. |
| 8,852,575 B2 | 10/2014 | Pittenger et al. |
| 8,895,291 B2 | 11/2014 | DiLorenzo et al. |
| 9,057,045 B2 | 6/2015 | Gibbons et al. |
| 9,109,193 B2 | 8/2015 | Galliher et al. |
| 9,175,259 B2 | 11/2015 | Nankervis |
| 9,220,810 B2 | 12/2015 | Ma et al. |
| 9,441,195 B2 | 9/2016 | Wojciechowski et al. |
| 9,534,198 B2 | 1/2017 | Page et al. |

(56) References Cited

U.S. PATENT DOCUMENTS

| | | |
|---|---|---|
| 9,732,313 B2 | 8/2017 | Hirschel et al. |
| 10,093,956 B2 | 10/2018 | Hirschel et al. |
| 10,494,421 B2 | 12/2019 | Castillo |
| 11,008,547 B2 * | 5/2021 | Nankervis .............. C12M 29/16 |
| 2001/0017188 A1 | 8/2001 | Cooley et al. |
| 2001/0020086 A1 | 9/2001 | Hubbell et al. |
| 2001/0021516 A1 | 9/2001 | Wei et al. |
| 2001/0029046 A1 | 10/2001 | Beaulieu |
| 2001/0033834 A1 | 10/2001 | Wilkison et al. |
| 2001/0036663 A1 | 11/2001 | Kraus et al. |
| 2001/0041687 A1 | 11/2001 | Mruk |
| 2001/0044413 A1 | 11/2001 | Pierce et al. |
| 2001/0049139 A1 | 12/2001 | Lagasse et al. |
| 2002/0015724 A1 | 2/2002 | Yang et al. |
| 2002/0018804 A1 | 2/2002 | Austin et al. |
| 2002/0028510 A1 | 3/2002 | Sanberg et al. |
| 2002/0031757 A1 | 3/2002 | Ohgushi et al. |
| 2002/0037278 A1 | 3/2002 | Ueno et al. |
| 2002/0045260 A1 | 4/2002 | Hung et al. |
| 2002/0064869 A1 | 5/2002 | Ebner et al. |
| 2002/0076400 A1 | 6/2002 | Katz et al. |
| 2002/0077687 A1 | 6/2002 | Ahn |
| 2002/0082698 A1 | 6/2002 | Parenteau et al. |
| 2002/0116054 A1 | 8/2002 | Lundell et al. |
| 2002/0128581 A1 | 9/2002 | Vishnoi et al. |
| 2002/0128582 A1 | 9/2002 | Farrell et al. |
| 2002/0128583 A1 | 9/2002 | Min et al. |
| 2002/0128584 A1 | 9/2002 | Brown et al. |
| 2002/0130100 A1 | 9/2002 | Smith |
| 2002/0132343 A1 | 9/2002 | Lum |
| 2002/0139743 A1 | 10/2002 | Critz et al. |
| 2002/0142457 A1 | 10/2002 | Umezawa et al. |
| 2002/0146678 A1 | 10/2002 | Benvenisty |
| 2002/0146817 A1 | 10/2002 | Cannon et al. |
| 2002/0150989 A1 | 10/2002 | Greene et al. |
| 2002/0151056 A1 | 10/2002 | Sasai et al. |
| 2002/0159981 A1 | 10/2002 | Peled et al. |
| 2002/0160032 A1 | 10/2002 | Long et al. |
| 2002/0160510 A1 | 10/2002 | Hariri |
| 2002/0168765 A1 | 11/2002 | Prockop et al. |
| 2002/0169408 A1 | 11/2002 | Beretta et al. |
| 2002/0182241 A1 | 12/2002 | Borenstein et al. |
| 2002/0182664 A1 | 12/2002 | Dolecek et al. |
| 2002/0188962 A1 | 12/2002 | Denhardt et al. |
| 2002/0197240 A1 | 12/2002 | Chiu |
| 2003/0021850 A1 | 1/2003 | Xu |
| 2003/0022390 A1 | 1/2003 | Stephens |
| 2003/0027330 A1 | 2/2003 | Lanza et al. |
| 2003/0027331 A1 | 2/2003 | Yan et al. |
| 2003/0032143 A1 | 2/2003 | Neff et al. |
| 2003/0036168 A1 | 2/2003 | Ni et al. |
| 2003/0040113 A1 | 2/2003 | Mizuno et al. |
| 2003/0049236 A1 | 3/2003 | Kassem et al. |
| 2003/0054331 A1 | 3/2003 | Fraser et al. |
| 2003/0059851 A1 | 3/2003 | Smith |
| 2003/0059939 A1 | 3/2003 | Page et al. |
| 2003/0078345 A1 | 4/2003 | Morrisey |
| 2003/0082795 A1 | 5/2003 | Shuler et al. |
| 2003/0086915 A1 | 5/2003 | Rader et al. |
| 2003/0089471 A1 | 5/2003 | Gehr et al. |
| 2003/0092101 A1 | 5/2003 | Ni et al. |
| 2003/0101465 A1 | 5/2003 | Lawman et al. |
| 2003/0103957 A1 | 6/2003 | McKerracher |
| 2003/0104568 A1 | 6/2003 | Lee |
| 2003/0113813 A1 | 6/2003 | Heidaran et al. |
| 2003/0113910 A1 | 6/2003 | Levanduski |
| 2003/0124091 A1 | 7/2003 | Tuse et al. |
| 2003/0124721 A1 | 7/2003 | Cheatham et al. |
| 2003/0130593 A1 | 7/2003 | Gonzalez |
| 2003/0133918 A1 | 7/2003 | Sherley |
| 2003/0138950 A1 | 7/2003 | McAllister et al. |
| 2003/0143727 A1 | 7/2003 | Chang |
| 2003/0148152 A1 | 8/2003 | Morrisey |
| 2003/0149011 A1 | 8/2003 | Ackerman et al. |
| 2003/0152558 A1 | 8/2003 | Luft et al. |
| 2003/0157078 A1 | 8/2003 | Hall et al. |
| 2003/0157709 A1 | 8/2003 | DiMilla et al. |
| 2003/0161817 A1 | 8/2003 | Young et al. |
| 2003/0166272 A1 | 9/2003 | Abuljadayel |
| 2003/0170214 A1 | 9/2003 | Bader |
| 2003/0180296 A1 | 9/2003 | Salcedo et al. |
| 2003/0185817 A1 | 10/2003 | Thomas et al. |
| 2003/0202938 A1 | 10/2003 | Rameshwar |
| 2003/0203483 A1 | 10/2003 | Seshi |
| 2003/0204323 A1 | 10/2003 | Morrisey |
| 2003/0211602 A1 | 11/2003 | Atala |
| 2003/0211603 A1 | 11/2003 | Earp et al. |
| 2003/0216718 A1 | 11/2003 | Hamblin et al. |
| 2003/0219898 A1 | 11/2003 | Sugaya et al. |
| 2003/0223968 A1 | 12/2003 | Yang |
| 2003/0224420 A1 | 12/2003 | Hellerstein et al. |
| 2003/0224510 A1 | 12/2003 | Yamaguchi et al. |
| 2003/0225010 A1 | 12/2003 | Rameshwar |
| 2003/0232432 A1 | 12/2003 | Bhat |
| 2003/0232752 A1 | 12/2003 | Freeman et al. |
| 2003/0235909 A1 | 12/2003 | Hariri et al. |
| 2004/0009158 A1 | 1/2004 | Sands et al. |
| 2004/0009589 A1 | 1/2004 | Levenberg et al. |
| 2004/0010231 A1 | 1/2004 | Leonhardt et al. |
| 2004/0014209 A1 | 1/2004 | Lassar et al. |
| 2004/0018174 A1 | 1/2004 | Palasis |
| 2004/0018617 A1 | 1/2004 | Hwang |
| 2004/0023324 A1 | 2/2004 | Sakano et al. |
| 2004/0023370 A1 | 2/2004 | Yu et al. |
| 2004/0027914 A1 | 2/2004 | Vrane |
| 2004/0033214 A1 | 2/2004 | Young et al. |
| 2004/0033599 A1 | 2/2004 | Rosenberg |
| 2004/0037811 A1 | 2/2004 | Penn et al. |
| 2004/0037815 A1 | 2/2004 | Clarke et al. |
| 2004/0038316 A1 | 2/2004 | Kaiser et al. |
| 2004/0053869 A1 | 3/2004 | Andrews et al. |
| 2004/0062753 A1 | 4/2004 | Rezania et al. |
| 2004/0063205 A1 | 4/2004 | Xu |
| 2004/0067585 A1 | 4/2004 | Wang et al. |
| 2004/0071668 A1 | 4/2004 | Bays et al. |
| 2004/0072259 A1 | 4/2004 | Scadden et al. |
| 2004/0077079 A1 | 4/2004 | Storgaard et al. |
| 2004/0079248 A1 | 4/2004 | Mayer et al. |
| 2004/0087016 A1 | 5/2004 | Keating et al. |
| 2004/0091936 A1 | 5/2004 | West |
| 2004/0096476 A1 | 5/2004 | Uhrich et al. |
| 2004/0097408 A1 | 5/2004 | Leder et al. |
| 2004/0101959 A1 | 5/2004 | Marko et al. |
| 2004/0107453 A1 | 6/2004 | Furcht et al. |
| 2004/0110286 A1 | 6/2004 | Bhatia |
| 2004/0115804 A1 | 6/2004 | Fu et al. |
| 2004/0115806 A1 | 6/2004 | Fu |
| 2004/0120932 A1 | 6/2004 | Zahner |
| 2004/0121461 A1 | 6/2004 | Honmou et al. |
| 2004/0121464 A1 | 6/2004 | Rathjen et al. |
| 2004/0126405 A1 | 7/2004 | Sahatjian et al. |
| 2004/0128077 A1 | 7/2004 | Koebler et al. |
| 2004/0131601 A1 | 7/2004 | Epstein et al. |
| 2004/0132184 A1 | 7/2004 | Dennis et al. |
| 2004/0136967 A1 | 7/2004 | Weiss et al. |
| 2004/0137612 A1 | 7/2004 | Baksh |
| 2004/0137613 A1 | 7/2004 | Vacanti et al. |
| 2004/0143174 A1 | 7/2004 | Brubaker |
| 2004/0143863 A1 | 7/2004 | Li et al. |
| 2004/0151700 A1 | 8/2004 | Harlan et al. |
| 2004/0151701 A1 | 8/2004 | Kim et al. |
| 2004/0151706 A1 | 8/2004 | Shakhov et al. |
| 2004/0151729 A1 | 8/2004 | Michalopoulos et al. |
| 2004/0152190 A1 | 8/2004 | Sumita |
| 2004/0161419 A1 | 8/2004 | Strom et al. |
| 2004/0171533 A1 | 9/2004 | Zehentner et al. |
| 2004/0180347 A1 | 9/2004 | Stanton et al. |
| 2004/0191902 A1 | 9/2004 | Hambor et al. |
| 2004/0197310 A1 | 10/2004 | Sanberg et al. |
| 2004/0197375 A1 | 10/2004 | Rezania et al. |
| 2004/0208786 A1 | 10/2004 | Kevy et al. |
| 2004/0214275 A1 | 10/2004 | Soejima et al. |
| 2004/0219134 A1 | 11/2004 | Naughton et al. |
| 2004/0219136 A1 | 11/2004 | Hariri |

(56) References Cited

U.S. PATENT DOCUMENTS

| | | |
|---|---|---|
| 2004/0219563 A1 | 11/2004 | West et al. |
| 2004/0224403 A1 | 11/2004 | Bhatia |
| 2004/0229351 A1 | 11/2004 | Rodriguez et al. |
| 2004/0234972 A1 | 11/2004 | Owens et al. |
| 2004/0235158 A1 | 11/2004 | Bartlett et al. |
| 2004/0235160 A1 | 11/2004 | Nishikawa et al. |
| 2004/0235166 A1 | 11/2004 | Prockop et al. |
| 2004/0242469 A1 | 12/2004 | Lee et al. |
| 2004/0258669 A1 | 12/2004 | Dzau et al. |
| 2004/0259242 A1 | 12/2004 | Malinge et al. |
| 2004/0259254 A1 | 12/2004 | Honmou et al. |
| 2004/0260058 A1 | 12/2004 | Scheek et al. |
| 2004/0260318 A1 | 12/2004 | Hunter et al. |
| 2004/0265996 A1 | 12/2004 | Schwarz et al. |
| 2005/0002914 A1 | 1/2005 | Rosen et al. |
| 2005/0003460 A1 | 1/2005 | Nilsson et al. |
| 2005/0003527 A1 | 1/2005 | Lang et al. |
| 2005/0003534 A1 | 1/2005 | Huberman et al. |
| 2005/0008624 A1 | 1/2005 | Peled et al. |
| 2005/0008626 A1 | 1/2005 | Fraser et al. |
| 2005/0009178 A1 | 1/2005 | Yost et al. |
| 2005/0009179 A1 | 1/2005 | Gemmiti et al. |
| 2005/0009181 A1 | 1/2005 | Black et al. |
| 2005/0013804 A1 | 1/2005 | Kato et al. |
| 2005/0014252 A1 | 1/2005 | Chu et al. |
| 2005/0014253 A1 | 1/2005 | Ehmann et al. |
| 2005/0014254 A1 | 1/2005 | Kruse |
| 2005/0014255 A1 | 1/2005 | Tang et al. |
| 2005/0019801 A1 | 1/2005 | Rubin et al. |
| 2005/0019908 A1 | 1/2005 | Hariri |
| 2005/0019910 A1 | 1/2005 | Takagi et al. |
| 2005/0019911 A1 | 1/2005 | Gronthos et al. |
| 2005/0026836 A1 | 2/2005 | Dack et al. |
| 2005/0031587 A1 | 2/2005 | Tsutsui et al. |
| 2005/0031595 A1 | 2/2005 | Peled et al. |
| 2005/0031598 A1 | 2/2005 | Levenberg et al. |
| 2005/0032122 A1 | 2/2005 | Hwang et al. |
| 2005/0032207 A1 | 2/2005 | Wobus et al. |
| 2005/0032209 A1 | 2/2005 | Messina et al. |
| 2005/0032218 A1 | 2/2005 | Gerlach |
| 2005/0036980 A1 | 2/2005 | Chaney et al. |
| 2005/0037488 A1 | 2/2005 | Mitalipova et al. |
| 2005/0037490 A1 | 2/2005 | Rosenberg et al. |
| 2005/0037492 A1 | 2/2005 | Xu et al. |
| 2005/0037493 A1 | 2/2005 | Mandalam et al. |
| 2005/0037949 A1 | 2/2005 | O'Brien et al. |
| 2005/0106119 A1 | 5/2005 | Brandom et al. |
| 2005/0106127 A1 | 5/2005 | Kraus et al. |
| 2005/0112447 A1 | 5/2005 | Fletcher et al. |
| 2005/0112762 A1 | 5/2005 | Hart et al. |
| 2005/0118712 A1 | 6/2005 | Tsai et al. |
| 2005/0130297 A1 | 6/2005 | Sarem et al. |
| 2005/0136093 A1 | 6/2005 | Denk |
| 2005/0137517 A1 | 6/2005 | Blickhan et al. |
| 2005/0142162 A1 | 6/2005 | Hunter et al. |
| 2005/0149157 A1 | 7/2005 | Hunter et al. |
| 2005/0152946 A1 | 7/2005 | Hunter et al. |
| 2005/0158289 A1 | 7/2005 | Simmons et al. |
| 2005/0172340 A1 | 8/2005 | Logvinov et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0180957 A1 | 8/2005 | Scharp et al. |
| 2005/0181502 A1 | 8/2005 | Furcht et al. |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0186671 A1 | 8/2005 | Cannon et al. |
| 2005/0187140 A1 | 8/2005 | Hunter et al. |
| 2005/0196421 A1 | 9/2005 | Hunter et al. |
| 2005/0208095 A1 | 9/2005 | Hunter et al. |
| 2005/0244963 A1 | 11/2005 | Teplyashin |
| 2005/0249731 A1 | 11/2005 | Aslan et al. |
| 2005/0255118 A1 | 11/2005 | Wehner |
| 2005/0261674 A1 | 11/2005 | Nobis et al. |
| 2005/0277577 A1 | 12/2005 | Hunter et al. |
| 2005/0281790 A1 | 12/2005 | Simmons et al. |
| 2005/0282733 A1 | 12/2005 | Prins et al. |
| 2005/0283844 A1 | 12/2005 | Furcht et al. |
| 2006/0002900 A1 | 1/2006 | Binder et al. |
| 2006/0008452 A1 | 1/2006 | Simmons et al. |
| 2006/0019388 A1 | 1/2006 | Hutmacher et al. |
| 2006/0019389 A1 | 1/2006 | Yayon et al. |
| 2006/0054941 A1 | 3/2006 | Lu et al. |
| 2006/0083720 A1 | 4/2006 | Fraser et al. |
| 2006/0099198 A1 | 5/2006 | Thomson et al. |
| 2006/0166364 A1 | 7/2006 | Senesac |
| 2006/0172008 A1 | 8/2006 | Yayon et al. |
| 2006/0193840 A1 | 8/2006 | Gronthos et al. |
| 2006/0228798 A1 | 10/2006 | Verfaillie et al. |
| 2006/0233834 A1 | 10/2006 | Guehenneux et al. |
| 2006/0239909 A1 | 10/2006 | Anderson et al. |
| 2006/0258586 A1 | 11/2006 | Sheppard et al. |
| 2006/0258933 A1 | 11/2006 | Ellis et al. |
| 2006/0259998 A1 | 11/2006 | Brumbley et al. |
| 2006/0280748 A1 | 12/2006 | Buckheit |
| 2006/0286077 A1 | 12/2006 | Gronthos et al. |
| 2007/0005148 A1 | 1/2007 | Barofsky et al. |
| 2007/0011752 A1 | 1/2007 | Paleyanda |
| 2007/0042462 A1 | 2/2007 | Hildinger |
| 2007/0065938 A1 | 3/2007 | Gronthos et al. |
| 2007/0105222 A1 | 5/2007 | Wolfinbarger et al. |
| 2007/0116612 A1 | 5/2007 | Williamson |
| 2007/0117180 A1 | 5/2007 | Morikawa et al. |
| 2007/0122904 A1 | 5/2007 | Nordon |
| 2007/0123996 A1 | 5/2007 | Sugaya et al. |
| 2007/0160583 A1 | 7/2007 | Lange et al. |
| 2007/0166834 A1 | 7/2007 | Williamson et al. |
| 2007/0178071 A1 | 8/2007 | Westenfelder |
| 2007/0196421 A1 | 8/2007 | Hunter et al. |
| 2007/0197957 A1 | 8/2007 | Hunter et al. |
| 2007/0198063 A1 | 8/2007 | Hunter et al. |
| 2007/0202485 A1 | 8/2007 | Nees et al. |
| 2007/0203330 A1 | 8/2007 | Kretschmar et al. |
| 2007/0208134 A1 | 9/2007 | Hunter et al. |
| 2007/0231305 A1 | 10/2007 | Noll et al. |
| 2007/0258943 A1 | 11/2007 | Penn et al. |
| 2007/0274970 A1 | 11/2007 | Gordon et al. |
| 2007/0275457 A1 | 11/2007 | Granchelli et al. |
| 2007/0295651 A1 | 12/2007 | Martinez et al. |
| 2007/0298015 A1 | 12/2007 | Beer et al. |
| 2007/0298497 A1 | 12/2007 | Antwiler |
| 2008/0003663 A1 | 1/2008 | Bryhan et al. |
| 2008/0009458 A1 | 1/2008 | Dornan et al. |
| 2008/0032398 A1 | 2/2008 | Cannon et al. |
| 2008/0050770 A1 | 2/2008 | Zhang et al. |
| 2008/0063600 A1 | 3/2008 | Aguzzi et al. |
| 2008/0064649 A1 | 3/2008 | Rameshwar |
| 2008/0069807 A1 | 3/2008 | Jy et al. |
| 2008/0095676 A1 | 4/2008 | Andretta |
| 2008/0095690 A1 | 4/2008 | Liu |
| 2008/0103412 A1 | 5/2008 | Chin |
| 2008/0110827 A1 | 5/2008 | Cote et al. |
| 2008/0113426 A1 | 5/2008 | Smith et al. |
| 2008/0113440 A1 | 5/2008 | Gurney et al. |
| 2008/0153077 A1 | 6/2008 | Henry |
| 2008/0160597 A1 | 7/2008 | van der Heiden et al. |
| 2008/0166808 A1 | 7/2008 | Nyberg |
| 2008/0181879 A1 | 7/2008 | Catelas et al. |
| 2008/0190857 A1 | 8/2008 | Beretta et al. |
| 2008/0194017 A1 | 8/2008 | Esser et al. |
| 2008/0206831 A1 | 8/2008 | Coffey et al. |
| 2008/0220522 A1 | 9/2008 | Antwiler |
| 2008/0220523 A1 | 9/2008 | Antwiler |
| 2008/0220524 A1 | 9/2008 | Noll et al. |
| 2008/0220526 A1 | 9/2008 | Ellison et al. |
| 2008/0221443 A1 | 9/2008 | Ritchie et al. |
| 2008/0227189 A1 | 9/2008 | Bader |
| 2008/0227190 A1 | 9/2008 | Antwiler |
| 2008/0248572 A1 | 10/2008 | Antwiler |
| 2008/0254533 A1 | 10/2008 | Antwiler |
| 2008/0268165 A1 | 10/2008 | Fekety et al. |
| 2008/0306095 A1 | 12/2008 | Crawford |

(56) References Cited

U.S. PATENT DOCUMENTS

| | | |
|---|---|---|
| 2009/0004738 A1 | 1/2009 | Merchav et al. |
| 2009/0011399 A1 | 1/2009 | Fischer |
| 2009/0047289 A1 | 2/2009 | Denhardt et al. |
| 2009/0074728 A1 | 3/2009 | Gronthos et al. |
| 2009/0075881 A1 | 3/2009 | Catelas et al. |
| 2009/0076481 A1 | 3/2009 | Stegmann et al. |
| 2009/0081770 A1 | 3/2009 | Srienc et al. |
| 2009/0081797 A1 | 3/2009 | Fadeev et al. |
| 2009/0092608 A1 | 4/2009 | Ni et al. |
| 2009/0098103 A1 | 4/2009 | Madison et al. |
| 2009/0098645 A1 | 4/2009 | Fang et al. |
| 2009/0100944 A1 | 4/2009 | Newby |
| 2009/0104163 A1 | 4/2009 | Deans et al. |
| 2009/0104692 A1 | 4/2009 | Bartfeld et al. |
| 2009/0104699 A1 | 4/2009 | Newby et al. |
| 2009/0118161 A1 | 5/2009 | Cruz |
| 2009/0181087 A1 | 7/2009 | Kraus et al. |
| 2009/0183581 A1 | 7/2009 | Wilkinson et al. |
| 2009/0191627 A1 | 7/2009 | Fadeev et al. |
| 2009/0191632 A1 | 7/2009 | Fadeev et al. |
| 2009/0191634 A1 | 7/2009 | Martin et al. |
| 2009/0203065 A1 | 8/2009 | Gehman et al. |
| 2009/0203129 A1 | 8/2009 | Furcht et al. |
| 2009/0203130 A1 | 8/2009 | Furcht et al. |
| 2009/0214382 A1 | 8/2009 | Burgess et al. |
| 2009/0214481 A1 | 8/2009 | Muhs et al. |
| 2009/0214652 A1 | 8/2009 | Hunter et al. |
| 2009/0215022 A1 | 8/2009 | Page et al. |
| 2009/0227024 A1 | 9/2009 | Baker et al. |
| 2009/0227027 A1 | 9/2009 | Baker et al. |
| 2009/0233334 A1 | 9/2009 | Hildinger et al. |
| 2009/0233353 A1 | 9/2009 | Furcht et al. |
| 2009/0233354 A1 | 9/2009 | Furcht et al. |
| 2009/0258379 A1 | 10/2009 | Klein et al. |
| 2009/0269841 A1 | 10/2009 | Wojciechowski et al. |
| 2009/0270725 A1 | 10/2009 | Leimbach et al. |
| 2009/0280153 A1 | 11/2009 | Hunter et al. |
| 2009/0280565 A1 | 11/2009 | Jolicoeur et al. |
| 2009/0291890 A1 | 11/2009 | Madison et al. |
| 2010/0009409 A1 | 1/2010 | Hubbell et al. |
| 2010/0021954 A1 | 1/2010 | Deshayes et al. |
| 2010/0021990 A1 | 1/2010 | Edwards et al. |
| 2010/0028311 A1 | 2/2010 | Motlagh et al. |
| 2010/0042260 A1 | 2/2010 | Antwiler |
| 2010/0075410 A1 | 3/2010 | Desai et al. |
| 2010/0086481 A1 | 4/2010 | Baird et al. |
| 2010/0092536 A1 | 4/2010 | Hunter et al. |
| 2010/0093607 A1 | 4/2010 | Dickneite |
| 2010/0105138 A1 | 4/2010 | Dodd et al. |
| 2010/0111910 A1 | 5/2010 | Rakoczy |
| 2010/0129376 A1 | 5/2010 | Denhardt et al. |
| 2010/0129912 A1 | 5/2010 | Su et al. |
| 2010/0136091 A1 | 6/2010 | Moghe et al. |
| 2010/0144037 A1 | 6/2010 | Antwiler |
| 2010/0144634 A1 | 6/2010 | Zheng et al. |
| 2010/0183561 A1 | 7/2010 | Sakthivel et al. |
| 2010/0183585 A1 | 7/2010 | Van Zant et al. |
| 2010/0203020 A1 | 8/2010 | Ghosh |
| 2010/0230203 A1 | 9/2010 | Karayianni |
| 2010/0248366 A1 | 9/2010 | Fadeev et al. |
| 2010/0278933 A1 | 11/2010 | Sayeski et al. |
| 2010/0285453 A1 | 11/2010 | Goodrich |
| 2010/0285590 A1 | 11/2010 | Verfaillie et al. |
| 2010/0291180 A1 | 11/2010 | Uhrich |
| 2010/0291181 A1 | 11/2010 | Uhrich et al. |
| 2010/0297234 A1 | 11/2010 | Sugino et al. |
| 2010/0304427 A1 | 12/2010 | Faris et al. |
| 2010/0304482 A1 | 12/2010 | Deshayes et al. |
| 2010/0310524 A1 | 12/2010 | Bechor et al. |
| 2010/0316446 A1 | 12/2010 | Runyon |
| 2011/0085746 A1 | 4/2011 | Wong et al. |
| 2011/0111498 A1 | 5/2011 | Oh et al. |
| 2011/0129447 A1 | 6/2011 | Meretzki et al. |
| 2011/0129486 A1 | 6/2011 | Meiron |
| 2011/0143433 A1 | 6/2011 | Oh et al. |
| 2011/0159584 A1 | 6/2011 | Gibbons et al. |
| 2011/0171182 A1 | 7/2011 | Abelman |
| 2011/0171659 A1 | 7/2011 | Furcht et al. |
| 2011/0177595 A1 | 7/2011 | Furcht et al. |
| 2011/0212493 A1 | 9/2011 | Hirschel et al. |
| 2011/0256108 A1 | 10/2011 | Meiron et al. |
| 2011/0256160 A1 | 10/2011 | Meiron et al. |
| 2011/0293583 A1 | 12/2011 | Aberman |
| 2012/0028352 A1 | 2/2012 | Oh et al. |
| 2012/0051976 A1 | 3/2012 | Lu et al. |
| 2012/0058554 A1 | 3/2012 | Deshayes et al. |
| 2012/0064047 A1 | 3/2012 | Verfaillie et al. |
| 2012/0064583 A1 | 3/2012 | Edwards et al. |
| 2012/0086657 A1 | 4/2012 | Stanton, IV et al. |
| 2012/0118919 A1 | 5/2012 | Cianciolo |
| 2012/0122220 A1 | 5/2012 | Merchav et al. |
| 2012/0135043 A1 | 5/2012 | Maziarz et al. |
| 2012/0145580 A1 | 6/2012 | Paruit et al. |
| 2012/0156779 A1 | 6/2012 | Anneren et al. |
| 2012/0178885 A1 | 7/2012 | Kohn et al. |
| 2012/0189713 A1 | 7/2012 | Kohn et al. |
| 2012/0208039 A1 | 8/2012 | Barbaroux et al. |
| 2012/0219531 A1 | 8/2012 | Oh et al. |
| 2012/0219737 A1 | 8/2012 | Sugino et al. |
| 2012/0226013 A1 | 9/2012 | Kohn et al. |
| 2012/0231519 A1 | 9/2012 | Bushman et al. |
| 2012/0237557 A1 | 9/2012 | Lewitus et al. |
| 2012/0295352 A1 | 11/2012 | Antwiler |
| 2012/0308531 A1 | 12/2012 | Pinxteren et al. |
| 2012/0315696 A1 | 12/2012 | Luitjens et al. |
| 2013/0004465 A1 | 1/2013 | Aberman |
| 2013/0039892 A1 | 2/2013 | Aberman |
| 2013/0058907 A1 | 3/2013 | Wojciechowski et al. |
| 2013/0059383 A1 | 3/2013 | Dijkhuizen Borgart et al. |
| 2013/0101561 A1 | 4/2013 | Sabaawy |
| 2013/0143313 A1 | 6/2013 | Niazi |
| 2013/0157353 A1 | 6/2013 | Dijkhuizen Borgart et al. |
| 2013/0259843 A1 | 10/2013 | Duda et al. |
| 2013/0319575 A1 | 12/2013 | Mendyk |
| 2013/0323213 A1 | 12/2013 | Meiron et al. |
| 2013/0337558 A1 | 12/2013 | Meiron et al. |
| 2014/0004553 A1 | 1/2014 | Parker et al. |
| 2014/0017209 A1 | 1/2014 | Aberman et al. |
| 2014/0030805 A1 | 1/2014 | Kasuto et al. |
| 2014/0051162 A1 | 2/2014 | Nankervis |
| 2014/0051167 A1 | 2/2014 | Nankervis et al. |
| 2014/0112893 A1 | 4/2014 | Tom et al. |
| 2014/0186937 A1 | 7/2014 | Smith et al. |
| 2014/0193895 A1 | 7/2014 | Smith et al. |
| 2014/0193911 A1 | 7/2014 | Newby et al. |
| 2014/0242039 A1 | 8/2014 | Meiron et al. |
| 2014/0248244 A1 | 9/2014 | Danilkovitch et al. |
| 2014/0315300 A1 | 10/2014 | Oh et al. |
| 2014/0342448 A1 | 11/2014 | Nagels |
| 2015/0004693 A1 | 1/2015 | Danilkovitch et al. |
| 2015/0104431 A1 | 4/2015 | Pittenger et al. |
| 2015/0111252 A1 | 4/2015 | Hirschel et al. |
| 2015/0125138 A1 | 5/2015 | Karnieli et al. |
| 2015/0175950 A1 | 6/2015 | Hirschel et al. |
| 2015/0225685 A1 | 8/2015 | Hirschel et al. |
| 2015/0247122 A1 | 9/2015 | Tom et al. |
| 2015/0259749 A1 | 9/2015 | Santos et al. |
| 2016/0362650 A1 | 12/2016 | Wojciechowski et al. |
| 2016/0362652 A1 | 12/2016 | Page et al. |
| 2018/0010082 A1 | 1/2018 | Jacques et al. |
| 2018/0030398 A1 | 2/2018 | Castillo |
| 2018/0155668 A1 | 6/2018 | Hirschel et al. |
| 2019/0194628 A1 | 6/2019 | Rao et al. |

FOREIGN PATENT DOCUMENTS

| | | |
|---|---|---|
| DE | 3833925 | 9/1989 |
| DE | 4007703 A1 | 9/1991 |
| DE | 10244859 A1 | 4/2004 |
| DE | 10327988 A1 | 7/2004 |
| DE | 102012200939 A1 | 7/2013 |
| EP | 0220650 A2 | 5/1987 |
| EP | 750938 A1 | 1/1997 |
| EP | 906415 A1 | 4/1999 |

(56) References Cited

FOREIGN PATENT DOCUMENTS

| | | |
|---|---|---|
| EP | 959980 A1 | 12/1999 |
| EP | 1007631 A1 | 6/2000 |
| EP | 1028737 A1 | 8/2000 |
| EP | 1028991 A1 | 8/2000 |
| EP | 1066052 A2 | 1/2001 |
| EP | 1066060 A2 | 1/2001 |
| EP | 1084230 A2 | 3/2001 |
| EP | 1147176 A1 | 10/2001 |
| EP | 1220611 A1 | 7/2002 |
| EP | 1223956 A1 | 7/2002 |
| EP | 1325953 A1 | 7/2003 |
| EP | 1437404 A1 | 7/2004 |
| EP | 1437406 A2 | 7/2004 |
| EP | 1447443 A1 | 8/2004 |
| EP | 1452594 A1 | 9/2004 |
| EP | 1062321 B1 | 12/2004 |
| EP | 1484080 A1 | 12/2004 |
| EP | 1498478 A1 | 1/2005 |
| EP | 1036057 B1 | 10/2005 |
| EP | 1605044 A2 | 12/2005 |
| EP | 1756262 A1 | 2/2007 |
| EP | 1771737 A1 | 4/2007 |
| EP | 1882030 A1 | 1/2008 |
| EP | 1908490 A1 | 4/2008 |
| EP | 1971679 A2 | 9/2008 |
| EP | 1991668 A2 | 11/2008 |
| EP | 2027247 A2 | 2/2009 |
| EP | 2200622 A1 | 6/2010 |
| EP | 2208782 A2 | 7/2010 |
| EP | 2264145 A1 | 12/2010 |
| EP | 2027247 B1 | 1/2011 |
| EP | 2303293 A1 | 4/2011 |
| EP | 2311938 A1 | 4/2011 |
| EP | 2331957 A1 | 6/2011 |
| EP | 2334310 A2 | 6/2011 |
| EP | 2334783 A2 | 6/2011 |
| EP | 2361968 A1 | 8/2011 |
| EP | 2366775 A1 | 9/2011 |
| EP | 2465922 A2 | 6/2012 |
| EP | 2481819 | 8/2012 |
| EP | 2548951 A1 | 1/2013 |
| EP | 2561066 A1 | 2/2013 |
| EP | 2575831 A1 | 4/2013 |
| EP | 2591789 A2 | 5/2013 |
| EP | 2624845 A2 | 8/2013 |
| EP | 2626417 A1 | 8/2013 |
| EP | 2641606 A1 | 9/2013 |
| EP | 2689008 A1 | 1/2014 |
| EP | 2694639 A1 | 2/2014 |
| EP | 2697362 A2 | 2/2014 |
| EP | 2739720 A1 | 6/2014 |
| EP | 2807246 A1 | 12/2014 |
| EP | 1758985 | 6/2015 |
| GB | 1414671 A | 11/1975 |
| GB | 2297980 A | 8/1996 |
| GB | 2360789 A | 10/2001 |
| HU | 3285 U | 5/2007 |
| JP | H02245177 A | 9/1990 |
| JP | 2003/052360 A | 2/2003 |
| JP | 2003510068 A | 3/2003 |
| JP | 2005278564 A | 10/2005 |
| JP | 2007000038 A | 1/2007 |
| JP | 2012-506257 | 3/2012 |
| JP | 5548207 | 7/2014 |
| JP | 2019-516029 | 6/2019 |
| JP | 2019-525765 | 9/2019 |
| KR | 101228026 | 1/2013 |
| KR | 10-2015-0002762 | 1/2015 |
| KR | 101504392 | 3/2015 |
| KR | 101548790 | 8/2015 |
| KR | 101553040 | 9/2015 |
| KR | 10-2017-0076679 | 7/2017 |
| KR | 10-2018-0027501 | 3/2018 |
| KR | 102027596 | 10/2019 |
| KR | 10-2020-0034790 | 3/2020 |
| KR | 10-2020-0058433 | 5/2020 |
| MY | 115206 A | 4/2003 |
| WO | 86/02379 A1 | 4/1986 |
| WO | 88/01643 A1 | 3/1988 |
| WO | WO 89/12676 | 12/1989 |
| WO | 90/02171 A1 | 3/1990 |
| WO | WO-9013306 A2 | 11/1990 |
| WO | WO-9105238 A1 | 4/1991 |
| WO | 91/07485 A1 | 5/1991 |
| WO | WO-9106641 A1 | 5/1991 |
| WO | WO-9109194 A1 | 6/1991 |
| WO | 92/10564 A1 | 6/1992 |
| WO | WO-94/25571 A1 | 11/1994 |
| WO | 95/04813 A1 | 2/1995 |
| WO | 95/21911 A1 | 8/1995 |
| WO | WO 95/24468 | 9/1995 |
| WO | WO-96/29395 A1 | 9/1996 |
| WO | WO-96/39035 A1 | 12/1996 |
| WO | WO-97/05826 A1 | 2/1997 |
| WO | 97/16527 A1 | 5/1997 |
| WO | WO-97/29792 A1 | 8/1997 |
| WO | 1997-040137 A1 | 10/1997 |
| WO | WO-97/39104 A1 | 10/1997 |
| WO | WO-1997-040137 A1 | 10/1997 |
| WO | WO 98/22588 | 5/1998 |
| WO | WO-98/31403 A1 | 7/1998 |
| WO | 98/53046 A1 | 11/1998 |
| WO | WO-98/51317 A1 | 11/1998 |
| WO | WO-98/51785 A1 | 11/1998 |
| WO | WO-99/05180 A1 | 2/1999 |
| WO | WO-99/24391 A1 | 5/1999 |
| WO | WO-99/24490 A1 | 5/1999 |
| WO | WO-99/27167 A1 | 6/1999 |
| WO | WO-99/49015 A2 | 9/1999 |
| WO | WO-00/06704 A2 | 2/2000 |
| WO | WO-0009018 A1 | 2/2000 |
| WO | WO-00/16420 A1 | 3/2000 |
| WO | WO-00/17326 A1 | 3/2000 |
| WO | WO-00/29002 A2 | 5/2000 |
| WO | WO-0032225 A1 | 6/2000 |
| WO | WO-00/44058 A2 | 7/2000 |
| WO | WO 00/46354 | 8/2000 |
| WO | WO-0054651 A2 | 9/2000 |
| WO | WO-0056405 A2 | 9/2000 |
| WO | WO-00/59933 A2 | 10/2000 |
| WO | WO-00/69449 A2 | 11/2000 |
| WO | 00/75275 A2 | 12/2000 |
| WO | WO-00/75196 A1 | 12/2000 |
| WO | WO-00/77236 A2 | 12/2000 |
| WO | WO-2001/000783 A2 | 1/2001 |
| WO | WO-2001/011011 A2 | 2/2001 |
| WO | WO-2001/018174 A2 | 3/2001 |
| WO | WO-2001/021766 A2 | 3/2001 |
| WO | 01/23520 A1 | 4/2001 |
| WO | WO-2001/025402 A1 | 4/2001 |
| WO | WO-2001/029189 A2 | 4/2001 |
| WO | WO-0122810 A2 | 4/2001 |
| WO | WO-2001/034167 A1 | 5/2001 |
| WO | WO-2001/049851 A1 | 7/2001 |
| WO | WO-2001/054706 A2 | 8/2001 |
| WO | 2001-094541 A2 | 12/2001 |
| WO | WO-2001-094541 A2 | 12/2001 |
| WO | 02/28996 A1 | 4/2002 |
| WO | WO-2002/042422 A2 | 5/2002 |
| WO | WO-2002/057430 A2 | 7/2002 |
| WO | WO-2002/092794 A2 | 11/2002 |
| WO | WO-2002/101385 A2 | 12/2002 |
| WO | WO-2003/010303 A1 | 2/2003 |
| WO | WO-2003/014313 A2 | 2/2003 |
| WO | WO-2003/016916 A1 | 2/2003 |
| WO | WO-2003/023018 A2 | 3/2003 |
| WO | WO-2003/023019 A1 | 3/2003 |
| WO | WO-2003/025167 A2 | 3/2003 |
| WO | WO-2003/029402 A2 | 4/2003 |
| WO | WO 03/039459 | 5/2003 |
| WO | WO-2003/040336 A2 | 5/2003 |
| WO | WO-2003/042405 A2 | 5/2003 |
| WO | WO-2003/046161 A2 | 6/2003 |
| WO | WO-2003/055989 A2 | 7/2003 |

(56) References Cited

FOREIGN PATENT DOCUMENTS

| | | |
|---|---|---|
| WO | WO-2003/061685 A1 | 7/2003 |
| WO | WO-2003/061686 A1 | 8/2003 |
| WO | WO-2003/068961 A2 | 9/2003 |
| WO | WO-2003/072064 A2 | 9/2003 |
| WO | WO-2003/078609 A1 | 9/2003 |
| WO | WO-2003/078967 A2 | 10/2003 |
| WO | WO-2003/080816 A2 | 10/2003 |
| WO | WO-2003/082145 A2 | 10/2003 |
| WO | WO-2003/085099 A2 | 10/2003 |
| WO | WO-2003/089631 A1 | 10/2003 |
| WO | WO-2003/091398 A2 | 11/2003 |
| WO | WO-2003/095631 A1 | 11/2003 |
| WO | 03/105663 A2 | 12/2003 |
| WO | WO-2004/001697 A1 | 12/2003 |
| WO | WO-2004/012226 A2 | 2/2004 |
| WO | WO-2004/016779 A1 | 2/2004 |
| WO | WO-2004/018526 A1 | 3/2004 |
| WO | WO-2004/018655 A2 | 3/2004 |
| WO | WO-2004/026115 A2 | 4/2004 |
| WO | WO-2004/029231 A1 | 4/2004 |
| WO | WO-2004/042023 A2 | 5/2004 |
| WO | WO-2004/042033 A2 | 5/2004 |
| WO | WO-2004/042040 A1 | 5/2004 |
| WO | WO-2004/044127 A2 | 5/2004 |
| WO | WO-2004/044158 A2 | 5/2004 |
| WO | WO-2004/046304 A1 | 6/2004 |
| WO | WO-2004/050826 A2 | 6/2004 |
| WO | WO-2004/053096 A2 | 6/2004 |
| WO | WO-2004/055155 A2 | 7/2004 |
| WO | WO-2004/056186 A1 | 7/2004 |
| WO | WO-2004/065616 A2 | 8/2004 |
| WO | WO-2004/069172 A2 | 8/2004 |
| WO | WO-2004/070013 A2 | 8/2004 |
| WO | WO-2004/072264 A2 | 8/2004 |
| WO | WO-2004/073633 A2 | 9/2004 |
| WO | WO-2004/074464 A1 | 9/2004 |
| WO | WO-2004/076642 A2 | 9/2004 |
| WO | WO-2004/076653 A1 | 9/2004 |
| WO | 2004/090112 A2 | 10/2004 |
| WO | WO-2004/087870 A2 | 10/2004 |
| WO | WO-2004/094588 A2 | 11/2004 |
| WO | WO-2004/096975 A2 | 11/2004 |
| WO | WO-2004/104166 A2 | 12/2004 |
| WO | WO-2004/106499 A1 | 12/2004 |
| WO | WO-2004/113513 A2 | 12/2004 |
| WO | WO-2005/001033 A2 | 1/2005 |
| WO | WO-2005/001081 A1 | 1/2005 |
| WO | WO-2005/003320 A2 | 1/2005 |
| WO | WO-2005/007799 A2 | 1/2005 |
| WO | WO-2005/010172 A2 | 2/2005 |
| WO | WO-2005/011524 A1 | 2/2005 |
| WO | WO-2005/012480 A2 | 2/2005 |
| WO | WO-2005/012510 A1 | 2/2005 |
| WO | WO-2005/012512 A1 | 2/2005 |
| WO | WO-05014775 A2 | 2/2005 |
| WO | WO-2005/028433 A2 | 3/2005 |
| WO | WO-05044972 A2 | 5/2005 |
| WO | WO-2005/056747 A2 | 6/2005 |
| WO | WO-05051316 A2 | 6/2005 |
| WO | WO-2005/063303 A1 | 7/2005 |
| WO | WO-2005/075636 A1 | 8/2005 |
| WO | 2005087915 A2 | 9/2005 |
| WO | WO 2005/104755 | 11/2005 |
| WO | WO-2005/107760 A1 | 11/2005 |
| WO | WO-2006/009291 A1 | 1/2006 |
| WO | WO-2006/032075 A1 | 3/2006 |
| WO | WO-2006/032092 A1 | 3/2006 |
| WO | WO 2006/037022 | 4/2006 |
| WO | WO-2006/108229 A1 | 10/2006 |
| WO | WO-2006/113881 A2 | 10/2006 |
| WO | WO-2006/121445 A2 | 11/2006 |
| WO | WO-06124021 A1 | 11/2006 |
| WO | WO-06129312 A2 | 12/2006 |
| WO | WO 2007/038572 | 4/2007 |
| WO | WO 2007/059473 | 5/2007 |
| WO | WO-2007/115367 A1 | 10/2007 |
| WO | WO-2007/115368 A1 | 10/2007 |
| WO | WO 2007/117765 | 10/2007 |
| WO | 2007/136821 A1 | 11/2007 |
| WO | 2007/139742 A1 | 12/2007 |
| WO | 2007/139746 A1 | 12/2007 |
| WO | 2007/139747 A1 | 12/2007 |
| WO | 2007/139748 A2 | 12/2007 |
| WO | WO-2008/006168 A1 | 1/2008 |
| WO | WO-2008/011664 A1 | 1/2008 |
| WO | WO-2008/017128 A1 | 2/2008 |
| WO | WO-2008/028241 A1 | 3/2008 |
| WO | WO-08040812 A1 | 4/2008 |
| WO | WO 2008/073635 | 6/2008 |
| WO | 2008/109674 A2 | 9/2008 |
| WO | WO-2008/116261 A1 | 10/2008 |
| WO | WO-2008/149129 A1 | 12/2008 |
| WO | 2009/034186 A2 | 3/2009 |
| WO | WO-2009/026635 A1 | 3/2009 |
| WO | WO-09058146 A1 | 5/2009 |
| WO | WO-09080054 A1 | 7/2009 |
| WO | WO-09081408 A2 | 7/2009 |
| WO | WO-2009/140452 A2 | 11/2009 |
| WO | WO-09132457 A1 | 11/2009 |
| WO | WO-2009/144720 A1 | 12/2009 |
| WO | WO-10005527 A1 | 1/2010 |
| WO | WO-2010/019886 A1 | 2/2010 |
| WO | WO-10014253 A2 | 2/2010 |
| WO | WO-10019997 A1 | 2/2010 |
| WO | WO-2010/026573 A1 | 3/2010 |
| WO | WO-2010/026574 A2 | 3/2010 |
| WO | WO-2010/026575 A2 | 3/2010 |
| WO | WO 2010/036760 | 4/2010 |
| WO | WO-2010/036760 A1 | 4/2010 |
| WO | WO-2010/059487 A1 | 5/2010 |
| WO | WO-10061377 A2 | 6/2010 |
| WO | WO-10068710 A2 | 6/2010 |
| WO | WO-10071826 A2 | 6/2010 |
| WO | WO-10083385 A2 | 7/2010 |
| WO | WO-10111255 A1 | 9/2010 |
| WO | WO-10119036 A1 | 10/2010 |
| WO | WO-10123594 A2 | 10/2010 |
| WO | WO-2011/025445 A1 | 3/2011 |
| WO | WO 2011/098592 | 8/2011 |
| WO | WO 2011/130617 | 10/2011 |
| WO | WO-2011/132087 A1 | 10/2011 |
| WO | WO-2011/147967 A1 | 12/2011 |
| WO | WO-2012/072924 A1 | 6/2012 |
| WO | WO-2012/127320 A1 | 9/2012 |
| WO | WO-2012/138968 A1 | 10/2012 |
| WO | WO-2012/140519 A2 | 10/2012 |
| WO | 2012/171026 A2 | 12/2012 |
| WO | 2012/171030 A2 | 12/2012 |
| WO | WO-2012/171026 A2 | 12/2012 |
| WO | WO-2012/171030 A2 | 12/2012 |
| WO | WO 2013/085682 | 6/2013 |
| WO | WO-2013/110651 A1 | 8/2013 |
| WO | WO-2014/037862 A1 | 3/2014 |
| WO | WO-2014/037863 A1 | 3/2014 |
| WO | WO-2014/068508 A2 | 5/2014 |
| WO | WO-2014/128306 A1 | 8/2014 |
| WO | WO-2014/128634 A1 | 8/2014 |
| WO | WO-2014/131846 A1 | 9/2014 |
| WO | WO-2014/141111 A1 | 9/2014 |
| WO | WO-2015/004609 A2 | 1/2015 |
| WO | WO 2015/059714 | 4/2015 |
| WO | 2015/073913 A1 | 5/2015 |
| WO | WO 2015/069943 | 5/2015 |
| WO | WO 2015/118148 | 8/2015 |
| WO | WO 2015/118149 | 8/2015 |
| WO | WO-2015/131143 A1 | 9/2015 |
| WO | WO 2016/130940 | 8/2016 |
| WO | WO 2017/072201 | 5/2017 |
| WO | WO 2017/158611 | 9/2017 |
| WO | WO 2017/207822 | 12/2017 |
| WO | WO 2018/183426 | 10/2018 |
| WO | WO 2019/155032 | 8/2019 |

(56) References Cited

FOREIGN PATENT DOCUMENTS

| WO | WO 2019/238919 | 12/2019 |
|---|---|---|
| WO | WO 2020/020569 | 1/2020 |
| WO | WO 2020/079274 | 4/2020 |

OTHER PUBLICATIONS

Communication pursuant to Article 94(3) EPC, European Patent Application No. 15718657.8, dated Mar. 22, 2018.
First Office Action, Chinese Patent Application No. 201580020869.5, dated Apr. 27, 2018 (English language translation included).
International Search Report and Written Opinion, PCT/US2015/022541, dated Jul. 17, 2015.
Rejection of the Application, Japanese Patent Application No. 2016-558755, dated Feb. 5, 2019 (English language translation included).
Rejection of the Application, Japanese Patent Application No. 2016-558755, dated Jan. 28, 2020 (English language translation included).
Second Office Action, Chinese Patent Application No. 201580020869.5, dated May 21, 2019 (English language translation included).
Third Office Action, Chinese Patent Application No. 201580020869.5, dated Nov. 6, 2019 (English language translation included).
Chang et al., "Membrane Bioreactors: Present and Prospects", Advances in Biochemical Engineering, 1991, pp. 27-64, vol. 44.
Chang, Ho Nam, "Membrane Bioreactors: Engineering Aspects", Biotech. Adv., 1987, pp. 129-145, vol. 5.
Edgington, Stephen M., "New Horizons for Stem-Cell Bioreactors", Biotechnology, Oct. 1992, pp. 1099-1106, vol. 10.
Gastens et al., "Good Manufacturing Practice-Compliant Expansion of Marrow-Derived Stem and Progenitor Cells for Cell Therapy", Cell Transplantation, 2007, pp. 685-696, vol. 16.
Gramer et al., "Screening Tool for Hollow-Fiber Bioreactor Process Development", Biotechnol. Prog., 1998, pp. 203-209, vol. 14.
Hirschel et al., "An Automated Hollow Fiber System for the Large Scale Manufacture of Mammalian Cell Secreted Product", Large Scale Cell Culture Technology, ed. Bjorn K. Lydersen, 1987, pp. 113-144, Hanser Publishers.
Infanger et al., "Simulated weightlessness changes the cytoskeleton and extracellular matrix proteins in papillary thyroid carcinoma cells", Cell and Tissue Research, 2006, 324(2): 267-277.
Jones et al., "Genetic stability of bone marrow-derived human mesenchymal stromal cells in the Quantum System", Cytotherapy, 2013; 15: 1323-1339.
Liu et al., "Ex vivo Expansion of Hematopoietic Stem Cells Derived from Umbilical Cord Blood in Rotating Wall Vessel", Journal of Biotechnology, 2006, 124:592-601.
Nankervis et al., "Shear Stress Conditions in the Quantum Cell Expansion System", Poster Session—TERMIS AM Annual Conference 2013, Nov. 12, 2013.
Nguyen et al., "QUANTUM® Cell Expansion System: Automated Expansion of Human Mesenchymal Stem Cells from Precultured Cells Using the Quantum Cell Expansion System", Terumo BCT, Inc., 2012.
Nielsen, Lars Keld, "Bioreactors for Hematopoietic Cell Culture", Annu. Rev. Biomed. Eng., 1999, vol. 1, pp. 129-152.
Office Action, Chinese Patent Application No. 201580020869.5, dated Apr. 27, 2018. (English language translation included).
Office Action, Chinese Patent Application No. 201580020869.5, dated May 21, 2019. (English language translation included).
Official Communication, European Patent Application No. 15718657.8, dated Jul. 21, 2017.
Official Communication, European Patent Application No. 15718657.8, dated Mar. 22, 2018.
Pörtner et al., "An Overview on Bioreactor Design, Prototyping and Process Control for Reproducible Three-Dimensional Tissue Culture", Drug Testing in Vitro: Breakthroughs and Trends in Cell Culture Technology, ed. Uwe Marx and Volker Sandig, 2007, Wiley-VCH, pp. 53-78.

The Extended European Search Report, European Patent Application No. 19202519.5, dated Nov. 15, 2019.
Zhao et al., "Perfusion Bioreactor System for Human Mesenchymal Stem Cell Tissue Engineering: Dynamic Cell Seeding and Construct Development", Biotechnology and Bioengineering, Aug. 20, 2005, vol. 91, No. 4, pp. 482-493.
"The Effect of Rocking Rate and Angle on T Cell Cultures Grown in XuriTM Cell Expansion Systems," GE Healthcare UK Limited, Cell therapy bioreactor systems, Application note 29-1166-55 AA, Aug. 2014, www.gelifesciences.com/xuri.
Abumiya et al., "Shear Stress Induces Expression of Vascular Endothelial Growth Factor Receptor Flk-1/KDR Through the CT-Rich Sp1 Binding Site," Ateriosclerosis, Thrombosis, and Vascular Biology, vol. 22, Jun. 2002, pp. 907-913.
Akiyama et al., "Ultrathin Poly(N-isopropylacrylamide) Grafted Layer on Polystyrene Surfaces for Cell Adhesion/Detachment Control," Langmuir, vol. 20, No. 13, May 26, 2004, pp. 5506-5511.
Akram et al., "Mesenchymal Stem Cells Promote Alveolar Epithelial Cell Wound Repair in vitro through Distinct Migratory and Paracrine Mechanisms," Respiratory Research, vol. 14, No. 9, 2013, pp. 1-16.
Alenazi et al., "Modified Polyether-sulfone Membrane: a Mini Review," Designed Monomers And Polymers, vol. 20, No. 1, 2017, pp. 532-546.
Anamelechi et al., "Streptavidin Binding and Endothelial Cell Adhesion to Biotinylated Fibronectin," Langmuir, vol. 23, No. 25, Dec. 4, 2007, pp. 12583-12588.
Azar et al., "Heart Rates of Male and Female Sprague-Dawley and Spontaneously Hypertensive Rats Housed Singly or in Groups," Journal of the American Association for Laboratory Animal Science, vol. 50, No. 2, Mar. 2011, pp. 175-184.
Baecher-Allan et al., "CD4+CD25high Regulatory Cells in Human Peripheral Blood," The Journal of Immunology, vol. 167, 2001, pp. 1245-1253.
Bai et al., "Expansion of Primitive Human Hematopoietic Stem Cells by Culture in a Zwitterionic Hydrogel," Nature Medicine, vol. 25, Oct. 2019, pp. 1566-1575.
Barker et al., "CD34+ Cell Content of 126 341 Cord Blood Units in the US Inventory: Implications for Transplantation and Banking," Blood Advances, vol. 3, No. 8, Apr. 23, 2019, pp. 1267-1271.
Boitano et al., "Aryl Hydrocarbon Receptor Antagonists Promote the Expansion of Human Hematopoietic Stem Cells," Science, vol. 329, No. 5997, published Sep. 10, 2010. corrected May 6, 2011, pp. 1345-1348.
Brunstein et al., "Infusion of ex vivo Expanded T Regulatory Cells in Adults Transplanted with Umbilical Cord Blood: Safety Profile and Detection Kinetics," Blood, vol. 117, No. 3, Jan. 20, 2011, pp. 1061-1070.
Bryce et al., "In vitro Micronucleus Assay Scored by Flow Cytometry Provides a Comprehensive Evaluation of Cytogenetic Damage and Cytotoxicity," Mutation Research, vol. 630, Mar. 19, 2007, pp. 78-91.
Bryce et al., "Interlaboratory Evaluation of a Flow Cytometric, High Content in vitro Micronucleus Assay," Mutation Research, vol. 650, Jan. 7, 2008, pp. 181-195.
Camacho Villa et al., "CD133+CD34+ and CD133+CD38+ Blood Progenitor Cells as Predictors of Platelet Engraftment in Patients Undergoing Autologous Peripheral Blood Stem Cell Transplantation," Transfusion and Apheresis Science, vol. 46, 2012, pp. 239-244.
Cano et al., "Immobilization of endo-1,4-β-xylanase on Polysulfone Acrylate Membranes: Synthesis and Characterization," Journal of Membrane Science, vol. 280, Feb. 28, 2006, pp. 383-388.
Carvell et al., "Monitoring Live Biomass in Disposable Bioreactors," BioProcess International, vol. 14, No. 3, Mar. 2016, pp. 40-48.
Carvell et al., "On-line Measurements and Control of Viable Cell Density in Cell Culture Manufacturing Processes Using Radio Frequency Impedance," Cytotechnology, 2006, vol. 50, pp. 35-48.
Cuchiara et al., "Covalent immobilization of SCF and SDF1α for in vitro Culture of Hematopoietic Progenitor Cells," Acta Biomaterials, vol. 9, No. 12, Dec. 2013, pp. 9258-9269.

(56) References Cited

OTHER PUBLICATIONS

Da Silva et al., "Smart Thermoresponsive Coatings and Surfaces for Tissue Engineering: Switching Cell-Material Boundaries," Trends in Biotechnology, vol. 15, No. 12, 2007, pp. 577-583.
Garlie et al., "T Cells Coactivated with Immobilized Anti-CD3 and Anti-CD28 as Potential Immunotherapy for Cancer," Journal of immunotherapy, vol. 22, No. 4, 1999, pp. 336-345.
Gloeckner et al., "New Miniaturized Hollow-Fiber Bioreactor for in Vivo Like Cell Culture, Cell Expansion, and Production of Cell-Derived Products," Biotechnology Progress, vol. 17, Aug. 21, 2001, pp. 828-831.
Hao et al., "A Functional Comparison of CD34+ CD38-Cells in Cord Blood and Bone Marrow," Blood, vol. 86, No. 10, Nov. 15, 1995, pp. 3745-3753.
Harimoto et al., "Novel Approach for Achieving Double-Layered Cell Sheets Co-Culture: Overlaying Endothelial Cell Sheets onto Monolayer Hepatocytes Utilizing Temperature-Responsive Culture Dishes," Journal of Biomedical Material Research, vol. 62, 2002, pp. 464-470.
Högstedt et al., "Frequency and Size Distribution of Micronuclei in Lymphocytes Stimulated with Phytohemagglutinin and Pokeweed Mitogen in Workers Exposed to Piperazine," Hereditas, vol. 109, 1998, pp. 139-142.
Horwitz et al., "Phase I/II Study of Stem-Cell Transplantation Using a Single Cord Blood Unit Expanded Ex Vivo with Nicotinamide," Journal of Clinical Oncology, vol. 37, No. 5, Dec. 4, 2018, pp. 367-376.
Itkin et al., "SDF-1 Keeps HSC Quiescent at Home," Blood, vol. 117, No. 2, Jan. 13, 2011, pp. 373-374.
Jang et al., "Syndecan-4 Proteoliposomes Enhance Fibroblast Growth Factor-2 (FGF-2)-Induced Proliferation, Migration, and Neovascularization of Ischemic Muscle," PNAS, vol. 109, No. 5, Jan. 31, 2012, pp. 1679-1684.
Johansson et al., "Pancreatic Islet Survival and Engraftment Is Promoted by Culture on Functionalized Spider Silk Matrices," PLoS ONE, Jun. 19, 2015, pp. 1-21.
Klein et al., "Affinity Membranes Prepared from Hydrophilic Coatings on Microporous Polysulfone Hollow Fibers," Journal of Membrane Science, vol. 90, 1994, pp. 69-80.
Koestenbauer et al., "Protocols for Hematopoietic Stem Cell Expansion from Umbilical Cord Blood," Cell Transplantation, vol. 18, May 6, 2009, pp. 1059-1068.
Koller et al., "Clinical-scale Human Umbilical Cord Blood Cell Expansion in a Novel Automated Perfusion Culture System," Bone Marrow Transplantation, vol. 21, 1998, pp. 653-663.
Lang et al., "Generation of Hematopoietic Humanized Mice in the Newborn BALB/C-Rag2null Il2rγnull Mouse Model: A Multivariable Optimization Approach," Clinical Immunology, vol. 140, Apr. 14, 2011, pp. 102-116.
Lataillade et al., "Chemokine SDF-1 Enhances Circulating CD341 Cell Proliferation in Synergy with Cytokines: Possible Role in Progenitor Survival," Blood, vol. 95, No. 3, Feb. 1, 2000, pp. 756-768.
Lee et al., "Long-Term Outcomes Following CD19 CAR T Cell Therapy for B-ALL Are Superior in Patients Receiving a Fludarabine/Cyclophosphamide Preparative Regimen and Post-CAR Hematopoietic Stem Cell Transplantation," Blood, vol. 128, No. 22, Dec. 2, 2016, Ab. 218.
Li et al., "Heparin-induced Conformation Changes of Fibronectin within the Extracellular Matrix Promote hMSC Osteogenic Differentiation," Biomaterials Science, vol. 3, 2015, pp. 73-84.
Malin et al., "Noninvasive Prediction of Glucose by Near-Infrared Diffuse Reflectance Spectroscopy," Clinical Chemistry, vol. 45, No. 9, 1999, pp. 1651-1658.
Marek-Trzonkowska et al., "Administration of CD4+ CD25high CD127-Regulatory T Cells Preserves β-Cell Function in Type 1 Diabetes in Children," Diabetes Care, vol. 35, No. 9, Sep. 2012, pp. 1817-1820.
Murugappan et al., "Human Hematopoietic Progenitor Cells Grow Faster under Rotational Laminar Flows," Biotechnology Progress—Cell Culture & Tissue Engineering, Online, Apr. 22, 2010.
Nelson et al., "Emergent Patterns of Growth Controlled by Multicellular Form and Mechanics," PNAS, vol. 102, No. 33, Aug. 16, 2005, pp. 11594-11599.
Nicolette et al., "In Vitro Micronucleus Screening of Pharmaceutical Candidates by Flow Cytometry in Chinese Hamster V79 Cells," Environmental and Molecular Mutagenesis, vol. 52, Oct. 20, 2010, pp. 355-362.
Nugent et al., "Adventitial Endothelial Implants Reduce Matrix Metalloproteinase-2 Expression and Increase Luminal Diameter in Porcine Arteriovenous Grafts," Journal of Vascular Surgery, vol. 46, No. 3, Sep. 2007, pp. 548-556.e2.
Okano et al., "Mechanism of Cell Detachment from Temperature-Modulated, Hydrophilic-Hydrophobic Polymer Surfaces," Biomaterials, vol. 16, No. 4, 1995, pp. 297-303.
Putnam et al., "Expansion of Human Regulatory T-Cells from Patients with Type 1 Diabetes," Diabetes, vol. 58, Mar. 2009, pp. 652-662.
Rahmahwati et al., "The Synthesis of Polyethersuifone (PES) Derivatives for the Immobilization of Lipase Enzyme," Key Engineering Materials, vol. 811, Jul. 8, 2019, pp. 14-21.
Rodrigues et al., "Stem Cell Cultivation in Bioreactors," Biotechnology Advances, vol. 29, Jun. 25, 2011, pp. 815-829.
Ronco et al., "Blood and Dialysate Flow Distributions in Hollow-Fiber Hemodialyzers Analyzed by Computerized Helical Scanning Technique," Journal of the American Society of Nephrology, vol. 13, 2002, pp. S53-S61.
Ryu et al., "Near-infrared Light Responsive Synthetic c-di-GMP Module for Optogenetic Applications," ACS Synthetic Biology, vol. 3, Jan. 28, 2014, pp. 802-810.
Shimizu et al., "Fabrication of Pulsatile Cardiac Tissue Grafts Using a Novel 3-Dimensional Cell Sheet Manipulation Technique and Temperature-Responsive Cell Culture Surfaces," Circulation Research, vol. 90, Feb. 22, 2002, e40-e48, pp. 1-9.
Smith et al., "Expansion of Neutrophil Precursors and Progenitors in Suspension Cultures of CD34+ Cells Enriched from Human Bone Marrow," Experimental Hematology, vol. 21, 1993, pp. 870-877.
Streltsova et al., "Recurrent Stimulation of Natural Killer Cell Clones with K562 Expressing Membrane-Bound Interleukin-21 Affects Their Phenotype, Interferon-γ Production, and Lifespan," International Journal of Molecular Sciences, vol. 20, No. 443, 2019, pp. 1-18.
Takezawa et al., "Cell Culture on a Thermo-responsive Polymer Surface," Nature, Bio/Technology, vol. 8, Sep. 1990, pp. 854-856.
Tiziani et al., "Metabolomic Profiling of Drug Response in Acute Myeloid Leukemia Cell lines," PLoS ONE, vol. 4, Issue 1, Jan. 22, 2009, e4251.
Ueda et al., "Interaction of Natural Killer Cells with Neutrophils Exerts a Significant Antitumor Immunity in Hematopoietic Stem Cell Transplantation Recipients," Cancer Medicine, vol. 5, No. 1, 2016 pp. 49-60.
Urbich et al., "Fluid Shear Stress-induced Transcriptional Activation of the Vascular Endothelial Growth Factor Receptor-2 Gene Requires Sp1-Dependent DNA Binding," FEBS Letters, 535, 2003, pp. 87-93.
Von Laer, "Loss of CD38 Antigen on CD34 CD38 Cells during Short-term Culture," Leukemia, Correspondence, 1999 pp. 947-948.
Wagner et al., "Phase I/II Trial of StemRegenin-1 Expanded Umbilical Cord Blood Hematopoietic Stem Cells Supports Testing as a Stand-alone Graft," Cell Stem Cell, Jan. 7, 2016, vol. 18, pp. 144-155.
Weaver et al., "An Analysis of Engraftment Kinetics as a Function of the CD34 Content of the Peripheral Blood Progenitor Cell Collections in 692 Patients after the Administration of Myeloblative Chemotherapy," Blood, vol. 86, No. 10, Nov. 15, 1995, pp. 3691-3969.
Yang et al., "Suspension Culture of Mammalian Cells Using Thermosensitive Microcarrier that Allows Cell Detachment without Proteolytic Enzyme Treatment," Cell Transplantation, vol. 19, Aug. 18, 2010, pp. 1123-1132.

(56) References Cited

OTHER PUBLICATIONS

Yi et al., "A Readily Modified Polyethersuifone with Amino-Substituted Groups: Its Amphiphilic Copolymer Synthesis and Membrane Application," Polymer, vol. 53, Dec. 2, 2011, pp. 350-358.
Zheng et al., "Differential Effects of Cyclic and Static Stretch on Coronary Microvascular Endothelial Cell Receptors and Vasculogenic/Angiogenic Responses," American Journal of Physiology—Heart and Circulatory Physiology, vol. 295, Aug. 2008, H794-H800.
Afzali B, Edozie FC, Fazekasova H, Scotta C, Mitchell PJ, Canavan JB, Kordasti SY, Chana PS, Ellis R, Lord GM, John S, Hilton R, Lechler RI, Lombardi G. Comparison of regulatory T cells in hemodialysis patients and healthy controls: implications for cell therapy in transplantation. Clin J Am Soc Nephrol. 2013;8(8):1396-405.
Alberts B, Johnson A, Lewis J, et al. Molecular Biology of the Cell. 4th edition. New York: Garland Science; 2002. Fibroblasts and Their Transformations: The Connective-Tissue Cell Family. Available from: https://www.ncbi.nlm.nih.gov/books/NBK26889.
Almeida L, Lochner M, Berod L, Sparwasser T. Metabolic pathways in T cell activation and lineage differentiation. Semin Immunol. 2016;28(5):514-524.
Amy Putnam, Todd M. Brusko, Michael R. Lee, Weihong Liu, Gregory L. Szot, Taumoha Ghosh, Mark A. Atkinson, and Jeffrey A. Bluestone. Expansion of human regulatory T-Cells from patients with Type 1 Diabetes. Diabetes, 58: 652-662, 2009.
Anurathapan et al., "Engineered T cells for cancer treatment," Cytotherapy, vol. 16, pp. 713-733, 2014.
Aronowski J, Samways E, Strong R, Rhoades HM, Grotta JC. An alternative method for the quantitation of neuronal damage after experimental middle cerebral artery occlusion in rats: Analysis of behavioral deficit. Journal of cerebral blood flow and metabolism : official journal of the International Society of Cerebral Blood Flow and Metabolism. 1996;16:705-713.
Arrigoni, Chiara, et al. "Rotating versus perfusion bioreactor for the culture of engineered vascular constructs based on hyaluronic acid." Biotechnology and bioengineering 100.5 (2008): 988-997.
Bai/Delaney (Nohla Therapeutics) showed that expanding Cord Blood-derived CD34+CD38– CD45RA– HSPCs in a biodegradable zwitterionic hydrogel with a rNotch ligand cocktail for 24 days mitigated HSPC differentiation and promoted self-renewal of lymphoid and myeloid cell phenotypes in an NSG mouse model (Nature Medicine, 2019).
Ballas CB, Zielske SP, Gerson SL (2002) Adult bone marrow stem cells for cell and gene therapies: implications for greater use. J Cell Biochem Suppl 38: 20-28.
Ballke C, Gran E, Baekkevold ES, Jahnsen FL. Characterization of Regulatory T-Cell Markers in CD4+ T Cells of the Upper Airway Mucosa. PLoS One. 2016;11(2):e0148826.
Baraniak PR, McDevitt TC (2010) Stem cell paracrine actions and tissue regeneration. Regen Med 5(1): 121-143.
Barckhausen C, Rice B, Baila S, et al. (2016) GMP-Compliant Expansion of Clinical-Grade Human Mesenchymal Stromal/Stem Cells Using a Closed Hollow Fiber Bioreactor. Methods Mol Biol 1416: 389-412.
Bazarian JJ, Cernak I, Noble-Haeusslein L, Potolicchio S, Temkin N. Long-term neurologic outcomes after traumatic brain injury. The Journal of head trauma rehabilitation. 2009;24:439- 451.
Bending D, Pesenacker AM, Ursu S, Wu Q, Lom H, Thirugnanabalan B, Wedderburn LR. Hypomethylation at the regulatory T cell-specific demethylated region in CD25hi T cells is decoupled from FOXP3 expression at the inflamed site in childhood arthritis. J Immunol. 2014;193(6):2699-708.
Berendse M, Grounds MD, Lloyd CM (2003) Myoblast structure affects subsequent skeletal myotube morphology and sarcomere assembly. Exp Cell Res 291(2): 435-450.
Bernard, A., Payton, Mar. 1995. "Fermentation and Growth of *Escherichia coli* for Optimal Protein Production", John Wiley & Sons. Current Protocols in Protein Science (1995) 5.3.1-5.3.18.

Berney SM, Schaan T, Wolf RE, van der Heyde H, Atkinson TP. CD2 (OKT11) augments CD3-mediated intracellular signaling events in human T lymphocytes. J Investig Med. 2000;48(2):102-9.
Bioheart Clinical Trial Clinica 1302 Apr. 18, 2008.
Biomolecular and Cellular Interactions with the Hollow Fiber Membrane Currently Used in the Quantum® Cell Expansion System. 12th NJ Symposium on Biomaterials Science, Oct. 6- 7, 2014, New Brunswick, NJ.
Blache C, Chauvin JM, Marie-Cardine A, Contentin N, Pommier P, Dedreux I, Francois S, Jacquot S, Bastit D, Boyer O. Reduced frequency of regulatory T cells in peripheral blood stem cell compared to bone marrow transplantations. Biol Blood Marrow Transplant. 2010;16(3):430-4.
Bluestone et al. Type 1 diabetes immunotherapy using polyclonal regulatory T cells. Science Translational Medicine 7(315):1-34, 2015.
Bluestone JA, Tang Q. Treg cells-the next frontier of cell therapy. Science. 2018;362(6411):154-155.
Bluestone, Jeffrey A., et al. "Type 1 diabetes immunotherapy using polyclonal regulatory T cells." *Science translational medicine* 7.315 (2015): 315ra189-315ra189.
Blum S, Moore AN, Adams F, Dash PK. A mitogen-activated protein kinase cascade in the ca1/ca2 subfield of the dorsal hippocampus is essential for long-term spatial memory. The Journal of neuroscience : the official journal of the Society for Neuroscience. 1999;19:3535-3544.
Bojun Li et al. Heparin-induced conformation changes of fibronectin within the extracellular matrix promote hMSC osteogenic differentiation. Biomaterials Science 3: 73-84, 2015.
Boquest AC, Shahdadfar A, Brinchmann JE, Collas P. Isolation of Stromal Stem Cells from Human Adipose Tissue. Methods Mol Biol. 2006;325:35-46. doi: 10.1385/1-59745-005-7:35. PMID: 16761717.
Borden, M. and Longo, M., "Dissolution Behavior of Lipid Monolayer-Coated, Air-Filled Microbubbles: Effect of Lipid Hydrophobic Chain Length," Langmuir, vol. 18, pp. 9225-9233, 2002.
Bourke, Sharon L., and Joachim Kohn. "Polymers derived from the amino acid L-tyrosine: polycarbonates, polyarylates and copolymers with poly (ethylene glycol)." Advanced drug delivery reviews 55.4 (2003): 447-466.
Brand, K. and Hermfisse, U., "Aerobic Glycolysis by Proliferating Cells: a Protective Strategy against Reactive Oxygen Species," The FASEB Journal, vol. 11, pp. 388-395, Apr. 1997.
Brentjens et al., "CD19-Targeted T Cells Rapidly Induce Molecular Remission in Adults with Chemotherapy-Refractory Acute Lympohblastic Leukemia," Science Translational Medicine, vol. 5, Issue 177, pp. 1-9, Mar. 20, 2013.
Brentjens et al., "Safety and Persistance of Adoptively Transferred Autologous CD19-Target T Cells in Patients with Relapsed or Chemotherapy Refractory B-Cell Leukemias," Blood, vol. 118, No. 18, pp. 4817-4828, Nov. 3, 2011.
Carswell, K. and Papoutsakis, E. "Culture of Human T Cells in Stirred Bioreactors for Cellular Immunotherapy Applications: Shear, Proliferation, and the IL-2 Receptor," Biotechnology and Bioengineering, vol. 68, No. 3, pp. 329-338, May 5, 2000.
Chapman NM, Chi H. mTOR signaling, Tregs and immune modulation. Immunotherapy. 2014;6(12):1295-311.
Chaudhry A, Samstein RM, Treuting P, Liang Y, Pils MC, Heinrich JM, Jack RS, Wunderlich FT, Bruning JC, Muller W, Rudensky AY. Interleukin-10 signaling in regulatory T cells is required for suppression of Th17 cell-mediated inflammation. Immunity. 2011;34(4):566-78.
Chen, C. and Broden, M., "The Role of Poly(theylene glycol) Brush Architecture in Complement Activation on Targeted Microbubble Surfaces," Biomaterials, vol. 32, No. 27, pp. 6579-6587, Jun. 17, 2011.
Choi W, Kwon SJ, Jin HJ, et al. (2017) Optimization of culture conditions for rapid clinical-scale expansion of human umbilical cord blood-derived mesenchymal stem cells. Clin Transl Med 6(1): 38.

(56) References Cited

OTHER PUBLICATIONS

Chullikana A, Majumdar AS, Gottipamula S, et al. (2015) Randomized, double-blind, phase I/II study of intravenous allogeneic mesenchymal stromal cells in acute myocardial infarction. Cytotherapy 17(3): 250-261.

Claudio G. Brunstein, Jeffrey S. Miller, Qing Cao, Daivd H. McKenna, Keli L. Hippen, Julie Curtsinger, Todd Defor, Bruce L. Levine, Carl H. June, Pablo Rubinstein, Philip B. McGlave, Bruce R. Blazar, and John E. Wagner. Infusion of ex vivo expanded T regulatory cells in adults transplanted with umbilical cord blood: safety profile and detection kinetics. Blood, 117(3): 1061-1070, 2010.

Coeshott C, Vang B, Jones M, Nankervis B. Large-scale expansion and characterization of CD3(+) T-cells in the Quantum((R)) Cell Expansion System. J Transl Med. 2019;17(1):258.

Coombes JL, Robinson NJ, Maloy KJ, Uhlig HH, Powrie F. Regulatory T cells and intestinal homeostasis. Immunol Rev. 2005;204:184-94.

Coquillard C. mTOR Signaling in Regulatory T cell Differentiation and Expansion. SOJ Immunology. 2015;3(1):1-10.

Creed JA, DiLeonardi AM, Fox DP, Tessler AR, Raghupathi R. Concussive brain trauma in the mouse results in acute cognitive deficits and sustained impairment of axonal function. Journal of neurotrauma. 2011;28:547-563.

Dash PK, Hochner B, Kandel ER. Injection of the camp-responsive element into the nucleus of aplysia sensory neurons blocks long-term facilitation. Nature. 1990;345:718-721.

Dash PK, Johnson D, Clark J, Orsi SA, Zhang M, Zhao J, Grill RJ, Moore AN, Pati S. Involvement of the glycogen synthase kinase-3 signaling pathway in tbi pathology and neurocognitive outcome. PloS one. 2011;6:e24648.

Dash PK, Mach SA, Blum S, Moore AN. Intrahippocampal wortmannin infusion enhances long-term spatial and contextual memories. Learn Mem. 2002;9:167-177.

Dash PK, Orsi SA, Zhang M, Grill RJ, Pati S, Zhao J, Moore AN. Valproate administered after traumatic brain injury provides neuroprotection and improves cognitive function in rats. PloS one. 2010;5:e11383.

Dash PK, Zhao J, Orsi SA, Zhang M, Moore AN. Sulforaphane improves cognitive function administered following traumatic brain injury. Neuroscience letters. 2009;460:103-107.

Davila et al., "Efficacy and Toxicity Management of 19-28z CAR T Cell Therapy in B cell Acute Lymphoblastic Leukemia," Science Translational Medicine, vol. 6, No. 224, pp. 1-10, Feb. 19, 2014.

Dejana E, Orsenigo F, Lampugnani MG. The role of adherens junctions and ve-cadherin in the control of vascular permeability. Journal of cell science. 2008;121:2115-2122.

Dejana E, Spagnuolo R, Bazzoni G. Interendothelial junctions and their role in the control of angiogenesis, vascular permeability and leukocyte transmigration. Thrombosis and haemostasis. 2001;86:308-315.

Dejana E, Tournier-Lasserve E, Weinstein BM. The control of vascular integrity by endothelial cell junctions: Molecular basis and pathological implications. Developmental cell. 2009;16:209-221.

Del Pino A, Ligero G, Lopez MB, et al. (2015) Morphology, cell viability, karyotype, expression of surface markers and plasticity of three primary cell line cultures before and after the cryostorage in LN2 and GN2. Cryobiology 70(1): 1-8.

Delaney, Colleen, et al. "Notch-mediated expansion of human cord blood progenitor cells capable of rapid myeloid reconstitution." Nature medicine 16.2 (2010): 232-236.

Ding, Zhongli, Guohua Chen, and Allan S. Hoffman. "Synthesis and purification of thermally Sensitive oligomer? enzyme conjugates of poly (N-isopropylacrylamide)? trypsin." Bioconjugate chemistry 7.1 (1996): 121-125.

Dixon CE, Clifton GL, Lighthall JW, Yaghmai AA, Hayes RL. A controlled cortical impact model of traumatic brain injury in the rat. Journal of neuroscience methods. 1991;39:253-262.

Dominici M, Le Blanc K, Mueller I, et al. (2006) Minimal criteria for defining multipotent mesenchymal stromal cells. The International Society for Cellular Therapy position statement. Cytotherapy 8(4): 315-317.

Durrani S, Konoplyannikov M, Ashraf M, Haider KH (2010) Skeletal myoblasts for cardiac repair. Regen Med 5(6): 919-932.

Esensten JH, Muller YD, Bluestone JA, Tang Q. Regulatory T-cell therapy for autoimmune and autoinflammatory diseases: The next frontier. J Allergy Clin Immunol. 2018;142(6):1710-1718.

Fakin R, Hamacher J, Gugger M, Gazdhar A, Moser H, Schmid RA. Prolonged amelioration of acute lung allograft rejection by sequential overexpression of human interleukin-10 and hepatocyte growth factor in rats. Exp Lung Res. 2011;37(9):555-62.

Fedorov et al., "PD-1- and CTLA-4-Based Inhibitory Chimeric Antigen Receptors (iCARs) Divert Off-Target Immunotherapy Responses," Science Translational Medicine, vol. 5, No. 215, pp. 1-12, Dec. 11, 2013.

Ferreira LMR, Muller YD, Bluestone JA, Tang Q. Next-generation regulatory T cell therapy. Nat Rev Drug Discov. 2019;18(10):749-769.

Fischbach, Michael A., Jeffrey A. Bluestone, and Wendell A. Lim. "Cell-based therapeutics: the next pillar of medicine." Science translational medicine 5.179 (2013): 179ps7-179ps7.

Fisk, Nicholas M., et al. "Can routine commercial cord blood banking be scientifically and ethically justified ?. " PLoS medicine 2.2 (2005): e44.

Forbes Jun. 23, 2014 article "Will this man cure cancer?".

Fowler DH. Rapamycin-resistant effector T-cell therapy. Immunol Rev. 2014;257(1):210-25.

Fraser H, Safinia N, Grageda N, Thirkell S, Lowe K, Fry LJ, Scotta C, Hope A, Fisher C, Hilton R, Game D, Harden P, Bushell A, Wood K, Lechler RI, Lombardi G. A Rapamycin-Based GMP-Compatible Process for the Isolation and Expansion of Regulatory T Cells for Clinical Trials. Mol Ther Methods Clin Dev. 2018;8:198-209.

Frauwirth KA, Riley JL, Harris MH, Parry RV, Rathmell JC, Plas DR, Elstrom RL, June CH, Thompson CB. The CD28 signaling pathway regulates glucose metabolism. Immunity. 2002;16(6):769-77.

Fuchs A, Gliwinski M, Grageda N, Spiering R, Abbas AK, Appel S, Bacchetta R, Battaglia M, Berglund D, Blazar B, Bluestone JA, Bornhauser M, Ten Brinke A, Brusko TM, Cools N, Cuturi MC, Geissler E, Giannoukakis N, Golab K, Hafler DA, van Ham SM, Hester J et al. Minimum Information about T Regulatory Cells: A Step toward Reproducibility and Standardization. Front Immunol. 2017;8:1844.

G0211: Study for Gamma Irradiation of Bioreactor Membranes, undated, author unknown, 3 pages.

Galgani M, De Rosa V, La Cava A, Matarese G. Role of Metabolism in the Immunobiology of Regulatory T Cells. J Immunol. 2016;197(7):2567-75.

Gedaly R, De Stefano F, Turcios L, Hill M, Hidalgo G, Mitov MI, Alstott MC, Butterfield DA, Mitchell HC, Hart J, Al-Attar A, Jennings CD, Marti F. mTOR Inhibitor Everolimus in Regulatory T Cell Expansion for Clinical Application in Transplantation. Transplantation. 2019;103(4):705- 715.

Gimble, Jeffrey M., Adam J. Katz, and Bruce A. Bunnell. "Adipose-derived stem cells for regenerative medicine." Circulation research 100.9 (2007): 1249-1260.

Gingras AC, Raught B, Sonenberg N. Regulation of translation initiation by FRAP/mTOR. Genes Dev. 2001;15(7):807-26.

Godin, Michel, et al. "Measuring the mass, density, and size of particles and cells using a suspended microchannel resonator." Applied physics letters 91.12 (2007): 123121.

Goh, Celeste, Sowmya Narayanan, and Young S. Hahn. "Myeloid-derived suppressor cells: the dark knight or the joker in viral infections ?. " Immunological reviews 255.1 (2013): 210-221.

Golab K, Leveson-Gower D, Wang XJ, Grzanka J, Marek-Trzonkowska N, Krzystyniak A, Millis JM, Trzonkowski P, Witkowski P. Challenges in cryopreservation of regulatory T cells (Tregs) for clinical therapeutic applications. Int Immunopharmacol. 2013;16(3):371-5.

Goldring CE, Duffy PA, Benvenisty N, Andrews PW, Ben-David U, Eakins R, French N, Hanley NA, Kelly L, Kitteringham NR, Kurth

(56) References Cited

OTHER PUBLICATIONS

J, Ladenheim D, Laverty H, McBlane J, Narayanan G, Patel S, Reinhardt J, Rossi A, Sharpe M, Park BK. Assessing the safety of stem cell therapeutics. Cell stem cell. 2011;8:618-628.

Griesche, Nadine, et al. "A simple modification of the separation method reduces heterogeneity of adipose-derived stem cells." cells tissues organs 192.2 (2010): 106-115.

Gutcher I, Donkor MK, Ma Q, Rudensky AY, Flavell RA, Li MO. Autocrine transforming growth factor-beta1 promotes in vivo Th17 cell differentiation. Immunity. 2011;34(3):396-408.

Haack-Sorensen M, Follin B, Juhl M, et al. (2016) Culture expansion of adipose derived stromal cells. A closed automated Quantum Cell Expansion System compared with manual flask-based culture. J Transl Med 14(1): 319.

Hall ED, Sullivan PG, Gibson TR, Pavel KM, Thompson BM, Scheff SW. Spatial and temporal characteristics of neurodegeneration after controlled cortical impact in mice: More than a focal brain injury. Journal of neurotrauma. 2005;22:252-265.

Hami et al., "GMP Production and Testing of Xcellerated T Cells for the Treatment of Patients with CLL," Cytotherapy, pp. 554-562, 2004.

Hamm RJ, Dixon CE, Gbadebo DM, Singha AK, Jenkins LW, Lyeth BG, Hayes RL. Cognitive deficits following traumatic brain injury produced by controlled cortical impact. Journal of neurotrauma. 1992;9:11-20.

Hanley PJ, Mei Z, Durett AG, et al. (2014) Efficient manufacturing of therapeutic mesenchymal stromal cells with the use of the Quantum Cell Expansion System. Cytotherapy 16(8): 1048- 1058.

He N, Fan W, Henriquez B, Yu RT, Atkins AR, Liddle C, Zheng Y, Downes M, Evans RM. Metabolic control of regulatory T cell (Treg) survival and function by Lkb1. Proc Natl Acad Sci USA. 2017;114(47):12542-12547.

He X, Landman S, Bauland SC, van den Dolder J, Koenen HJ, Joosten I. A TNFR2-Agonist Facilitates High Purity Expansion of Human Low Purity Treg Cells. PLoS One. 2016;11(5):e0156311.

Heskins, Michael, and James E. Guillet. "Solution properties of poly (N-isopropylacrylamide)." Journal of Macromolecular Science-Chemistry 2.8 (1968): 1441-1455.

Hill JA, Feuerer M, Tash K, Haxhinasto S, Perez J, Melamed R, Mathis D, Benoist C. Foxp3 transcription-factor-dependent and -independent regulation of the regulatory T cell transcriptional signature. Immunity. 2007;27(5):786-800.

Hollyman et al., "Manufacturing Validation of Biologicall Functional T Cells Targeted to CD19 Antigen for Autologous Adoptive Cell Therapy," J Immunother, vol. 32, No. 2, pp. 169-180, Feb.-Mar. 2009.

Horwitz, Mitchell E., et al. "Phase I/II study of stem-cell transplantation using a single cord blood unit expanded ex vivo with nicotinamide." *Journal of Clinical Oncology* 37.5 (2019): 367-373. http://www.ucdenver.edu/academics/colleges/medicalschool/centers/cancercenter/Research/sharedresources/AnimalImaging/smallanimalimaging/Pages/MRI.aspx.

ISCT Webinar "vol. Reduction technology for Large Scale Harvest or Post-thaw Manipulation of Cellular Therapeutics".

Iwashima, Shigejiro, et al. "Novel culture system of mesenchymal stromal cells from human subcutaneous adipose tissue." Stem cells and development 18.4 (2009): 533-544.

Jarocha D, Stangel-Wojcikiewicz K, Basta A, Majka M (2014) Efficient myoblast expansion for regenerative medicine use. Int J Mol Med 34(1): 83-91.

Jin, H., and J. Bae. "Neuropeptide Y regulates the hematopoietic stem cell microenvironment and prevents nerve injury in the bone marrow." *22nd Annual ISCT Meeting* (2016): S29.

Jo CH, Lee YG, Shin WH, et al. (2014) Intra-articular injection of mesenchymal stem cells for the treatment of osteoarthritis of the knee: a proof-of-concept clinical trial. Stem Cells 32(5): 1254-1266.

John Nicolette, et al.(Abbott Laboratories). In Vitro Micronucleus Screening of Pharmaceutical Candidates by Flow Cyto9metry in Chinese Hamster V79 Cells, Environmental and Molecular Mutagenesis 00:000-000, 2010.

Johnson, Patrick A., et al. "Interplay of anionic charge, poly (ethylene glycol), and iodinated tyrosine incorporation within tyrosine ?derived polycarbonates: Effects on vascular smooth muscle cell adhesion, proliferation, and motility." Journal of Biomedical Materials Research Part A: An Official Journal of The Society for Biomaterials, The Japanese Society for Biomaterials, and The Australian Society for Biomaterials and the Korean Society for Biomaterials 93.2 (2010): 505-514.

Johnston LC, Su X, Maguire-Zeiss K, Horovitz K, Ankoudinova I, Guschin D, Hadaczek P, Federoff HJ, Bankiewicz K, Forsayeth J. Human interleukin-10 gene transfer is protective in a rat model of Parkinson's disease. Mol Ther. 2008;16(8):1392-9.

Jones2016ISCT 2016 Poster 69.

Joy, Abraham, et al. "Control of surface chemistry, substrate stiffness, and cell function in a novel terpolymer methacrylate library." Langmuir 27.5 (2011): 1891-1899.

Kalamasz et al., "Optimization of Human T-Cell Expansion Ex Vivo Using Magnetic Beads Conjugated with Anti-CD3 and Anti-CD28 Antibodies," J Immunother, vol. 27, No. 5, pp. 405-418, Sep.-Oct. 2004.

Kim, Do-Hyung, et al. "mTOR interacts with raptor to form a nutrient-sensitive complex that signals to the cell growth machinery." *Cell* 110.2 (2002): 163-175.

Kishore M, Cheung KCP, Fu H, Bonacina F, Wang G, Coe D, Ward EJ, Colamatteo A, Jangani M, Baragetti A, Matarese G, Smith DM, Haas R, Mauro C, Wraith DC, Okkenhaug K, Catapano AL, De Rosa V, Norata GD, Marelli-Berg FM. Regulatory T Cell Migration Is Dependent on Glucokinase-Mediated Glycolysis. Immunity. 2017;47(5):875-889 e10.

Klapper et al., "Single-Pass, Closed-System Rapid Expansion of Lymphocyte Cultures for Adoptive Cell Therapy," Journal of Immunological Methods, 345, pp. 90-99, Apr. 21, 2009.

Klysz D, Tai X, Robert PA, Craveiro M, Cretenet G, Oburoglu L, Mongellaz C, Floess S, Fritz V, Matias MI, Yong C, Surh N, Marie JC, Huehn J, Zimmermann V, Kinet S, Dardalhon V, Taylor N. Glutamine-dependent alpha-ketoglutarate production regulates the balance between T helper 1 cell and regulatory T cell generation. Sci Signal. 2015;8(396):ra97.

Korpanty et al., "Tageting Vascular Enothelium with Avidin Microbubbles," Ultrasound in Medicine and Biology, vol. 31, No. 9, pp. 1279-1283, May 24, 2005.

Krauss et al., "Signaling Takes a Breath—New Quantitative Perspectives on Bioenergetics and Signal Transduction," Immunity, vol. 15, pp. 497-502, Oct. 2001.

Kulikov, A. V., et al. "Application of multipotent mesenchymal stromal cells from human adipose tissue for compensation of neurological deficiency induced by 3-nitropropionic acid in rats." Bulletin of experimental biology and medicine 145.4 (2008): 514-519.

Kumar P, Marinelarena A, Raghunathan D, Ragothaman VK, Saini S, Bhattacharya P, Fan J, Epstein AL, Maker AV, Prabhakar BS. Critical role of OX40 signaling in the TCR-independent phase of human and murine thymic Treg generation. Cell Mol Immunol. 2019;16(2):138-153.

Kwan, J. and Borden, M., "Lipid Monolayer Collapse and Microbubble Stability," Advances in Colloid and Interface Science, vols. 183-184, pp. 82-99, Aug. 21, 2012.

Lampugnani MG, Caveda L, Breviario F, Del Maschio A, Dejana E. Endothelial cell-to-cell junctions. Structural characteristics and functional role in the regulation of vascular permeability and leukocyte extravasation. Bailliere's clinical haematology. 1993;6:539-558.

Lee et al., "Continued Antigen Stimulation Is Not Required During CD4+ T Cell Clonal Expansion," The Journal of Immunology, 168, pp. 1682-1689, 2002.

Lee, Jae W., et al. "Allogeneic human mesenchymal stem cells for treatment of E. coli endotoxin-induced acute lung injury in the ex vivo perfused human lung." Proceedings of the national academy of Sciences 106.38 (2009): 16357-16362.

Levine, B., "T Lymphocyte Engineering ex vivo for Cancer and Infectious Disease," Expert Opinion on Biological Therapy, vol. 4, No. 4, pp. 475-489, 2008.

(56) References Cited

OTHER PUBLICATIONS

Lindstein, Tullia, et al. "Regulation of lymphokine messenger RNA stability by a surface- mediated T cell activation pathway." *Science* 244.4902 (1989): 339-343.
Liotta, Francesco, et al. "Frequency of regulatory T cells in peripheral blood and in tumour-infiltrating lymphocytes correlates with poor prognosis in renal cell carcinoma." *BJU international* 107.9 (2011): 1500-1506.
Liu W, Putnam AL, Xu-Yu Z, Szot GL, Lee MR, Zhu S, Gottlieb PA, Kapranov P, Gingeras TR, Fazekas de St Groth B, Clayberger C, Soper DM, Ziegler SF, Bluestone JA. CD127 expression inversely correlates with FoxP3 and suppressive function of human CD4+ T reg cells. J Exp Med. 2006;203(7):1701-1711.
Lum et al., "Ultrasound Radiation Force Enables Targeted Deposition of Model Drug Carriers Loaded on Microbubbles," Journal of Controlled Release, 111, pp. 128-134, 2006.
Malone et al., "Characterization of Human Tumor-Infiltrating Lymphocytes Expanded in Hollow-Fiber Bioreactors for Immunotherapy of Cancer," Cancer Biotherapy & Radiopharmaceuticals, vol. 16, No. 5, pp. 381-390, 2001.
Mao AS, Mooney DJ (2015) Regenerative medicine: current therapies and future directions. Proc Natl Acad Sci USA 112(47): 14452-14459.
Markgraf CG, Clifton GL, Aguirre M, Chaney SF, Knox-Du Bois C, Kennon K, Verma N. Injury severity and sensitivity to treatment after controlled cortical impact in rats. Journal of neurotrauma. 2001;18:175-186.
Mathew et al. A Phase I Clinical Trials I with Ex Vivo Expanded Recipient Regulatory T cells in Living Donor Kidney Transplants. Nature, Scientific Reports 8:7428 (1-12), 2018.
Matthay, Michael A., et al. "Therapeutic potential of mesenchymal stem cells for severe acute lung injury." Chest 138.4 (2010): 965-972.
Maynard CL, Harrington LE, Janowski KM, Oliver JR, Zindl CL, Rudensky AY, Weaver CT. Regulatory T cells expressing interleukin 10 develop from Foxp3+ and Foxp3-precursor cells in the absence of interleukin 10. Nat Immunol. 2007;8(9):931-41.
McKenna DH, Jr., Sumstad D, Kadidlo DM, et al. Optimization of cGMP purification and expansion of umbilical cord blood-derived T-regulatory cells in support of first-in-human clinical trials. Cytotherapy 2017;19:250-62.
McLimans W, Kinetics of Gas Diffusion in Mammalian Cell Culture Systems. Biotechnology and Bioengineering 1968; 10:725-740.
McMurtrey, Richard J. "Analytic models of oxygen and nutrient diffusion, metabolism dynamics, and architecture optimization in three-dimensional tissue constructs with applications and insights in cerebral organoids." Tissue Engineering Part C: Methods 22.3 (2016): 221-249.
Menge, Tyler, et al. "Mesenchymal stem cells regulate blood-brain barrier integrity through TIMP3 release after traumatic brain injury." Science translational medicine 4.161 (2012): 161ra150-161ra150.
Miska J, Lee-Chang C, Rashidi A, Muroski ME, Chang AL, Lopez-Rosas A, Zhang P, Panek Wk, Cordero A, Han Y, Ahmed AU, Chandel NS, Lesniak MS. HIF-1alpha Is a Metabolic Switch between Glycolytic-Driven Migration and Oxidative Phosphorylation-Driven Immunosuppression of Tregs in Glioblastoma. Cell Rep. 2019;27(1):226-237 e4.
Miyara M, Yoshioka Y, Kitoh A, Shima T, Wing K, Niwa A, Parizot C, Taflin C, Heike T, Valeyre D, Mathian A, Nakahata T, Yamaguchi T, Nomura T, Ono M, Amoura Z, Gorochov G, Sakaguchi S. Functional delineation and differentiation dynamics of human CD4+ T cells expressing the FoxP3 transcription factor. Immunity. 2009;30(6):899-911.
Nankervis B, Jones M, Vang B et al. (2018) Optimizing T Cell Expansion in a Hollow-Fiber Bioreactor. Curr Stem Cell Rep. Advanced online publication. https://doi.org/10.1007/s40778-018-0116-x.
Nankervis, Brian, et al. "Optimizing T cell expansion in a hollow-fiber bioreactor." Current Stem Cell Reports 4.1 (2018): 46-51.
Nedoszytko B, Lange M, Sokolowska-Wojdylo M, Renke J, Trzonkowski P, Sobjanek M, Szczerkowska-Dobosz A, Niedoszytko M, Gorska A, Romantowski J, Czarny J, Skokowski J, Kalinowski L, Nowicki R. The role of regulatory T cells and genes involved in their differentiation in pathogenesis of selected inflammatory and neoplastic skin diseases. Part II: The Treg role in skin diseases pathogenesis. Postepy Dermatol Alergol. 2017;34(5):405-417.
Nehlin JO, Just M, Rustan AC (2011) Human myotubes from myoblast cultures undergoing senescence exhibit defects in glucose and lipid metabolism. Biogerontology 12: 349-365.
New victories for adult Stem Cell Research New York Feb. 6, 2007.
Newton R, Priyadharshini B, Turka LA. Immunometabolism of regulatory T cells. Nat Immunol. 2016;17(6):618-25.
Ng TH, Britton GJ, Hill EV, Verhagen J, Burton BR, Wraith DC. Regulation of adaptive immunity; the role of interleukin-10. Front Immunol. 2013;4:129.
Nikolaychik, V. V., M. M. Samet, and P. I. Lelkes. "A New, Cryoprecipitate Based Coating For Improved Endothelial Cell Attachment And Growth On Medical Grade Artificial Surfaces." ASAIO Journal (American Society for Artificial Internal Organs: 1992) 40.3 (1994): M846-52.
Nish SA, Schenten D, Wunderlich FT, Pope SD, Gao Y, Hoshi N, Yu S, Yan X, Lee HK, Pasman L, Brodsky I, Yordy B, Zhao H, Bruning J, Medzhitov R. T cell-intrinsic role of IL-6 signaling in primary and memory responses. Elife. 2014;3:e01949.
Niwayama, Jun, et al. "Analysis of hemodynamics during blood purification therapy using a newly developed noninvasive continuous monitoring method." Therapeutic Apheresis and Dialysis 10.4 (2006): 380-386.
Okano et al.(Tokyo Women's Medical College, Japan) demonstrated the recovery of endothelial cells and hepatocytes from plasma-treated polystyrene dishes grafted with PNIAAm (Journal of Biomedical Materials Research, 1993).
Onishi Y, Fehervari Z, Yamaguchi T, Sakaguchi S. Foxp3+ natural regulatory T cells preferentially form aggregates on dendritic cells in vitro and actively inhibit their maturation. Proc Natl Acad Sci U S A. 2008;105(29):10113-8.
Onyszchuk G, LeVine SM, Brooks WM, Berman NE. Post-acute pathological changes in the thalamus and internal capsule in aged mice following controlled cortical impact injury: A magnetic resonance imaging, iron histochemical, and glial immunohistochemical study. Neuroscience letters. 2009;452:204-208.
Pacella I, Procaccini C, Focaccetti C, Miacci S, Timperi E, Faicchia D, Severa M, Rizzo F, Coccia EM, Bonacina F, Mitro N, Norata GD, Rossetti G, Ranzani V, Pagani M, Giorda E, Wei Y, Matarese G, Barnaba V, Piconese S. Fatty acid metabolism complements glycolysis in the selective regulatory T cell expansion during tumor growth. Proc Natl Acad Sci U S A. 2018;115(28):E6546-E6555.
Parhi, Purnendu, Avantika Golas, and Erwin A. Vogler. "Role Of Proteins And Water In The Initial Attachment Of Mammalian Cells To Biomedical Surfaces: A Review." Journal of Adhesion Science and Technology 24.5 (2010): 853-888.
Pati S, Gerber MH, Menge TD, Wataha KA, Zhao Y, Baumgartner JA, Zhao J, Letourneau PA, Huby MP, Baer LA, Salsbury JR, Kozar RA, Wade CE, Walker PA, Dash PK, Cox CS, Jr., Doursout MF, Holcomb JB. Bone marrow derived mesenchymal stem cells inhibit inflammation and preserve vascular endothelial integrity in the lungs after hemorrhagic shock. PloS one. 2011;6:e25171.
Pati S, Khakoo AY, Zhao J, Jimenez F, Gerber MH, Harting M, Redell JB, Grill R, Matsuo Y, Guha S, Cox CS, Reitz MS, Holcomb JB, Dash PK. Human mesenchymal stem cells inhibit vascular permeability by modulating vascular endothelial cadherin/beta-catenin signaling. Stem cells and development. 2011;20:89-101.
Pati, Shibani, and Todd E. Rasmussen. "Cellular therapies in trauma and critical care medicine: Looking towards the future." *PLoS Medicine* 14.7 (2017): e1002343.
Pati, Shibani, et al. "Lyophilized plasma attenuates vascular permeability, inflammation and lung injury in hemorrhagic shock." *PLoS one* 13.2 (2018): e0192363.
Peters JH, Preijers FW, Woestenenk R, Hilbrands LB, Koenen HJ, Joosten I. Clinical grade Treg: GMP isolation, improvement of purity by CD127 Depletion, Treg expansion, and Treg cryopreservation. PLoS One. 2008;3(9):e3161.

(56) References Cited

OTHER PUBLICATIONS

Peters, R.; Jones, M.; Brecheisen, M.; Startz, T.; Vang, B.; Nankervis, B.; Frank, N.; Nguyen, K. (2012) TerumoBCT. https://www.terumobct.com/location/north-america/products-and-services/Pages/Quantum-Materials.aspx.

Porter CM, Horvath-Arcidiacono JA, Singh AK, Horvath KA, Bloom ET, Mohiuddin MM. Characterization and expansion of baboon CD4+CD25+ Treg cells for potential use in a non-human primate xenotransplantation model. Xenotransplantation. 2007;14(4):298-308.

Povsic TJ, O'Connor CM, Henry T, et al. (2011) A double-blind, randomized, controlled, multicenter study to assess the safety and cardiovascular effects of skeletal myoblast implantation by catheter delivery in patients with chronic heart failure after myocardial infarction. Am Heart J 162(4): 654-662.

Prockop, Darwin J., Carl A. Gregory, and Jeffery L. Spees. "One strategy for cell and gene therapy: harnessing the power of adult stem cells to repair tissues." Proceedings of the National Academy of Sciences 100.suppl_1 (2003): 11917-11923.

Q. L. Hao, et al. A functional comparison of CD34+ CD38= cells in cord blood and bone marrow. Blood 86:3745-3753, 1995.

Rey-Jurado, Emma, et al. "Assessing the importance of domestic vaccine manufacturing centers: an overview of immunization programs, vaccine manufacture, and distribution." Frontiers in immunology 9 (2018): 26.

Roballo KC, Dhungana S, Z. J, Oakey J, Bushman J. Localized delivery of immunosuppressive regulatory T cells to peripheral nerve allografts promotes regeneration of branched segmental defects. Biomaterials. 2019;209:1-9.

Ronco C1, Levin N, Brendolan A, Nalesso F, Cruz D, Ocampo C, Kuang D, Bonello M, De Cal M, Corradi V, Ricci Z. Flow distribution analysis by helical scanning in polysulfone hemodialyzers: effects of fiber structure and design on flow patterns and solute clearances. Hemodial Int. Oct. 2006; 10(4):380-8.

Rosenblum MD, Way SS, Abbas AK. Regulatory T cell memory. Nat Rev Immunol. 2016;16(2):90-101.

Rubtsov YP, Rasmussen JP, Chi EY, Fontenot J, Castelli L, Ye X, Treuting P, Siewe L, Roers A, Henderson WR, Jr., Muller W, Rudensky AY. Regulatory T cell-derived interleukin-10 limits inflammation at environmental interfaces. Immunity. 2008;28(4):546-58.

Rudensky, Alexander Y. "Regulatory T cells and Foxp3." Immunological reviews 241.1 (2011): 260-268.

Safinia N, Grageda N, Scotta C, Thirkell S, Fry LJ, Vaikunthanathan T, Lechler RI, Lombardi G. Cell Therapy in Organ Transplantation: Our Experience on the Clinical Translation of Regulatory T Cells. Front Immunol. 2018;9:354.

Sahay A, Scobie KN, Hill AS, O'Carroll CM, Kheirbek MA, Burghardt NS, Fenton AA, Dranovsky A, Hen R. Increasing adult hippocampal neurogenesis is sufficient to improve pattern separation. Nature. 2011;472:466-470.

Sakaguchi S, Sakaguchi N, Asano M, Itoh M, Toda M. Immunologic self-tolerance maintained by activated T cells expressing IL-2 receptor alpha-chains (CD25). Breakdown of a single mechanism of self-tolerance causes various autoimmune diseases. J Immunol. 1995;155(3):1151-64.

Sakaguchi S, Sakaguchi N, Shimizu J, Yamazaki S, Sakihama T, Itoh M, Kuniyasu Y, Nomura T, Toda M, Takahashi T. Immunologic tolerance maintained by CD25+ CD4+ regulatory T cells: their common role in controlling autoimmunity, tumor immunity, and transplantation tolerance. Immunol Rev. 2001;182:18-32.

Schild, Howard G. "Poly (N-isopropylacrylamide): experiment, theory and application." Progress in polymer science 17.2 (1992): 163-249.

Schmitz R, Alessio A, Kina P. The Physics of PET/CT scanners. Imaging Research Laboratory, Department of Radiology, University of Washington http://depts.washington.edu/imreslab/education/Physics%20of%20PET.pdf.

Schwartz Rh. T cell anergy. Annu Rev Immunol. 2003;21:305-34.

Shevkoplyas et al., "The Force Acting on a Superparamagnetic Bead due to an Applied Magnetic Field," Lab on a Chip, 7, pp. 1294-1302, 2007.

Shimazu Y, Shimazu Y, Hishizawa M, Hamaguchi M, Nagai Y, Sugino N, Fujii S, Kawahara M, Kadowaki N, Nishikawa H, Sakaguchi S, Takaori-Kondo A. Hypomethylation of the Treg-Specific Demethylated Region in FOXP3 Is a Hallmark of the Regulatory T-cell Subtype in Adult T-cell Leukemia. Cancer Immunol Res. 2016;4(2):136-45.

Sigma-Aldrich Cheimcals Mitomycin C (M4287) MSDS, v4.4, Jul. 7, 2011.

Sirsi, S. and Borden, M., "Microbubble Composition, Properties, and Biomedical Applications," Bubble Science, Engineering & Technolology, vol. 1, No. 1-2, pp. 3-17, 2009.

Smith C, Okern G, Rehan S, et al. Ex vivo expansion of human T cells for adoptive immunotherapy using the novel Xeno-free CTS Immune Cell Serum Replacement. Clinical & Translational Immunology 2015;4:e31.

Somerville et al., "Clinical Scale Rapid Expansion of Lymphocytes for Adoptive Cell Transfer Therapy in the WAVE® Bioreactor," Journal of Translational Medicine, vol. 10, No. 69, pp. 1-11, 2012.

Somerville, R. and Dudley, M., "Bioreactors Get Personal," Oncolmmunology, vol. 1, No. 8, pp. 1435-1437, Nov. 2012.

Spectrum Labs KrosFlo Research IIi TFF System, undated, Spectrum Laboratories, Inc., 4 pages.

Stafano Tiziani, et al. Metabolomic Profiling of Drug Response in Acute Myeloid Leukaemia Cell lines. PLOSone 4(1): e4251 (Jan. 22, 2009).

StAR_Abstract, undated, author unknown, 1 page.

Startz et al May 2016 TBCT T-cell White Paper.

Startz, T., et al. "Maturation of dendritic cells from CD14+ monocytes in an automated functionally closed hollow fiber bioreactor system." Cytotherapy 16.4 (2014): S29.

Stuart, Martien A. Cohen, et al. "Emerging applications of stimuli-responsive polymer materials." Nature materials 9.2 (2010): 101-113.

Su LF, Del Alcazar D, Stelekati E, Wherry EJ, Davis MM. Antigen exposure shapes the ratio between antigen-specific Tregs and conventional T cells in human peripheral blood. Proc Natl Acad Sci U S A. 2016;113(41):E6192-E6198.

Trzonkowski et al., "Ex Vivo Expansion of CD4+ CD25+ T Regulatory Cells for Immunosuppressive Therapy," Cytometry Part A, 75A, pp. 175-188, 2009.

Trzonkowski, Piotr, et al. "First-in-man clinical results of the treatment of patients with graft versus host disease with human ex vivo expanded CD4+ CD25+ CD127? T regulatory cells." Clinical immunology 133.1 (2009): 22-26.

Tsvetkov, Ts, et al. "Isolation and cryopreservation of human peripheral blood monocytes." Cryobiology 23.6 (1986): 531-536.

Underwood, P. Anne, et al. "Effects of base material, plasma proteins and FGF2 on endothelial cell adhesion and growth." Journal of Biomaterials Science, Polymer Edition 13.8 (2002): 845-862.

van der Net JB, Bushell A, Wood KJ, Harden PN. Regulatory T cells: first steps of clinical application in solid organ transplantation. Transpl Int. 2016;29(1):3-11.

van der Windt GJ, Pearce EL. Metabolic switching and fuel choice during T-cell differentiation and memory development. Immunol Rev. 2012;249(1):27-42.

Vera et al., "Accelerated Production of Antigen-Specific T-Cells for Pre-Clinical and Clinical Applications Using Gas-Permeable Rapid Expansion Cultureware (G-Rex)," J Immunother, vol. 33, No. 3, pp. 305-315, Apr. 2010.

Villa, Alma Y. Camacho, et al. "CD133+ CD34+ and CD133+ CD38+ blood progenitor cells as predictors of platelet engraftment in patients undergoing autologous peripheral blood stem cell transplantation." Transfusion and Apheresis Science 46.3 (2012): 239-244.

Visser EP1, Disselhorst JA, Brom M, Laverman P, Gotthardt M, Oyen WJ, Boerman OC. Spatial resolution and sensitivity of the Inveon small-animal PET scanner. J Nucl Med. Jan. 2009;50(1):139-47.

(56) References Cited

OTHER PUBLICATIONS

Walker, Peter A., et al. "Direct intrathecal implantation of mesenchymal stromal cells leads to enhanced neuroprotection via an NF?B-mediated increase in interleukin-6 production." Stem cells and development 19.6 (2010): 867-876.

Wang R, Dillon CP, Shi LZ, Milasta S, Carter R, Finkelstein D, McCormick LL, Fitzgerald P, Chi H, Munger J, Green DR. The transcription factor Myc controls metabolic reprogramming upon T lymphocyte activation. Immunity. 2011;35(6):871-82.

Wang, Jiamian, John A. Jansen, and Fang Yang. "Electrospraying: possibilities and challenges of engineering carriers for biomedical applications-a mini review." Frontiers in Chemistry 7 (2019): 258.

Ward H, Vigues S, Poole S, Bristow AF. The rat interleukin 10 receptor: cloning and sequencing of cDNA coding for the alpha-chain protein sequence, and demonstration by western blotting of expression in the rat brain. Cytokine. 2001;15(5):237-40.

Wawman, Rebecca Ellen, Helen Bartlett, and Ye Htun Oo. "Regulatory T cell metabolism in the hepatic microenvironment." Frontiers in immunology 8 (2018): 1889.

Weber et al., "White Paper on Adoptive Cell Therapy for Cancer with Tumor-Infiltrating Lymphocytes: A Report of the CTEP Subcommittee on Adoptive Cell Therapy," Clinical Cancer Research, vol. 17, No. 7, pp. 1664-1673, Apr. 1, 2011.

Weiss RA, Weiss MA, Beasley KL, Munavalli G (2007) Autologous cultured fibroblast injection for facial contour deformities: a prospective, placebo-controlled, Phase III clinical trial. Dermatol Surg 33(3): 263-268.

Widdel, F. 2010. "Theory and measurement of bacterial growth" http://www.mpi-bremen.de/Binaries/Binary13037/Wachstumsversuch.pdf.

Yamada, Noriko, et al. "Thermo?responsive polymeric surfaces; control of attachment and detachment of cultured cells." Die Makromolekulare Chemie, Rapid Communications 11.11 (1990): 571-576.

Yoshinari, Masao, et al. "Effect of cold plasma-surface modification on surface wettability and initial cell attachment." International Journal of Biomedical and Biological Engineering 3.10 (2009): 507-511.

Zappasodi et al., "The Effect Of Artificial Antigen-Presenting Cells with Preclustered Anit-CD28/-CD3/LFA-1 Monoclonal Antibodies on the Induction of ex vivo Expansion of Functional Human Antitumor T Cells," Haematologica, vol. 93, No. 10, pp. 1523-1534, 2008.

Zemmour D, Zilionis R, Kiner E, Klein AM, Mathis D, Benoist C. Publisher Correction: Single-cell gene expression reveals a landscape of regulatory T cell phenotypes shaped by the TCR. Nat Immunol. 2018;19(6):645.

Zeng B, Kwak-Kim J, Liu Y, Liao AH. Treg cells are negatively correlated with increased memory B cells in pre-eclampsia while maintaining suppressive function on autologous B-cell proliferation. Am J Reprod Immunol. 2013;70(6):454-63.

\* cited by examiner

PASSIVE REPLACEMENT OF MEDIA

CROSS-REFERENCE TO RELATED APPLICATION

This application is a divisional application of, and claims priority to, U.S. patent application Ser. No. 14/668,659, entitled, "Passive Replacement of Media," filed on Mar. 25, 2015, which claims the benefit of U.S. Provisional Application Ser. No. 61/970,274, filed on Mar. 25, 2014, and entitled, "Passive Replacement of Media." The disclosures of the above-identified applications are hereby incorporated by reference in their entireties as if set forth herein in full for all that they teach and for all purposes.

BACKGROUND

Cell Expansion Systems (CESs) are used to expand and differentiate cells. Cell expansion systems may be used to expand, e.g., grow, stem cells, such as mesenchymal stem cells, human mesenchymal stem cells, etc. Cell expansion systems may also expand other types of cells, such as bone marrow cells, for example. Stem cells which are expanded from donor cells may be used to repair or replace damaged or defective tissues and have broad clinical applications for a wide range of diseases. Cells, of both adherent and non-adherent type, may be grown in a bioreactor in a cell expansion system.

SUMMARY

Embodiments of the present disclosure generally relate to using the passive replacement of media in a cell expansion system to conserve media and provide an environment conducive to encouraging cell growth. The expansion of cells, such as human mesenchymal stem cells, for example, uses external chemical signaling between the cells to initiate cell expansion by inhibiting lag phase signaling pathways internal to the cells. The expansion of other types of cells, such as Chinese hamster ovary (CHO) cells, for example, may be particularly sensitive to chemical signaling between the cells, according to embodiments. For example, CHO cells secrete cholecystokinin (CCK), a regulatory hormone responsible in part for cell culture maintenance and proliferation via chemical signaling. In embodiments, CCK may be small enough to pass through the microporous membrane of a hollow fiber bioreactor. Due to such ability to pass through the membrane, dilution of chemical signaling may occur regardless of inlet media addition to the intracapillary or extracapillary loop of a cell expansion system. To reduce or prevent the dilution of external chemical signaling in a closed, automated cell expansion system and, thus, reduce the lag phase of the cells, aspects of particular embodiments provide for passively replacing media by interrupting protocol procedures being executed and replacing a waste or outlet bag(s) used with the cell expansion system with a media bag(s). In embodiments, a bag containing base media may be attached to a waste line of the cell expansion system, in which such configuration allows base media to be added to the system at the rate of evaporation during conditions of no active inlet fluid flow. In embodiments, other types of replacement fluids are used in the media bag(s), such as, for example, complete media or cytokines or other cell-signaling protein molecules. In other embodiments, fluid may be passively replaced by interrupting protocol procedures being executed and allowing any fluid in the waste or outlet bag (assuming no constituents toxic to cell growth are present in the waste or outlet bag) to be passively added to the system at the rate of evaporation during conditions of no active inlet fluid flow. The passive addition of fluid avoids adding an excess amount of fluid, in which an excess amount of fluid may dilute the chemical signaling used to initiate cell expansion. Further, media constituents themselves may ultimately be conserved, resulting in increased system efficiencies and a savings of resources.

Embodiments of the present disclosure further relate to enhancing chemical signaling by adding a molecule(s), e.g. cell-signaling protein molecules, such as cytokines, according to embodiments, to the expanding cell population in a bioreactor. In an embodiment, cytokines, or other type of cell-signaling protein molecules, may be added to the bioreactor by, for example, welding a tubing line or other material connected to a cytokine source, or pre-filled with cytokines or other desired constituents, to a sampling coil or sample coil of the cell expansion system. The cytokines may thus be added to the bioreactor at the sample coil. Such direct addition results in a significant savings of cytokines, which may be costly, because a much higher amount of cytokines would need to be added to a media bag to compensate for dilution of the cytokines by the media than are needed when only the cytokine source itself replenishes the bioreactor. Further, cytokines tend to degrade quickly over time or with exposure to ultra-violet (UV) light, in which such degradation may be minimized by adding cytokines closer to the expanding cell population, e.g., at the sample coil of the bioreactor itself which is isolated from UV light sources. In such embodiments, the cytokines in the bioreactor may thus be maintained at a certain level while conserving resources.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, or A, B and C together.

This Summary is included to provide a selection of concepts in a simplified form, in which such concepts are further described below in the Detailed Description. This Summary is not intended to be used in any way to limit the claimed subject matter's scope. Features, including equivalents and variations thereof, may be included in addition to those provided herein.

BRIEF DESCRIPTION OF THE DRAWINGS

Embodiments of the present disclosure may be described by referencing the accompanying figures. In the figures, like numerals refer to like items.

DETAILED DESCRIPTION

Figure 1:
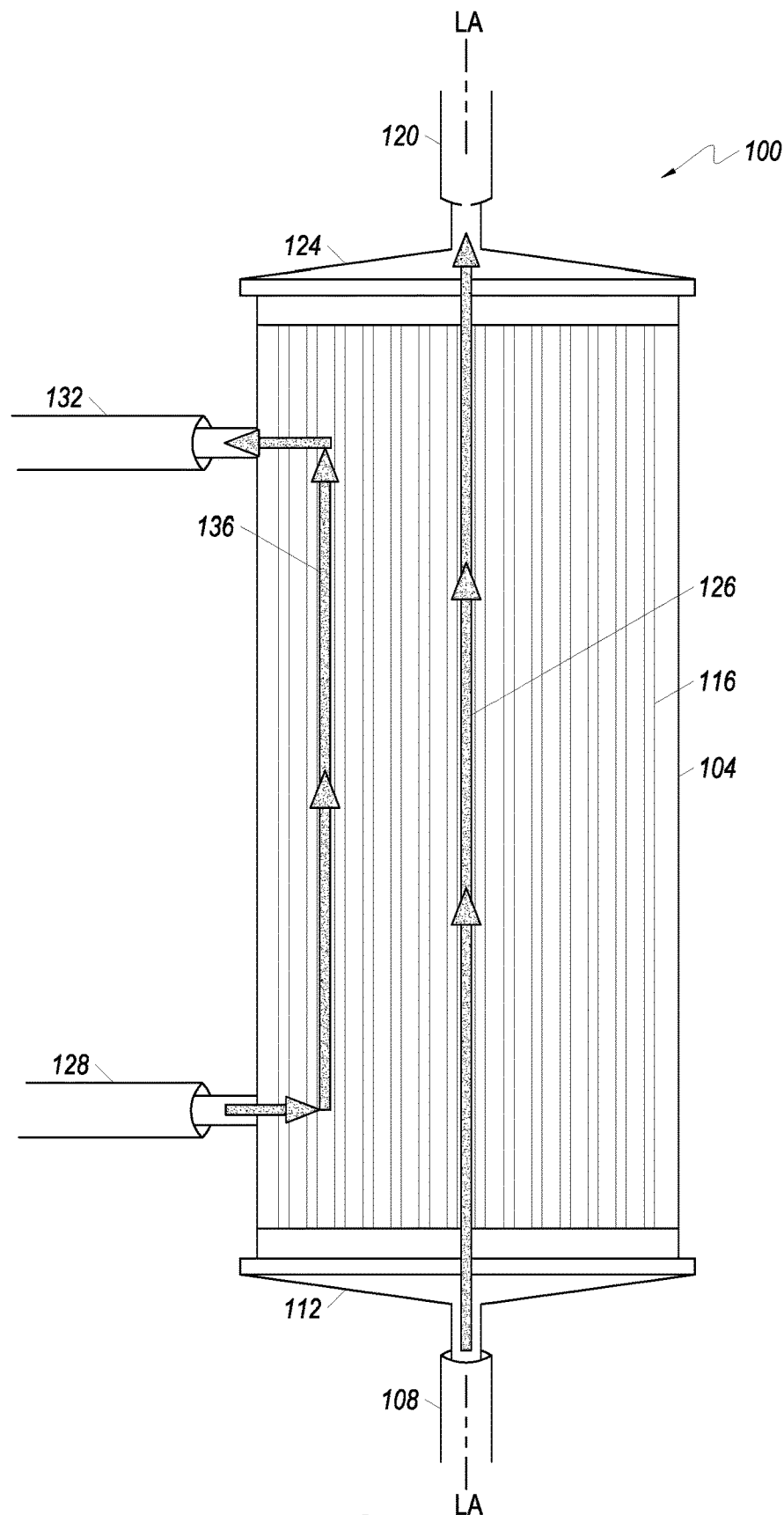
FIG. 1 depicts a perspective view of a hollow fiber bioreactor, in accordance with embodiments of the present disclosure.

The following Detailed Description provides a discussion of illustrative embodiments with reference to the accompanying drawings. The inclusion of specific embodiments herein should not be construed as limiting or restricting the present disclosure. Further, while language specific to features, acts, and/or structures, for example, may be used in describing embodiments herein, the claims are not limited to the features, acts, and/or structures described. A person of skill in the art will appreciate that other embodiments, including improvements, are within the spirit and scope of the present disclosure.

Embodiments of the present disclosure are generally directed to systems and methods for passively replacing media in a cell expansion system. Passive replacement of media may be accomplished by interrupting one or more protocol procedures being executed with respect to the system, e.g., cell loading, cell feeding, etc., and replacing a waste or outlet bag(s) used with the system with a media bag(s). By interrupting, or stopping, mechanisms of the cell expansion system from operating according to the protocol being executed, active inlet fluid flow to the system may be halted to reduce or prevent the dilution of chemical signaling used to inhibit the internal signaling pathways that keep a cell population in the lag phase in a bioreactor of the closed system. Reducing or preventing such dilution may thus reduce the lag phase of cell growth. More efficient and increased cell expansion may therefore occur, in which a greater number of cells may be expanded in a shorter amount of time, according to embodiments of the present disclosure.

Dilution of chemical signaling may occur where an inlet fluid flow into a cell expansion system overcompensates for the evaporation of fluid from the system. For example, an oxygenator or gas transfer module may be used in a closed cell expansion system to maintain the media in fibers in the bioreactor with a desired gas concentration, e.g., 5% $CO_2$, 20% $O_2$, 75% $N_2$. As an example, evaporation in the gas transfer module may occur at 14 mL/day. Without any inlet flow, such evaporation could result in either a build-up of air in the system or a back-flow of fluid from the waste or outlet line in embodiments where the waste line is the only source of fluid for the system which is not occluded by a pump, for example. Using an inlet flow, however, to account for such evaporation may result in overcompensating for the actual amount of fluid lost due to evaporation. For example, in an embodiment, the inlet flow rate into the cell expansion system may have a minimum flow rate. As an example, the inlet flow rate may be set at a minimum rate of 0.1 mL/min or 144 mL/day. Where evaporation in the gas transfer module occurs at 14 mL/day, the fluid lost due to evaporation may be overcompensated for by a rate of 130 mL/day in such embodiment. Such excess 130 mL/day dilutes chemical signaling for initiating cell expansion. For example, such dilution may occur in embodiments where chemical signaling molecules are able to cross, or pass through, a hollow fiber membrane from an intracapillary to an extracapillary side. As a result, adding replacement fluid to either the intracapillary or extracapillary side may result in dilution of the chemical signaling molecules by preventing or reducing them from building up by continuously adding fluid into the system. Where such dilution occurs, communication between the chemical signaling cells may be significantly impacted such that the cells may be unable to expand or even survive. Such dilution may have a particularly significant impact with respect to some cell types as compared to others. For example, reducing or preventing the dilution of chemical signaling molecules may have a significant impact on the expansion of Chinese hamster ovary (CHO) cells, according to embodiments.

In embodiments, instead of using an active inlet fluid flow which may unduly overcompensate for the evaporation of fluid from the system, the active inlet fluid flow to the system may be halted to prevent or minimize the dilution of chemical signaling used to inhibit the signaling pathways that maintain the cell population in a bioreactor in the lag phase. Such active inlet fluid flow may be halted, for example, by interrupting, or stopping, system mechanisms from operating according to the protocol(s) being executed. Instead of using an overcompensating active inlet fluid flow, such active inlet fluid flow may therefore be stopped while using a passive replacement of media and, therefore, not result in a build-up of air or back-flow of waste. To accomplish such passive media replacement, fluid, e.g., base media, may be added to the system at a rate equal to the rate of evaporation from the system, e.g., such as the rate of evaporation from a gas transfer module, through the use of one or more media bags used to replace one or more waste or outlet bags normally used with the system. The active inlet fluid flow may therefore be stopped while media from the replacement, or substitute, media bag replaces any fluid lost from the system due to evaporation. Such passive addition of fluid avoids adding an excess amount of fluid, in which an excess amount of fluid may dilute the chemical signaling used to initiate cell expansion. As a result, lost fluid may be replaced by adding media at about the rate of evaporation and without diluting chemical signaling used to inhibit signaling pathways that keep the cell population in the lag phase. The lag phase of cell growth may therefore be significantly reduced. Further, media constituents themselves may ultimately be conserved, resulting in increased system efficiencies and a savings of resources.

In other embodiments, fluid may be passively replaced by interrupting protocol procedures being executed and allowing any fluid in the waste or outlet bag (assuming no constituents toxic to cell growth are present in the waste or outlet bag) to be passively added to the system at the rate of evaporation during conditions of no active inlet fluid flow.

The dilution of chemical signaling may be particularly costly where the cell media includes expensive additives. For example, cell-signaling proteins, e.g., cytokines, may be used in the bioreactor to spur cell growth. Diluting cytokines may thus result in significant costs. Accordingly, saving the excess media, e.g., 130 mL/day, may provide significant cost savings over other cell expansion processes. Instead of using an overcompensating active inlet fluid flow, the passive replacement of media may thus be used, according to embodiments of the present disclosure, to maintain media constituent concentrations and conserve media in general. Further, in embodiments, other types of replacement fluids are used in the media bag(s), such as, for example, a media bag comprising cytokines or other cell-signaling protein molecules.

In embodiments, molecules, such as cell-signaling protein molecules, may be added to the bioreactor from a source of such molecules. For example, tubing or other material connected to a molecule source, such as a cytokine source, may be sterile-welded to a sample coil in the cell expansion system, and cytokines in the bioreactor may be replenished by such direct source of cytokines. In an embodiment, such tubing or other material comprises an additional volume added to the sampling coil. In another embodiment, such tubing or other material comprises a segment of tubing or other material used to replace a corresponding segment, or portion, of the sampling coil. In embodiments, such tubing or other material may be pre-filled with the desired constituents, e.g., cytokines. In another embodiment, such tubing or material may be connected to a container or bag comprising such desired constituents. A source of cytokines conserves the amount of cytokines used because the cytokines are not added to an IC media bag, for example, which could dilute the cytokines and use a larger amount of cytokines to achieve the same replenishment concentrations. Further, the cytokines may be added closer to the expanding cell population to minimize degradation of the cytokines. Degradation of the cytokines increases with exposure time to the media bags and UV light where they may be stored. Where cytokines are added closer to the expanding cell population, such degradation may be reduced because the cytokines reach the expanding cell population in a shorter amount of time in an environment protected from any sources of UV light. Such cytokines may be passively or actively added to the bioreactor, according to embodiments, to enhance chemical signaling capabilities. For example, such passive addition of cytokines may occur where the cytokines are added to the system from a media bag used to replace a waste bag, according to an embodiment, at the rate of evaporation during conditions of no active inlet fluid flow.

In an embodiment, chemical signaling may thus be controlled by the addition of cytokines at the sample coil. In another embodiment, chemical signaling may be controlled through such addition of cytokines at the sample coil coupled with the replacement of a waste bag(s) with a media bag(s). By replacing a waste bag(s) with a media bag(s), dilution in the bioreactor may be significantly reduced, as discussed above. Such dilution may be particularly costly where cytokines are used in the cell population expansion in the bioreactor. Preventing or reducing such dilution through the use of the media bag replacement thus may result in significant savings, according to embodiments.

In embodiments, a method provides for controlling chemical signaling in a bioreactor of a closed cell expansion system that includes a disposable tubing set(s). In such embodiments, the method may include the steps of coating the bioreactor and loading cells from a cell inlet bag into the bioreactor. For example, steps for loading cells with circulating distribution may be performed, according to an embodiment. In another embodiment, steps involving the loading of cells with uniform suspension, for example, may be performed. The cells may then be distributed across a membrane of the bioreactor by activating an intracapillary circulation pump, for example. In embodiments, after the loading and the distributing, a waste bag attached to the cell expansion system may be replaced with a media bag. After the waste bag is replaced, one or more pumps, e.g., an intracapillary circulation pump, extracapillary inlet pump, and intracapillary inlet pump, may be turned "OFF" or otherwise deactivated, according to an embodiment. In another embodiment, one or more pumps may be turned "OFF" or otherwise deactivated before replacing the outlet or waste bag. For example, in an embodiment expanding adherent cells, the intracapillary circulation pump may be deactivated after replacing a waste or outlet bag with a media bag. In another embodiment expanding adherent cells, for example, the intracapillary circulation pump may be deactivated before replacing the waste or outlet bag with a media bag. In yet other embodiments expanding non-adherent cells, for example, the intracapillary circulation pump may stay activated while one or more other pumps are deactivated.

In at least one embodiment, the media from the media bag flows through an extracapillary waste valve to the extracapillary circulation loop to replenish fluid evaporated from a gas transfer module in the extracapillary circulation loop. In embodiments, after replacement of the waste bag with the media bag, the method further includes deactivating an intracapillary inlet pump, deactivating an extracapillary inlet pump, maintaining an extracapillary circulation pump in an activated state, and maintaining the extracapillary waste valve in an open position.

In some embodiments, the cells include adherent cells, and the method may include the additional steps of enabling the adherent cells to attach to the bioreactor membrane and maintaining flow on an extracapillary circulation loop by maintaining an extracapillary circulation pump in an activated state. In some embodiments, the adherent cells are allowed to attach to the bioreactor membrane for a period of time, e.g., a first period of time, of about eighteen (18) hours to about twenty-four (24) hours. In other embodiments, the cells include non-adherent or suspension cells, such as, for example, CHO cells.

The method, in some embodiments, may further include feeding the cells in the bioreactor of the closed cell expansion system while maintaining the media bag in replacement of the waste bag and while reducing an intracapillary inlet rate. In these embodiments, feeding may include activating the intracapillary circulation pump. In embodiments, the feeding of the cells may be stopped after a second period of time of about forty-five (45) hours to about fifty (50) hours of feeding. In yet other embodiments, the feeding may be stopped after a second period of time of about forty-eight (48) hours of feeding.

The method, in embodiments, further involves measuring a concentration of lactate generated from the cells and stopping the feeding of the cells when the concentration of lactate is equal to or greater than about 6 mmol/L. In some embodiments, the method includes removing the media bag, inserting the waste bag, activating the intracapillary inlet pump, activating the intracapillary circulation pump, and maintaining an extracapillary circulation pump in an activated state. The intracapillary inlet pump may operate at an intracapillary inlet rate of about 0.1 mL/min, in some embodiments. The intracapillary circulation pump may operate at an intracapillary circulation rate of about 20 mL/min, in some embodiments. The extracapillary circulation pump may operate at an extracapillary circulation rate of about 30 mL/min, according to embodiments. In an embodiment, the method may additionally involve doubling, or otherwise increasing, according to other embodiments, the intracapillary inlet rate until a desired number of the cells are available for harvest. When the desired number of cells is available for harvest, embodiments include the additional steps of: releasing the cells from the membrane of the bioreactor, suspending the cells in the intracapillary circulation loop, and transferring the cells in suspension to a harvest bag.

Steps performed, including, for example, coating the bioreactor, loading cells, and distributing the cells, may be performed automatically in some embodiments, such as by a processor executing pre-programmed tasks stored in memory. Replacing a waste bag with a media bag may be performed manually in some embodiments and automatically in others. The automatic replacement of the waste bag may include, in embodiments, receiving, by a processor, a command to execute a task for replacing the waste bag, the task being stored in a memory. In an embodiment, for example, upon receiving such a command for the bag replacement, a processor may send a signal to close a valve(s), for example, for the waste bag and open another valve(s) for an attached media bag. In another embodiment, a single valve, or other type of mechanism, may control the flow of fluid from the waste bag or attached media bag.

The media bag may store base media and, in some embodiments, stores about 500 mL of base media, for example. The base media may include a number of different components, including, for example, glucose to provide an energy source for cells to grow, according to an embodiment. The media bag may comprise other fluids and/or constituents in accordance with embodiments of the present disclosure.

Other embodiments of the method provide for additional steps, some of which include loading cell-signaling protein molecules into a sample coil of an intracapillary circulation loop and activating the intracapillary circulation pump to transfer the cell-signaling protein molecules to the bioreactor. In some embodiments, the sample coil and the intracapillary circulation loop are part of a disposable tubing set.

In embodiments, the method may further include, prior to loading cells into the bioreactor, replacing fluid on an intracapillary circulation loop and on an extracapillary circulation loop with media from an intracapillary media bag, and allowing the media from the intracapillary media bag to reach equilibrium with a gas supply.

Some embodiments are directed to a cell expansion system, as noted above. In embodiments, such cell expansion system is closed, in which a closed cell expansion system comprises contents that are not directly exposed to the atmosphere. Such cell expansion system may be automated. In embodiments, cells, of both adherent and non-adherent type, may be grown in a bioreactor in the cell expansion system. According to embodiments, the cell expansion system may include base media. Methods for replenishment of media are provided for cell growth occurring in a bioreactor of the closed cell expansion system. In embodiments, the bioreactor used with such systems may be a hollow fiber bioreactor. Many types of bioreactors may be used in accordance with embodiments of the present disclosure.

The system may include, in embodiments, a bioreactor that further includes a first fluid flow path having at least opposing ends, a first opposing end of the first fluid flow path fluidly associated with a first port of a hollow fiber membrane and a second end of the first fluid flow path fluidly associated with a second port of the hollow fiber membrane, wherein the first fluid flow path comprises an intracapillary portion of the hollow fiber membrane. The system may further include a fluid inlet path fluidly associated with the first fluid flow path, wherein the plurality of cells are introduced into the first fluid flow path through a first fluid inlet path. A first pump for circulating fluid in the first fluid flow path of the bioreactor may also be included. In embodiments, the system includes a controller, e.g., first controller, for controlling operation of the first pump. In an embodiment, the controller may be a computing system, including a processor, for example. The controller may be configured, in embodiments, to control the pump to circulate a fluid at a first rate within the first fluid flow path, and, when a waste bag in the cell expansion system is replaced with a media bag, the controller stops the circulation of the fluid within the first fluid flow path after the plurality of the cells are loaded into the bioreactor. In some embodiments, a second pump for transferring intracapillary inlet fluid from an intracapillary media bag to the first fluid flow path and a controller, e.g., second controller, for controlling operation of the second pump are included. The second controller in embodiments controls the second pump to transfer cells from a cell inlet bag to the first fluid flow path, and when a waste bag in the cell expansion system is replaced with a media bag, stop the transfer of the cells from the cell inlet bag after the plurality of the cells are loaded into the bioreactor. Additional controllers, e.g., third controller, fourth controller, fifth controller, sixth controller, etc., may be used in accordance with embodiments. Further, additional pumps, e.g., third pump, fourth pump, fifth pump, sixth pump, etc., may be used in accordance with embodiments of the present disclosure. In addition, while the present disclosure may refer to a media bag, a waste bag, a cell inlet bag, etc., multiple bags, e.g., a first media bag, a second media bag, a third media bag, a first waste bag, a second waste bag, a third waste bag, a first cell inlet bag, a second cell inlet bag, a third cell inlet bag, etc., or other types of containers, may be used in embodiments. In other embodiments, a single media bag, a single waste bag, a single cell inlet bag, etc., may be used.

In embodiments, the system may be controlled by, for example: a processor coupled to the cell expansion system; a display device, in communication with the processor, and operable to display data; and a memory, in communication with and readable by the processor, and containing a series of instructions. In embodiments, when the instructions are executed by the processor, the processor receives an instruction to coat the bioreactor, for example. In response to the instruction to coat the bioreactor, the processor may execute a series of steps to coat the bioreactor and may next receive an instruction to load cells into the bioreactor, for example. In response to the instruction to load cells, the processor may execute a series of steps to load the cells from a cell inlet bag into the bioreactor. After loading the cells into the bioreactor, the processor may receive an instruction to stop an intracapillary inlet pump, an intracapillary circulation pump, and an extracapillary inlet pump, for example. The cell expansion system may be operated to allow media to flow from a media bag through an extracapillary waste valve, wherein the extracapillary waste valve is in an open position. The processor may receive an instruction to pump the media in the extracapillary circulation loop to replace fluid evaporated from a gas transfer module located in the extracapillary circulation loop.

Referring to FIG. 1, an example of a hollow fiber cell growth chamber 100 which may be used with the present disclosure is shown in front side elevation view. Cell growth chamber 100 has a longitudinal axis LA-LA and includes cell growth chamber housing 104. In at least one embodiment, cell growth chamber housing 104 includes four openings or ports: IC inlet port 108, IC outlet port 120, EC inlet port 128, and EC outlet port 132.

According to embodiments of the present disclosure, fluid in a first circulation path enters cell growth chamber 100 through IC inlet port 108 at a first longitudinal end 112 of the cell growth chamber 100, passes into and through the intracapillary side (referred to in various embodiments as the intracapillary ("IC") side or "IC space" of a hollow fiber membrane) of a plurality of hollow fibers 116, and out of cell growth chamber 100 through IC outlet port 120 located at a second longitudinal end 124 of the cell growth chamber 100. The fluid path between the IC inlet port 108 and the IC outlet port 120 defines the IC portion 126 of the cell growth chamber 100. Fluid in a second circulation path flows in the cell growth chamber 100 through EC inlet port 128, comes in contact with the extracapillary side or outside (referred to as the "EC side" or "EC space" of the membrane) of the hollow fibers 116, and exits cell growth chamber 100 via EC outlet port 132. The fluid path between the EC inlet port 128 and the EC outlet port 132 comprises the EC portion 136 of the cell growth chamber 100. Fluid entering cell growth chamber 100 via the EC inlet port 128 may be in contact with the outside of the hollow fibers 116. Small molecules (e.g., ions, water, oxygen, lactate, etc.) may diffuse through the hollow fibers 116 from the interior or IC space of the hollow fiber to the exterior or EC space, or from the EC space to the IC space. Large molecular weight molecules, such as growth factors, are typically too large to pass through the hollow fiber membrane, and remain in the IC space of the hollow fibers 116. The media may be replaced as needed, in embodiments. Media may also be circulated through an oxygenator or gas transfer module to exchange gasses as needed. Cells may be contained within a first circulation path and/or a second circulation path, as described below, and may be on either the IC side and/or EC side of the membrane, according to embodiments.

The material used to make the hollow fiber membrane may be any biocompatible polymeric material which is capable of being made into hollow fibers. One material which may be used is a synthetic polysulfone-based material, according to an embodiment of the present disclosure. In order for the cells to adhere to the surface of the hollow fibers, the surface may be modified in some way, either by coating at least the cell growth surface with a protein such as fibronectin or collagen, or by exposing the surface to radiation. Gamma treating the membrane surface allows for attachment of adherent cells without additionally coating the membrane with fibronectin or the like. Bioreactors made of gamma treated membranes may be reused. Other coatings and/or treatments for cell attachment may be used in accordance with embodiments of the present disclosure.

Figure 2:
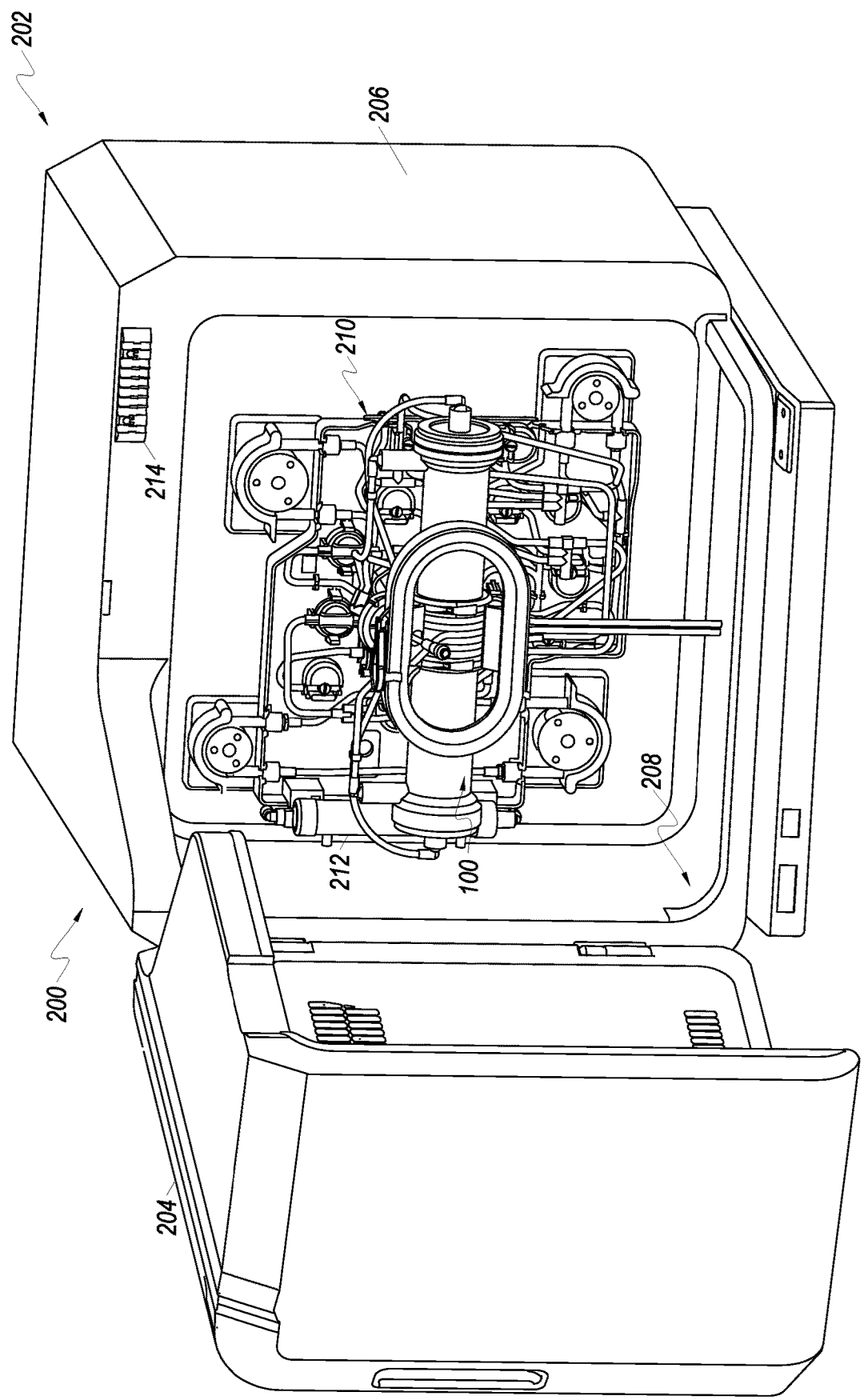
FIG. 2 illustrates a perspective view of a cell expansion system with a premounted fluid conveyance device, in accordance with embodiments of the present disclosure.

Turning to FIG. 2, an embodiment of a cell expansion system 200 with a premounted fluid conveyance assembly is shown in accordance with embodiments of the present disclosure. The CES 200 includes a cell expansion machine 202 that comprises a hatch or closable door 204 for engagement with a back portion 206 of the cell expansion machine 202. An interior space 208 within the cell expansion machine 202 includes features adapted for receiving and engaging a premounted fluid conveyance assembly 210. The premounted fluid conveyance assembly 210 may be detachably-attachable to the cell expansion machine 202 to facilitate relatively quick exchange of a new or unused premounted fluid conveyance assembly 210 at a cell expansion machine 202 for a used premounted fluid conveyance assembly 210 at the same cell expansion machine 202. A single cell expansion machine 202 may be operated to grow or expand a first set of cells using a first premounted fluid conveyance assembly 210 and, thereafter, may be used to grow or expand a second set of cells using a second premounted fluid conveyance assembly 210 without needing to be sanitized between interchanging the first premounted fluid conveyance assembly 210 for the second premounted fluid conveyance assembly 210. The premounted fluid conveyance assembly includes a bioreactor 100 and an oxygenator or gas transfer module 212. Tubing guide slots are shown as 214 for receiving various media tubing connected to premounted fluid conveyance assembly 210, according to embodiments.

Figure 3:
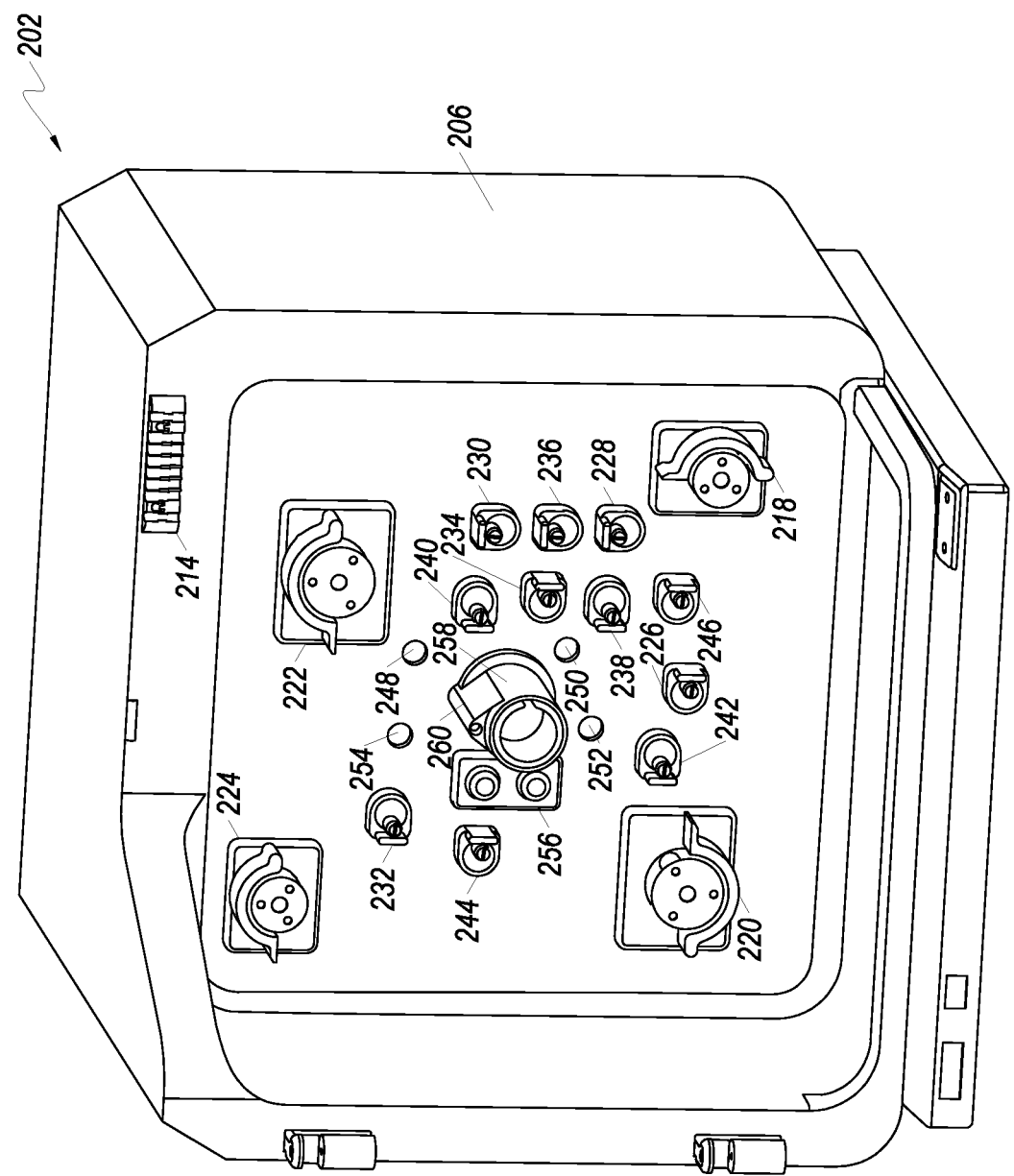
FIG. 3 depicts a perspective view of a housing of a cell expansion system, in accordance with embodiments of the present disclosure.

Next, FIG. 3 illustrates the back portion 206 of cell expansion machine 202 prior to detachably-attaching a premounted fluid conveyance assembly 210 (FIG. 2), in accordance with embodiments of the present disclosure. The closable door 204 (shown in FIG. 2) is omitted from FIG. 3. The back portion 206 of the cell expansion machine 202 includes a number of different structures for working in combination with elements of a premounted fluid conveyance assembly 210. More particularly, the back portion 206 of the cell expansion machine 202 includes a plurality of peristaltic pumps for cooperating with pump loops on the premounted fluid conveyance assembly 210, including the IC circulation pump 218, the EC circulation pump 220, the IC inlet pump 222, and the EC inlet pump 224. In addition, the back portion 206 of the cell expansion machine 202 includes a plurality of valves, including the IC circulation valve 226, the reagent valve 228, the IC media valve 230, the air removal valve 232, the cell inlet valve 234, the wash valve 236, the distribution valve 238, the EC media valve 240, the IC waste valve 242, the EC waste valve 244, and the harvest valve 246. Several sensors are also associated with the back portion 206 of the cell expansion machine 202, including the IC outlet pressure sensor 248, the combination IC inlet pressure and temperature sensors 250, the combination EC inlet pressure and temperature sensors 252, and the EC outlet pressure sensor 254. Also shown is an optical sensor 256 for an air removal chamber.

In accordance with embodiments, a shaft or rocker control 258 for rotating the bioreactor 100 is shown. Shaft fitting 260 associated with the shaft or rocker control 258 allows for proper alignment of a shaft access aperture, see e.g., 424 (FIG. 4) of a tubing-organizer, see e.g., 300 (FIG. 4) of a premounted conveyance assembly 210 or 400 with the back portion 206 of the cell expansion machine 202. Rotation of shaft or rocker control 258 imparts rotational movement to shaft fitting 260 and bioreactor 100. Thus, when an operator or user of the CES 200 attaches a new or unused premounted fluid conveyance assembly 400 (FIG. 4) to the cell expansion machine 202, the alignment is a relatively simple matter of properly orienting the shaft access aperture 424 (FIG. 4) of the premounted fluid conveyance assembly 210 or 400 with the shaft fitting 260.

Figure 4:
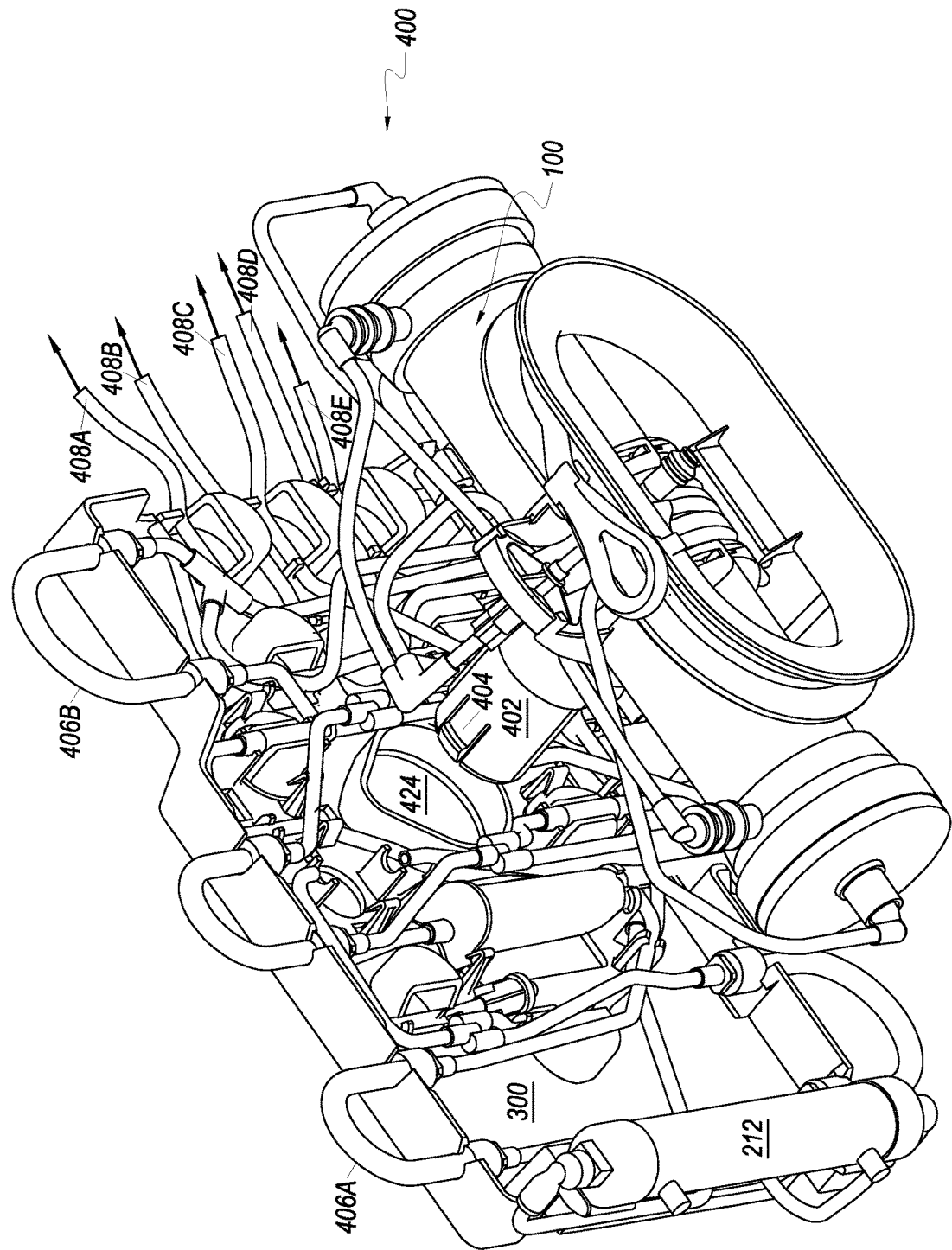
FIG. 4 illustrates a perspective view of a premounted fluid conveyance device, in accordance with embodiments of the present disclosure

Turning to FIG. 4, a perspective view of a detachably-attachable premounted fluid conveyance assembly 400 is shown. The premounted fluid conveyance assembly 400 may be detachably-attachable to the cell expansion machine 202 to facilitate relatively quick exchange of a new or unused premounted fluid conveyance assembly 400 at a cell expansion machine 202 for a used premounted fluid conveyance assembly 400 at the same cell expansion machine 202. As shown in FIG. 4, the bioreactor 100 may be attached to a bioreactor coupling that includes a shaft fitting 402. The shaft fitting 402 includes one or more shaft fastening mechanisms, such as a biased arm or spring member 404 for engaging a shaft, e.g., 258 (shown in FIG. 3), of the cell expansion machine 202.

According to embodiments, the premounted fluid conveyance assembly 400 includes tubing 408A, 408B, 408C, 408D, 408E, etc., and various tubing fittings to provide the fluid paths shown in FIGS. 5-9, as discussed below. Pump loops 406A and 406B are also provided for the pump(s). In embodiments, although the various media may be provided at the site where the cell expansion machine 202 is located, the premounted fluid conveyance assembly 400 may include sufficient tubing length to extend to the exterior of the cell expansion machine 202 and to enable welded connections to tubing associated with the media bags, according to embodiments.

Figure 5:
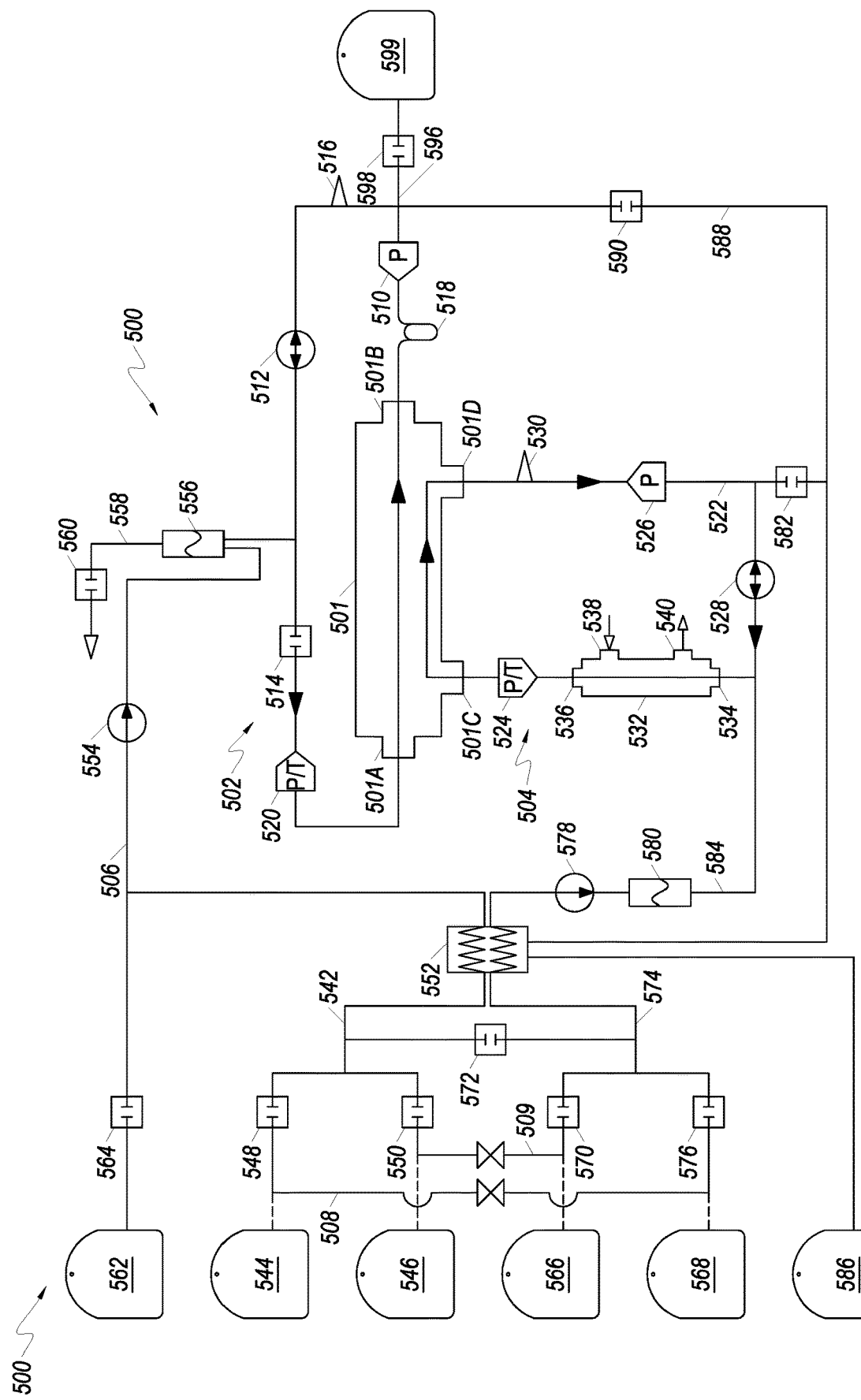
FIG. 5 depicts a schematic of a cell expansion system, in accordance with an embodiment of the present disclosure.
Figure 6:
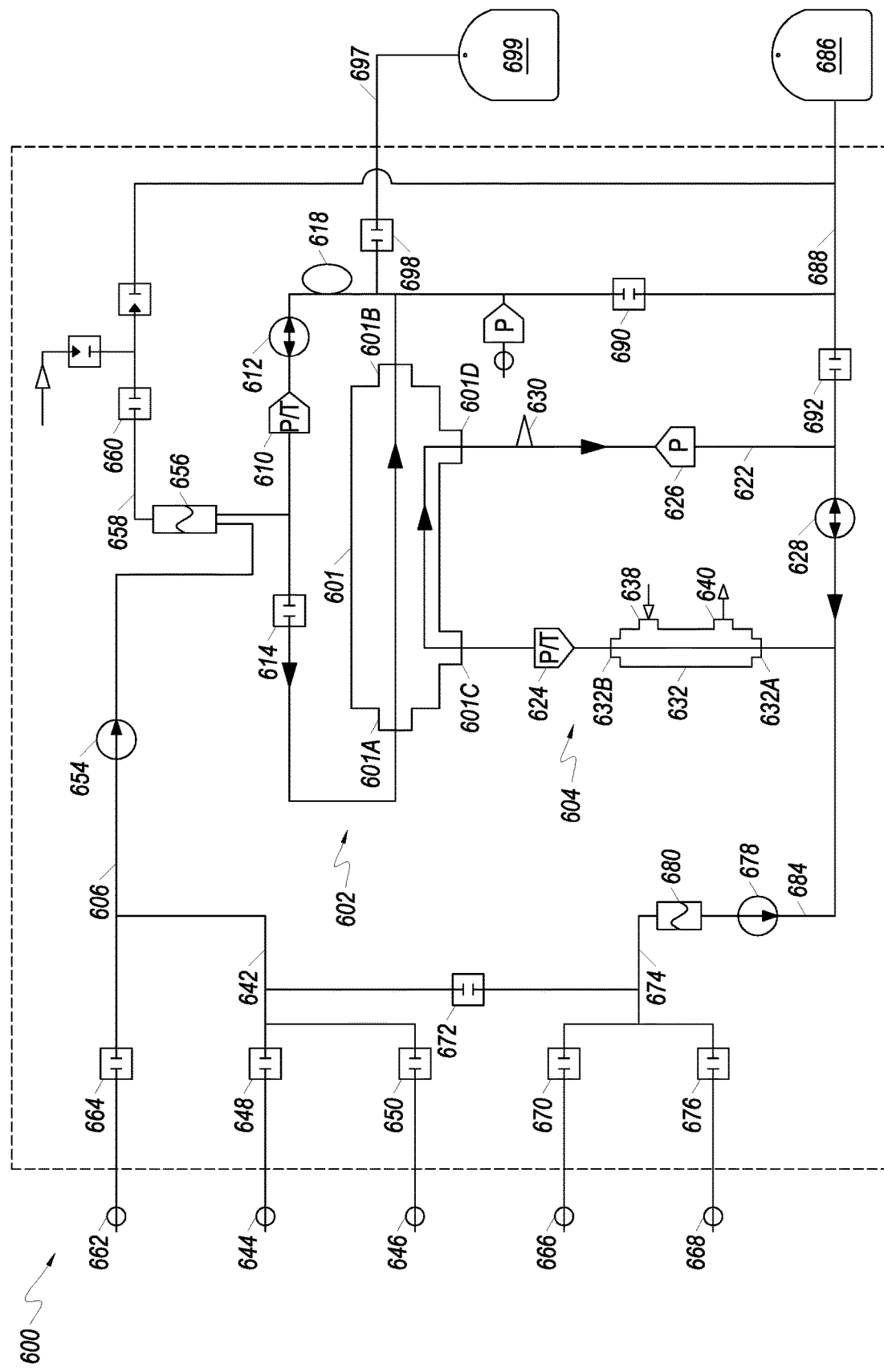
FIG. 6 illustrates a schematic of another embodiment of a cell expansion system.

FIG. 5 illustrates a schematic of an embodiment of a cell expansion system 500, and FIG. 6 illustrates a schematic of another embodiment of a cell expansion system 600. In the embodiments shown in FIGS. 5 and 6, and as described below, the cells are grown in the IC space. However, the disclosure is not limited to such examples and may in other embodiments provide for cells to be grown in the EC space.

FIG. 5 illustrates a CES 500, which includes first fluid circulation path 502 (also referred to as the "intracapillary loop" or "IC loop") and second fluid circulation path 504 (also referred to as the "extracapillary loop" or "EC loop"), according to embodiments. First fluid flow path 506 may be fluidly associated with cell growth chamber 501 to form first fluid circulation path 502. Fluid flows into cell growth chamber 501 through IC inlet port 501A, through hollow fibers in cell growth chamber 501, and exits via IC outlet port 501B. Pressure gauge 510 measures the pressure of media leaving cell growth chamber 501. Media flows through IC circulation pump 512 which may be used to control the rate of media flow. IC circulation pump 512 may pump the fluid in a first direction or second direction opposite the first direction. Exit port 501B may be used as an inlet in the reverse direction. Media entering the IC loop 502 may enter through valve 514. As those skilled in the art will appreciate, additional valves and/or other devices may be placed at various locations to isolate and/or measure characteristics of the media along portions of the fluid paths. Accordingly, it is to be understood that the schematic shown represents one possible configuration for various elements of the CES 500, and modifications to the schematic shown are within the scope of the one or more present embodiments.

With regard to the IC loop 502, samples of media may be obtained from sample port 516 or sample coil 518 during operation. Pressure/temperature gauge 520 disposed in first fluid circulation path 502 allows detection of media pressure and temperature during operation. Media then returns to IC inlet port 501A to complete fluid circulation path 502. Cells grown/expanded in cell growth chamber 501 may be flushed out of cell growth chamber 501 into harvest bag 599 through valve 598 or redistributed within the hollow fibers for further growth. This will be described in more detail below.

Fluid in second fluid circulation path 504 enters cell growth chamber 501 via EC inlet port 501C, and leaves cell growth chamber 501 via EC outlet port 501D. Media in the EC loop 504 may be in contact with the outside of the hollow fibers in the cell growth chamber 501, thereby allowing diffusion of small molecules into and out of the hollow fibers.

Pressure/temperature gauge 524 disposed in the second fluid circulation path 504 allows the pressure and temperature of media to be measured before the media enters the EC space of the cell growth chamber 501. Pressure gauge 526 allows the pressure of media in the second fluid circulation path 504 to be measured after it leaves the cell growth chamber 501. With regard to the EC loop, samples of media may be obtained from sample port 530 or a sample coil during operation.

In embodiments, after leaving EC outlet port 501D of cell growth chamber 501, fluid in second fluid circulation path 504 passes through EC circulation pump 528 to oxygenator or gas transfer module 532. EC circulation pump 528 may also pump the fluid in opposing directions. Second fluid flow path 522 may be fluidly associated with oxygenator or gas transfer module 532 via oxygenator inlet port 534 and oxygenator outlet port 536. In operation, fluid media flows into oxygenator or gas transfer module 532 via oxygenator inlet port 534, and exits oxygenator or gas transfer module 532 via oxygenator outlet port 536. Oxygenator or gas transfer module 532 adds oxygen to and removes bubbles from media in the CES 500. In various embodiments, media in second fluid circulation path 504 may be in equilibrium with gas entering oxygenator or gas transfer module 532. The oxygenator or gas transfer module 532 may be any appropriately sized oxygenator or gas transfer device. Air or gas flows into oxygenator or gas transfer module 532 via filter 538 and out of oxygenator or gas transfer device 532 through filter 540. Filters 538 and 540 reduce or prevent contamination of oxygenator or gas transfer module 532 and associated media. Air or gas purged from the CES 500 during portions of a priming sequence may vent to the atmosphere via the oxygenator or gas transfer module 532.

In the configuration depicted for CES 500, fluid media in first fluid circulation path 502 and second fluid circulation path 504 flows through cell growth chamber 501 in the same direction (a co-current configuration). The CES 500 may also be configured to flow in a counter-current conformation.

In accordance with at least one embodiment, media, including cells (from bag 562), and fluid media from bag 546 may be introduced to first fluid circulation path 502 via first fluid flow path 506. Fluid container 562 (e.g., Cell Inlet Bag or Saline Priming Fluid for priming air out of the system) may be fluidly associated with the first fluid flow path 506 and the first fluid circulation path 502 via valve 564.

Fluid containers, or media bags, 544 (e.g., Reagent) and 546 (e.g., IC Media) may be fluidly associated with either first fluid inlet path 542 via valves 548 and 550, respectively, or second fluid inlet path 574 via valves 570 and 576. First and second sterile sealable input priming paths 508 and 509 are also provided. An air removal chamber (ARC) 556 may be fluidly associated with first circulation path 502. The air removal chamber 556 may include one or more ultrasonic sensors including an upper sensor and lower sensor to detect air, a lack of fluid, and/or a gas/fluid interface, e.g., an air/fluid interface, at certain measuring positions within the air removal chamber 556. For example, ultrasonic sensors may be used near the bottom and/or near the top of the air removal chamber 556 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 500 during portions of the priming sequence or other protocols may vent to the atmosphere out air valve 560 via line 558 that may be fluidly associated with air removal chamber 556.

EC media (from bag 568) or wash solution (from bag 566) may be added to either the first or second fluid flow paths. Fluid container 566 may be fluidly associated with valve 570 that may be fluidly associated with first fluid circulation path 502 via distribution valve 572 and first fluid inlet path 542. Alternatively, fluid container 566 may be fluidly associated with second fluid circulation path 504 via second fluid inlet path 574 and EC inlet path 584 by opening valve 570 and closing distribution valve 572. Likewise, fluid container 568 may be fluidly associated with valve 576 that may be fluidly associated with first fluid circulation path 502 via first fluid inlet path 542 and distribution valve 572. Alternatively, fluid container 568 may be fluidly associated with second fluid inlet path 574 by opening valve 576 and closing valve distribution 572.

An optional heat exchanger 552 may be provided for media reagent or wash solution introduction.

In the IC loop, fluid may be initially advanced by the IC inlet pump 554. In the EC loop, fluid may be initially advanced by the EC inlet pump 578. An air detector 580, such as an ultrasonic sensor, may also be associated with the EC inlet path 584.

In at least one embodiment, first and second fluid circulation paths 502 and 504 are connected to waste line 588. When valve 590 is opened, IC media may flow through waste line 588 and to waste or outlet bag 586. Likewise, when valve 582 is opened, EC media may flow through waste line 588 to waste or outlet bag 586.

In embodiments, cells may be harvested via cell harvest path 596. Here, cells from cell growth chamber 501 may be harvested by pumping the IC media containing the cells through cell harvest path 596 and valve 598 to cell harvest bag 599.

Various components of the CES 500 may be contained or housed within a machine or housing, such as cell expansion machine 202 (FIGS. 2 and 3), wherein the machine maintains cells and media at a predetermined temperature.

Turning to FIG. 6, a schematic of another embodiment of a cell expansion system 600 is shown. CES 600 includes a first fluid circulation path 602 (also referred to as the "intracapillary loop" or "IC loop") and second fluid circulation path 604 (also referred to as the "extracapillary loop" or "EC loop"). First fluid flow path 606 may be fluidly associated with cell growth chamber 601 to form first fluid circulation path 602. Fluid flows into cell growth chamber 601 through IC inlet port 601A, through hollow fibers in cell growth chamber 601, and exits via IC outlet port 601B. Pressure sensor 610 measures the pressure of media leaving cell growth chamber 601. In addition to pressure, sensor 610 may, in embodiments, also be a temperature sensor that detects the media pressure and temperature during operation. Media flows through IC circulation pump 612 which may be used to control the rate of media flow. IC circulation pump 612 may pump the fluid in a first direction or second direction opposite the first direction. Exit port 601B may be used as an inlet in the reverse direction. Media entering the IC loop may enter through valve 614. As those skilled in the art will appreciate, additional valves and/or other devices may be placed at various locations to isolate and/or measure characteristics of the media along portions of the fluid paths. Accordingly, it is to be understood that the schematic shown represents one possible configuration for various elements of the CES 600, and modifications to the schematic shown are within the scope of the one or more present embodiments.

With regard to the IC loop, samples of media may be obtained from sample coil 618 during operation. Media then returns to IC inlet port 601A to complete fluid circulation path 602. Cells grown/expanded in cell growth chamber 601 may be flushed out of cell growth chamber 601 into harvest bag 699 through valve 698 and line 697. Alternatively, when valve 698 is closed, the cells may be redistributed within chamber 601 for further growth.

Fluid in second fluid circulation path 604 enters cell growth chamber 601 via EC inlet port 601C and leaves cell growth chamber 601 via EC outlet port 601D. Media in the EC loop may be in contact with the outside of the hollow fibers in the cell growth chamber 601, thereby allowing diffusion of small molecules into and out of the hollow fibers that may be within chamber 601, according to an embodiment.

Pressure/temperature sensor 624 disposed in the second fluid circulation path 604 allows the pressure and temperature of media to be measured before the media enters the EC space of the cell growth chamber 601. Sensor 626 allows the pressure and/or temperature of media in the second fluid circulation path 604 to be measured after it leaves the cell growth chamber 601. With regard to the EC loop, samples of media may be obtained from sample port 630 or a sample coil during operation.

After leaving EC outlet port 601D of cell growth chamber 601, fluid in second fluid circulation path 604 passes through EC circulation pump 628 to oxygenator or gas transfer module 632. EC circulation pump 628 may also pump the fluid in opposing directions, according to embodiments. Second fluid flow path 622 may be fluidly associated with oxygenator or gas transfer module 632 via an inlet port 632A and an outlet port 632B of oxygenator or gas transfer module 632. In operation, fluid media flows into oxygenator or gas transfer module 632 via inlet port 632A, and exits oxygenator or gas transfer module 632 via outlet port 632B. Oxygenator or gas transfer module 632 adds oxygen to and removes bubbles from media in the CES 600. In various embodiments, media in second fluid circulation path 604 may be in equilibrium with gas entering oxygenator or gas transfer module 632. The oxygenator or gas transfer module 632 may be any appropriately sized device useful for oxygenation or gas transfer. Air or gas flows into oxygenator or gas transfer module 632 via filter 638 and out of oxygenator or gas transfer device 632 through filter 640. Filters 638 and 640 reduce or prevent contamination of oxygenator or gas transfer module 632 and associated media. Air or gas purged from the CES 600 during portions of a priming sequence may vent to the atmosphere via the oxygenator or gas transfer module 632.

In the configuration depicted for CES 600, fluid media in first fluid circulation path 602 and second fluid circulation path 604 flows through cell growth chamber 601 in the same direction (a co-current configuration). The CES 600 may also be configured to flow in a counter-current conformation, according to embodiments.

In accordance with at least one embodiment, media, including cells (from a source such as a cell container, e.g. a bag) may be attached at attachment point 662, and fluid media from a media source may be attached at attachment point 646. The cells and media may be introduced into first fluid circulation path 602 via first fluid flow path 606. Attachment point 662 may be fluidly associated with the first fluid flow path 606 via valve 664, and attachment point 646 may be fluidly associated with the first fluid flow path 606 via valve 650. A reagent source may be fluidly connected to point 644 and be associated with fluid inlet path 642 via valve 648, or second fluid inlet path 674 via valves 648 and 672.

Air removal chamber (ARC) 656 may be fluidly associated with first circulation path 602. The air removal chamber 656 may include one or more sensors including an upper sensor and lower sensor to detect air, a lack of fluid, and/or a gas/fluid interface, e.g., an air/fluid interface, at certain measuring positions within the air removal chamber 656. For example, ultrasonic sensors may be used near the bottom and/or near the top of the air removal chamber 656 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 600 during portions of a priming sequence or other protocol(s) may vent to the atmosphere out air valve 660 via line 658 that may be fluidly associated with air removal chamber 656.

An EC media source may be attached to EC media attachment point 668 and a wash solution source may be attached to wash solution attachment point 666, to add EC media and/or wash solution to either the first or second fluid flow path. Attachment point 666 may be fluidly associated with valve 670 that may be fluidly associated with first fluid circulation path 602 via valve 672 and first fluid inlet path 642. Alternatively, attachment point 666 may be fluidly associated with second fluid circulation path 604 via second fluid inlet path 674 and second fluid flow path 684 by opening valve 670 and closing valve 672. Likewise, attachment point 668 may be fluidly associated with valve 676 that may be fluidly associated with first fluid circulation path 602 via first fluid inlet path 642 and valve 672. Alternatively, fluid container 668 may be fluidly associated with second fluid inlet path 674 by opening valve 676 and closing valve distribution 672.

In the IC loop, fluid may be initially advanced by the IC inlet pump 654. In the EC loop, fluid may be initially advanced by the EC inlet pump 678. An air detector 680, such as an ultrasonic sensor, may also be associated with the EC inlet path 684.

In at least one embodiment, first and second fluid circulation paths 602 and 604 are connected to waste line 688. When valve 690 is opened, IC media may flow through waste line 688 and to waste or outlet bag 686. Likewise, when valve 692 is opened, EC media may flow to waste or outlet bag 686.

After cells have been grown in cell growth chamber 601, they may be harvested via cell harvest path 697. Here, cells from cell growth chamber 601 may be harvested by pumping the IC media containing the cells through cell harvest path 697, with valve 698 open, into cell harvest bag 699.

Various components of the CES 600 may be contained or housed within a machine or housing, such as cell expansion machine 202 (FIGS. 2 and 3), wherein the machine maintains cells and media at a predetermined temperature. It is further noted that, in embodiments, components of CES 600 and CES 500 (FIG. 5) may be combined. In other embodiments, a CES may include fewer or additional components than those shown in FIGS. 5 and 6 and still be within the scope of the present disclosure.

Figure 7:
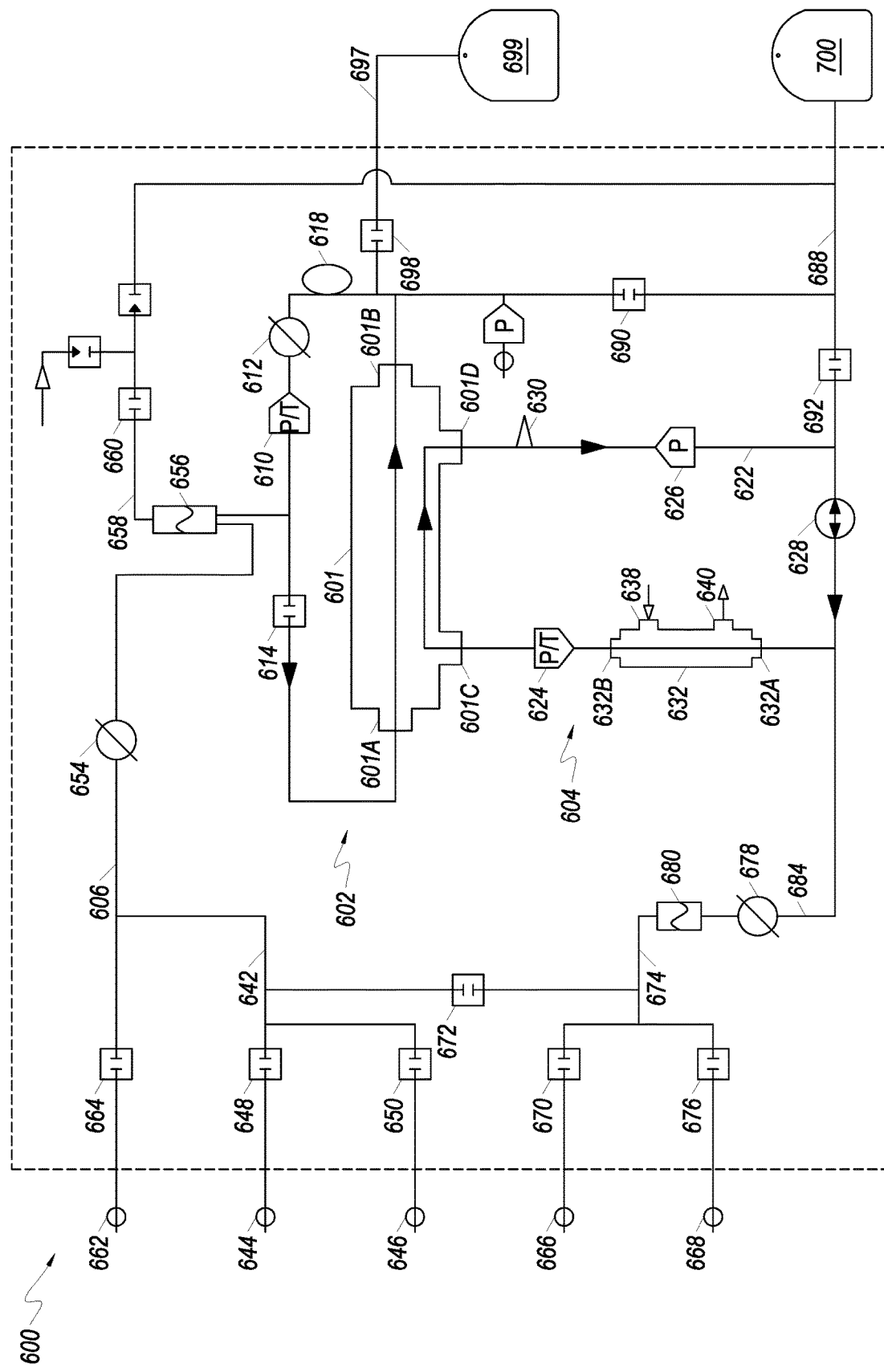
FIG. 7 depicts the cell expansion system embodiment of FIG. 6 with a waste bag replaced by a media bag, in accordance with embodiments of the present disclosure.
Figure 8:
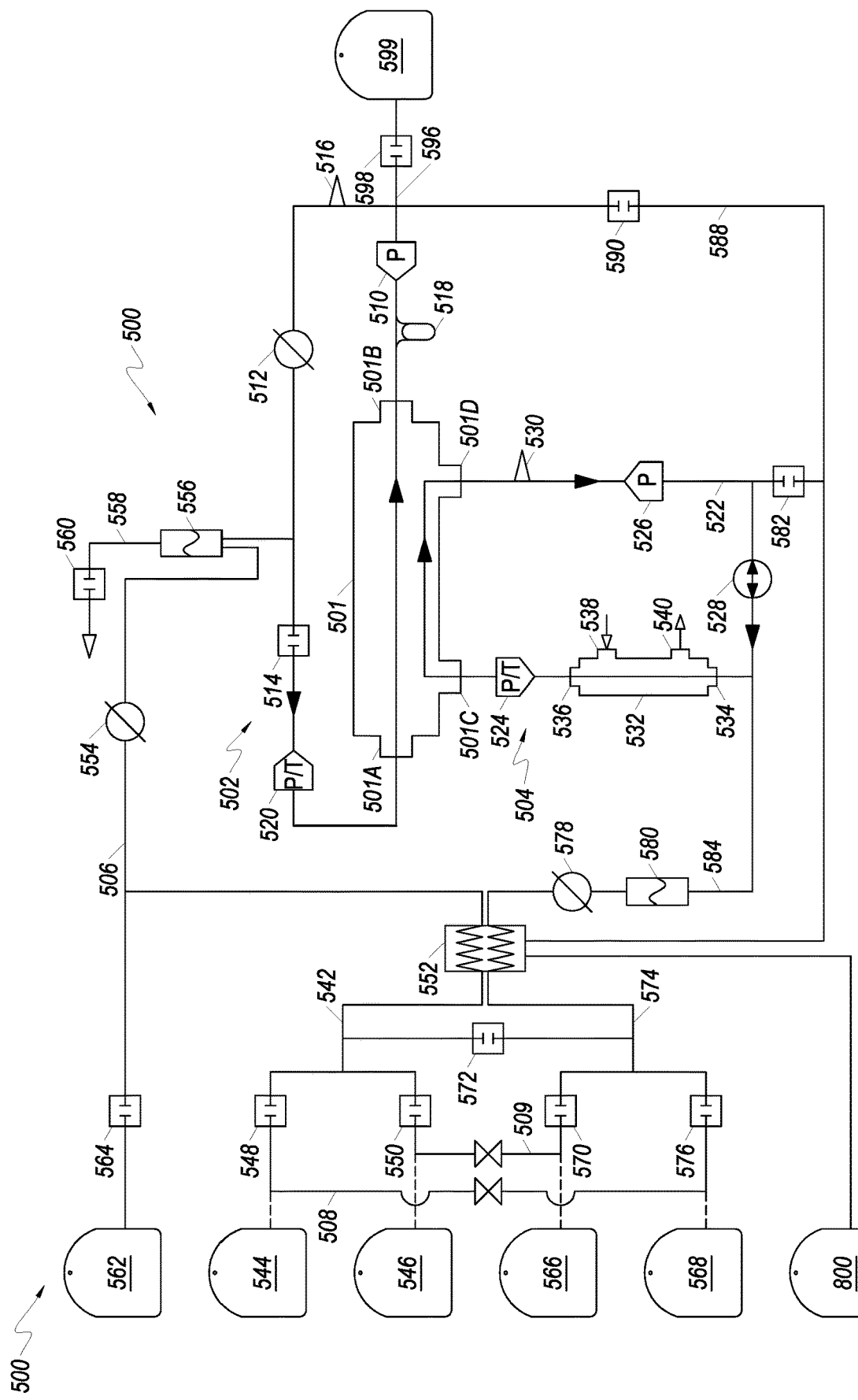
FIG. 8 illustrates the cell expansion system embodiment of FIG. 5 with a waste bag replaced by a media bag, in accordance with embodiments of the present disclosure.

While FIGS. 5 and 6 illustrate schematics of different embodiments of cell expansion systems, FIGS. 7 and 8 depict these same cell expansion systems with the waste or outlet bags (586 and 686) replaced by media bags in accordance with embodiments of the present disclosure. For example, as depicted in FIG. 7, waste or outlet bag 686 in CES 600 (FIG. 6) has been replaced by media, e.g., base media, bag 700. Further, one or more pumps, e.g., IC Circulation Pump 612, EC Inlet Pump 678, and IC Inlet Pump 654, have been turned "OFF," according to an embodiment. There is thus no active inlet fluid flow into cell growth chamber 601. To compensate for fluid lost due to evaporation at the oxygenator or gas transfer module 632, the EC Circulation Pump 628 is left "ON" and the EC Waste Valve 692 is left "OPEN." This configuration allows fluid from media bag 700 to backflow into the CES 600 system at a rate equal to the rate of evaporation from the oxygenator or gas transfer module 632. The fluid lost in the system due to evaporation may thus be replaced without diluting chemical signaling occurring in the bioreactor 601 during cell growth therein. In embodiments, the lag phase of cell growth in the bioreactor 601 may therefore be significantly reduced, and more efficient cell expansion may occur. Further, by turning "OFF," or otherwise deactivating, the inlet pump(s), system resources may be conserved because there is no active inlet fluid being unnecessarily introduced into the system. While FIG. 7 shows an embodiment in which the IC Circulation Pump 612, EC Inlet Pump 678, and IC Inlet Pump 654 have been turned "OFF," other embodiments provide for one or more of such pumps, e.g., the IC Circulation Pump 612, for example, to remain "ON" or activated (not shown in FIG. 7). For example, it may be desired in embodiments to continue circulation in the intracapillary side depending on the type of cells, e.g., non-adherent cells, being expanded, according to an embodiment.

In some embodiments, the media bag (e.g., 700) may be positioned at a physically higher level than at least a portion of the EC loop 604 to allow gravity to assist in draining fluid from the media bag into the EC loop 604. In some embodiments, the waste bag 686 (FIG. 6) may be positioned lower than the EC loop 604 to allow gravity to assist in draining waste media into the waste bag 686. According to embodiments, when the media bag 700 replaces the waste bag 686, the substitute or replacement media bag 700 may be positioned physically higher than the original position of the waste bag 686.

Turning to FIG. 8, a similar configuration is shown, in which, for example, waste bag 586 has been replaced by media, e.g., base media, bag 800. Further, one or more pumps, e.g., IC Circulation Pump 512, EC Inlet Pump 578, and IC Inlet Pump 554, have been turned "OFF," according to an embodiment. There is thus no active inlet fluid flow into the bioreactor 501. To compensate for fluid lost due to evaporation at the gas transfer module or oxygenator 532, the EC Circulation Pump 528 may be left "ON," and the EC Waste Valve 582 may be left "OPEN." In embodiments, such configuration allows fluid from the substitute or replacement media bag 800 to backflow into the system at a rate equal to the rate of evaporation from the gas transfer module or oxygenator 532. The fluid lost in the system due to evaporation may thus be replaced without diluting chemical signaling occurring in the bioreactor 501 during cell growth therein. In embodiments, the lag phase of cell growth in the bioreactor 501 may therefore be significantly reduced, and more efficient cell expansion may occur. Further, by turning "OFF" the one or more inlet pumps, system resources may be conserved because there is no active inlet fluid being unnecessarily introduced into the system. While FIG. 8 shows an embodiment in which the IC Circulation Pump 512, EC Inlet Pump 578, and IC Inlet Pump 554 have been turned "OFF," other embodiments provide for one or more of such pumps, such as the IC Circulation Pump 512, for example, to remain "ON" or activated (not shown in FIG. 8). For example, it may be desired in embodiments to continue circulation in the intracapillary side depending on the type of cells, e.g., non-adherent cells, being expanded, according to an embodiment.

In some embodiments, when the waste bag 586 is replaced by the media bag 800, the substitute or replacement media bag may be positioned physically higher than the original position of the waste bag 586 to allow gravity to assist in draining media into the EC loop 504.

The replacement of the waste bag with a media bag allows passive replacement of fluid lost due to evaporation. Such passive replacement of fluid may provide a significant conservation of fluid in cell expansion processes. In processes involving active media replacement, media may be added and circulated in the IC loop during attachment of cells to replace fluid lost due to evaporation. As described above, if media is added at 0.1 ml/min, which may occur in some processes, according to embodiments, this may result in an excess amount (over the amount that has evaporated) of fluid of up to 130 mL/day in the system, for example. Passive addition of fluid with the replacement of the waste bag with a media bag avoids the addition of an excess amount. As can be appreciated, the media may include expensive additives. Saving about 130 mL/day, for example, may provide significant cost savings over other cell expansion processes.

Figure 9:
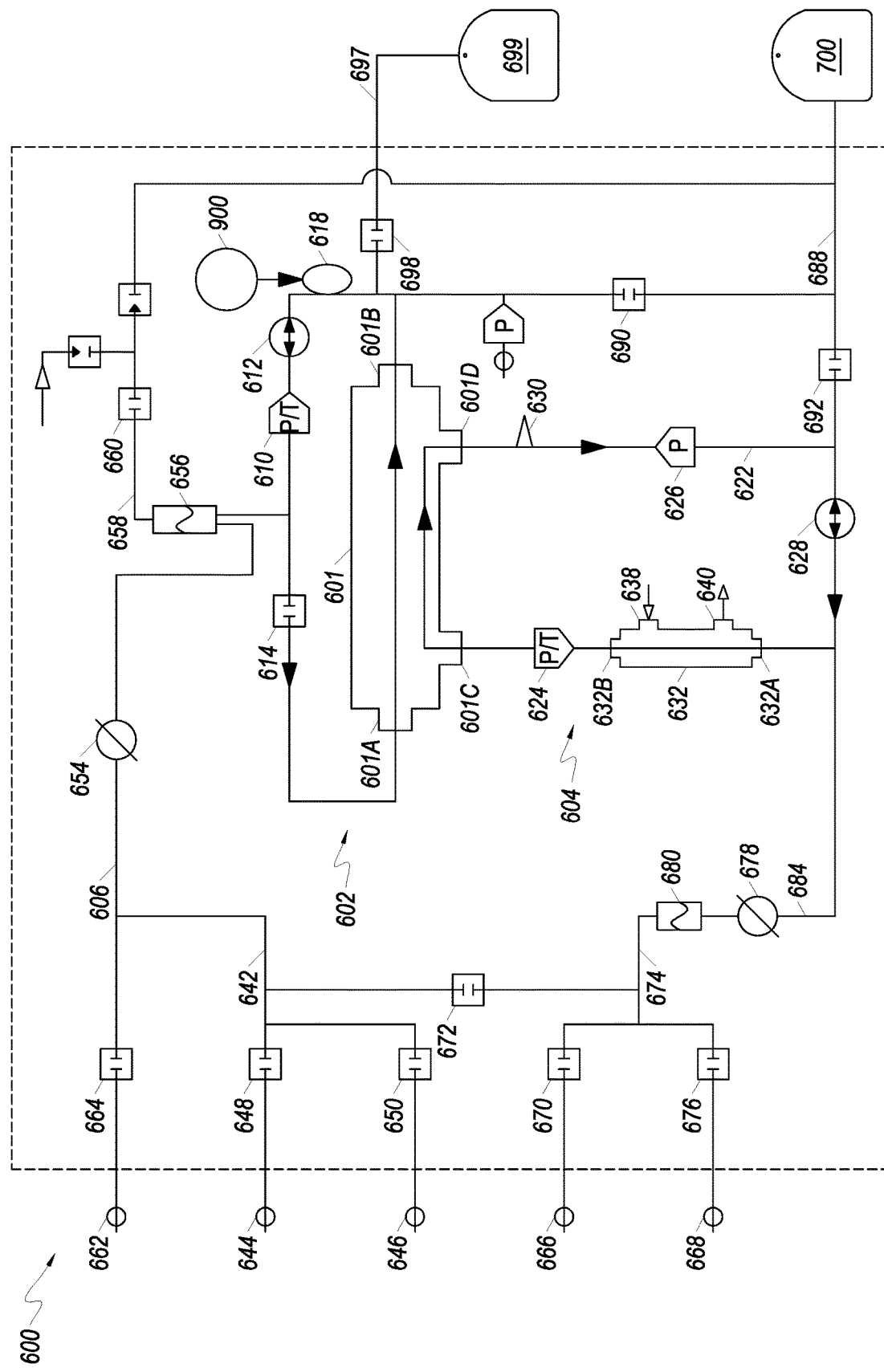
FIG. 9 depicts the cell expansion system embodiment of FIG. 6 with a molecule source included as part of the premounted fluid conveyance device, in accordance with embodiments of the present disclosure.

While FIGS. 7 and 8 allow for the passive replacement of media in a closed cell expansion system through the use of a media bag in replacement of a waste bag, FIG. 9 illustrates an embodiment in which a molecule source, e.g., a cell signaling protein molecule source, may be added to a cell expansion system, such as CES 600 (FIG. 6) (or CES 500 (FIG. 5)), for example. In one embodiment, the molecule source 900 may be a cytokine source welded into the sample coil or sampling coil 618, in which such cytokine source comprises a piece of tubing or other material welded into the sampling coil 618. Through such a source, i.e., direct source, cytokines may be added to the IC loop 602 without diluting such proteins, in which such dilution may occur where the cytokines are added instead at an IC Media bag, for example. In embodiments, the molecules are directly added to the IC loop 602. Such direct addition may also occur at a sample port, for example, according to an embodiment. Cytokines in the cell growth chamber 601 may thus be passively or actively replenished by such cytokine source. In such embodiment, the IC Circulation Pump 612 is turned to the "ON" position to allow the cytokines entering the IC loop 602 at the sampling coil 618 to be pumped to the expanding cell population in the bioreactor 601. Such cell source may ultimately save significant resources where chemical-signaling proteins used in the bioreactor are particularly costly, e.g., cytokines.

Figure 10:
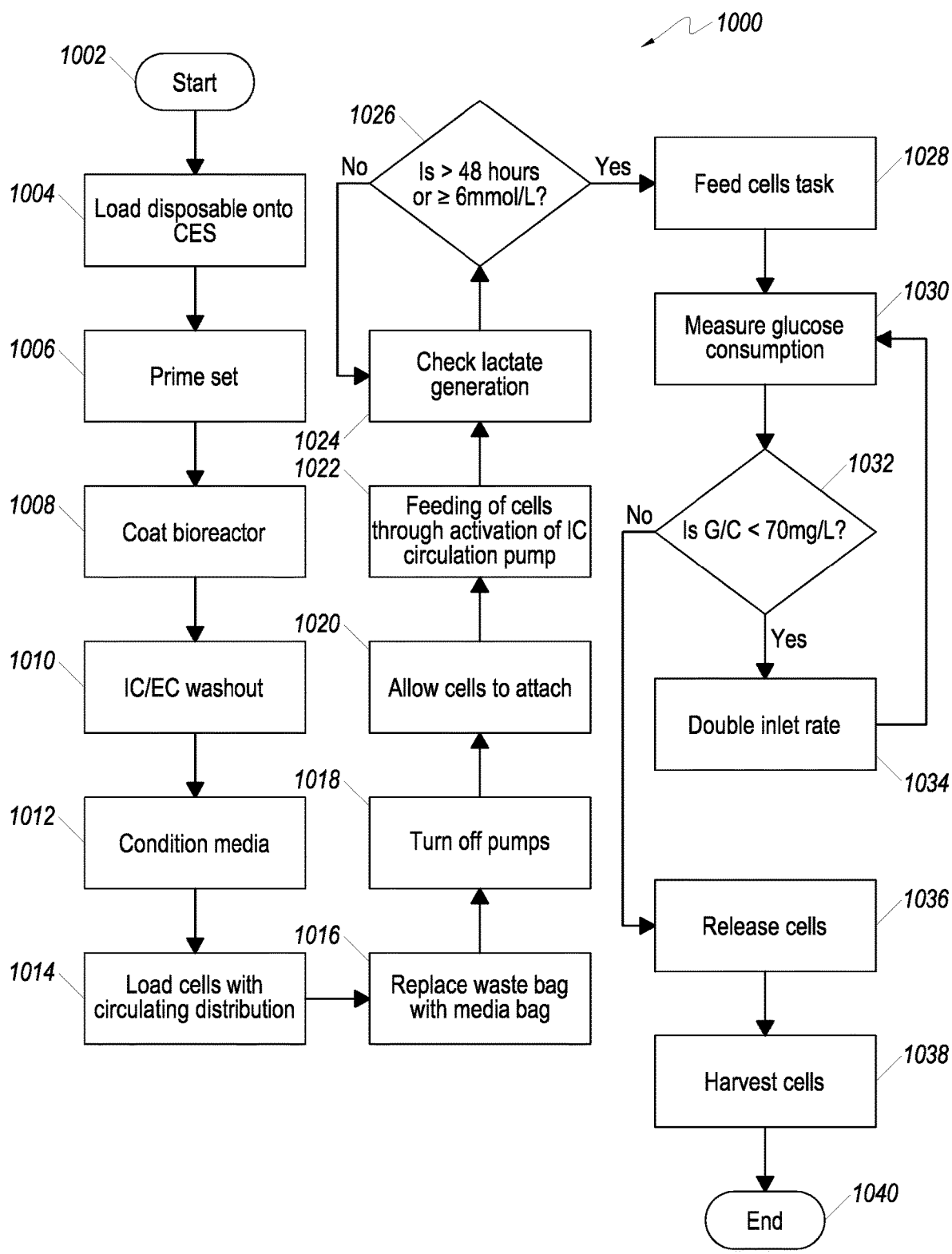
FIG. 10 illustrates a flow diagram depicting the operational characteristics of a process for passively replacing media in a cell expansion system, in accordance with embodiments of the present disclosure.

While various example embodiments of a cell expansion system and methods for passively replacing media in conjunction therewith have been described, FIG. 10 illustrates example operational steps 1000 for passively replacing fluid to control chemical signaling in a closed cell expansion system, in accordance with embodiments of the present disclosure. START operation 1002 is initiated, and process 1000 proceeds to load the disposable tubing set 1004 onto the cell expansion system. Next, the system is primed 1006, such as by having a user or operator instruct the system to prime by selecting a task for priming, for example. In another embodiment, the system is primed 1006 automatically without any selection of a task or instruction from a user or operator. After priming the set, process 1000 proceeds to coat the bioreactor 1008, in which the bioreactor is coated with a reagent. For example, a reagent is loaded into the IC loop until the Reagent Bag is empty. The reagent is chased from the air removal chamber into the IC loop, and the reagent is then circulated in the IC loop. Once the bioreactor is coated, the IC/EC Washout task is executed 1010, in which fluid on the IC circulation loop and on the EC circulation loop is replaced. The replacement volume is determined by the number of IC Volumes and EC Volumes exchanged, according to an embodiment. Next, to maintain the proper or desired gas concentration across fibers in the bioreactor membrane, the condition media task 1012 is executed to allow the media to reach equilibrium with the provided gas supply before cells are loaded into the bioreactor. For example, rapid contact between the media and the gas supply provided by the gas transfer module or oxygenator is provided by using a high EC circulation rate. In an embodiment, the system is then maintained in a proper state until a user or operator is ready to load cells into the bioreactor. In other embodiments, a user or operator may not be needed to perform the noted steps/operations; rather, the steps/operations may be performed automatically by the cell expansion system.

Process 1000 next proceeds to loading cells into the bioreactor from a cell inlet bag with circulating distribution 1014. In an embodiment, cells are loaded into the bioreactor from the cell inlet bag until the bag is empty. Cells are then chased from the air removal chamber to the bioreactor. Larger chase volumes spread the cells and move the cells toward the IC outlet. The distribution of cells is promoted across the membrane via IC circulation, such as through the IC circulation pump, with no IC inlet, for example.

After completion of the load cells with circulating distribution task 1014, the waste or outlet bag is replaced with a media bag 1016. In an embodiment, the media bag comprises about 500 mL of base media. The media bag may comprise other fluids and/or constituents, according to embodiments. In embodiments, the replacement of the outlet or waste bag with a media bag 1016 may be optional, in which fluid may be passively replaced by interrupting protocol procedures being executed and allowing any fluid in the outlet or waste bag (assuming no constituents toxic to cell growth are present in the outlet or waste bag) to be passively added to the system at the rate of evaporation during conditions of no active inlet fluid flow. Such passive addition of fluid avoids adding an excess amount of fluid and, thus, avoids diluting chemical signaling molecules.

Returning to FIG. 10, one or more pumps, e.g., the IC Inlet Pump, the IC Circulation Pump, and the EC Inlet Pump, may then be turned "OFF" or may otherwise be indicated to stop or deactivate 1018. Any adherent cells in the bioreactor are then allowed to attach to the bioreactor membrane 1020 for a period of time, such as for about eighteen (18) to about twenty-four (24) hours, according to an embodiment of the present disclosure. During this timeframe, flow continues on the EC circulation loop, in which the EC circulation rate is maintained at about 30 mL/min, according to an embodiment. A non-zero EC circulation rate helps to maintain the proper or desired gas concentration across the fibers of the bioreactor membrane by continuing to pump fluid in the EC loop through the gas transfer module or oxygenator. While the proper or desired gas concentration is maintained through the use of the gas transfer module, evaporation of fluid also occurs at the gas transfer module. By keeping the EC Waste Valve open, however, media from the media bag (replacing the waste bag) may back-flow into the system and be pumped by the EC Circulation Pump through the EC loop. The media may thus replace fluid lost due to evaporation from the gas transfer module at the rate of evaporation. Thus, membrane fibers in the bioreactor will not be diluted with excess fluid, and the transition of cell growth out of the lag phase will not be inhibited.

After the attaching of any adherent cells for about eighteen (18) to about twenty-four (24) hours, according to an embodiment, a continued cell attachment phase 1022 continues for up to about forty-eight (48) hours. During operation 1022, the IC circulation pump may be activated or turned "ON" to provide even the furthest fibers of the bioreactor membrane with media. For example, the IC circulation pump may be activated to adjust the IC circulation rate to about 20 mL/min, according to an embodiment of the present disclosure. However, during this period of modified feeding through activation of the IC circulation pump 1022, the IC inlet rate remains at 0 mL/min. Rather, the substitute media bag (in replacement of the waste bag) continues to provide any necessary fluid replacement to the system while not diluting the membranes or inhibiting chemical signaling. Operation 1022 with modified feeding of the cells thus allows for cell attachment to continue without disruption of chemical signaling occurring in the bioreactor. This continued cell attachment phase continues, according to embodiments, for up to about forty-eight (48) additional hours and/or, in embodiments, until the lactate generation of the cells is greater than or equal to about 6 mmol/L. In an embodiment, the concentration of lactate is measured. In another embodiment, the lactate generation rate, for example, is measured. In an embodiment, the lactate generation is thus checked at operation 1024 to determine if the concentration of lactate is equal to or exceeds 6 mmol/L. In other embodiments, the lactate generation is checked at operation 1024 to determine the concentration of lactate in relation to another predetermined amount.

Process 1000 next proceeds to query 1026, in which it is determined whether more than forty-eight hours has passed since the IC circulation pump was activated or whether the concentration of lactate is equal to or greater than about 6 mmol/L. If less than forty-eight (48) hours has passed or if the concentration of lactate is not equal to or in excess of about 6 mmol/L, process 1000 proceeds NO to check lactate generation operation 1024 and then to query 1026 again. It is noted that the present disclosure is not limited to determining whether forty-eight (48) hours have passed or whether there is a lactate concentration equal to or in excess of 6 mmol/L. In other embodiments, process 1000 may involve a different predetermined period of time. For example, at query 1026, a determination may be made whether about 12 hours, about 24 hours, about 36 hours, or about 40 hours have passed. In other embodiments, the predetermined period of time may be about 50 hours or about 60 hours. In embodiments, a determination may be made whether more than about 12 hours, more than about 24 hours, more than about 36 hours, or more than about 40 hours have passed. In other embodiments, a determination may be made whether less than about 60 hours or less than about 50 hours have passed. In yet other embodiments, process 1000 may involve determining whether the concentration of lactate is equal to or greater than another predetermined amount, such as about 3 mmol/L, about 4 mmol/L, about 5 mmol/L, about 7 mmol/L, or about 8 mmol/L. In embodiments, a determination may be made whether the concentration of lactate is more than about 3 mmol/L, more than about 4 mmol/L, or more than about 5 mmol/L. In other embodiments, a determination may be made whether the concentration of lactate is less than about 8 mmol/L or less than about 7 mmol/L.

If at query 1026 it is determined that more than about forty-eight (48) hours has passed since the IC circulation pump was activated or that the concentration of lactate is equal to or greater than 6 mmol/L, process 1000 proceeds YES to feed cells operation 1028, in which the IC inlet pump is activated or turned "ON" to maintain an IC Inlet Rate of 0.1 mL/min. Next, process 1000 proceeds to measure the glucose consumption 1030. In an embodiment, the concentration of glucose is measured. In another embodiment, the glucose consumption rate, for example, is measured. At query 1032, it is determined whether the measured glucose consumption is less than about 70 mg/L, in an embodiment. If the glucose consumption is less than about 70 mg/L (or another predetermined amount, according to other embodiments), process 1000 proceeds YES to double the IC Inlet Rate 1034. Process 1000 then proceeds to operation 1030 to continue measuring the glucose consumption of the cells and back to query 1032.

The present disclosure is not limited to determining whether the glucose consumption is less than about 70 mg/L. In other embodiments, process 1000 may involve a different predetermined amount. For example, in embodiments, process 1000 may involve determining whether the glucose consumption is less than another predetermined amount, such as about 65 mg/L, about 60 mg/L, or about 55 mg/L, for example. In other embodiments, the process 1000 may involve determining whether the glucose consumption is less than another predetermined amount, such as about 85 mg/L, about 80 mg/L, or about 75 mg/L, for example. In embodiments, a determination may be made whether the glucose consumption is more than about 55 mg/L, more than about 60 mg/L, or more than about 65 mg/L. In other embodiments, a determination may be made whether the glucose consumption is less than about 85 mg/L, less than about 80 mg/L, or less than about 75 mg/L.

If, at query 1032, the glucose consumption is determined to be greater than 70 mg/L, process 1000 proceeds NO to release the cells operation 1036, in which the cells are released from the membrane of the bioreactor and are suspended in the IC loop. In embodiments, an IC/EC Washout task in preparation for adding a reagent is performed. For example, IC/EC media may be replaced with a phosphate buffered saline (PBS) to remove protein, calcium ($Ca^{2+}$), and magnesium ($Mg^{2+}$) in preparation for adding trypsin, or another chemical-releasing agent, to release any adherent cells. A reagent may be loaded into the system until the reagent bag is empty. The reagent may be chased into the IC loop, and the reagent may be mixed within the IC loop. Following the release of any adherent cells, harvest operation 1038 transfers the cells in suspension from the IC circulation loop, including any cells remaining in the bioreactor, to the harvest bag. Process 1000 then terminates at END operation 1040.

Figure 11:
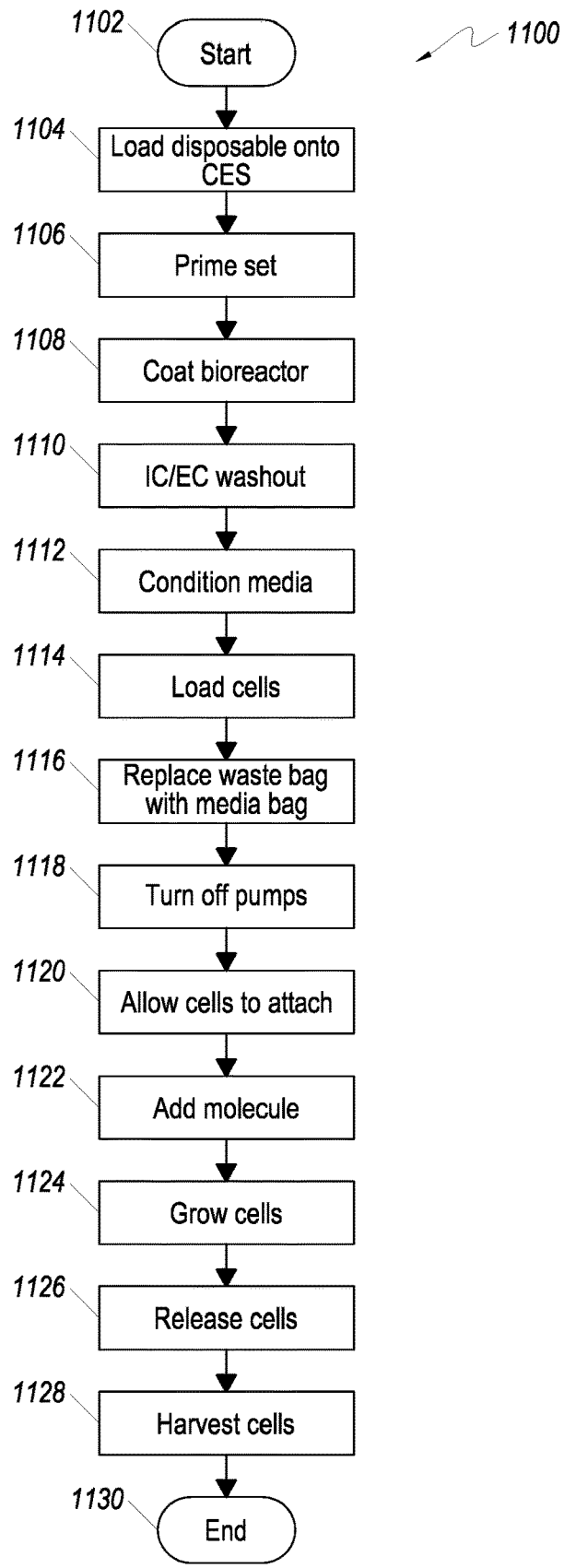
FIG. 11 depicts a flow diagram illustrating the operational characteristics of a process for adding a molecule from a molecule source implemented as part of the cell expansion system itself, in accordance with embodiments of the present disclosure.

Next, FIG. 11 depicts a flow diagram illustrating the operational characteristics of a process 1100 for adding a molecule from a molecule source, implemented as part of a cell expansion system itself, in accordance with embodiments of the present disclosure. While various example embodiments of a cell expansion system and methods for adding a molecule to a cell expansion system have been described, FIG. 11 illustrates example operational steps 1100 for adding a molecule that affects chemical signaling in a closed cell expansion system, in accordance with embodiments of the present disclosure. Some embodiments provide for the passive addition of a molecule from a molecule source. START operation 1102 is initiated, and process 1100 proceeds to load a disposable tubing set 1104 onto the cell expansion system. Next, the system is primed 1106, such as by having an operator or user provide an instruction to the system to prime by selecting a task for priming, for example. In another embodiment, the system is primed 1106 automatically without any selection of a task or instruction from an operator or user.

After priming the set, process 1100 proceeds to coat the bioreactor 1108, in which the bioreactor may be coated with a reagent. For example, in embodiments, a reagent is loaded into the IC loop until a reagent container is empty. The reagent may be chased from the air removal chamber into the IC loop, and the reagent may then be circulated in the IC loop. Once the bioreactor is coated, the IC/EC Washout task may be executed 1110, in which fluid on the IC circulation loop and on the EC circulation loop may be replaced, according to an embodiment. In an embodiment, the replacement volume is determined by the number of IC Volumes and EC Volumes exchanged.

Next, to maintain the proper or desired gas concentration across fibers in the bioreactor membrane, the condition media task 1112 is executed to allow the media to reach equilibrium with the provided gas supply before cells are loaded into the bioreactor. For example, rapid contact between the media and the gas supply provided by the gas transfer module or oxygenator is provided by using a high EC circulation rate. In an embodiment, the system may then be maintained in a proper or desired state until an operator or user is ready to load cells into the bioreactor. In embodiments, such loading of cells is performed automatically.

Process 1100 next proceeds to loading cells into the bioreactor from a cell inlet bag with circulating distribution 1114. In an embodiment, cells are loaded into the bioreactor from a cell inlet bag until the bag is empty. Cells are then chased from the air removal chamber to the bioreactor. In embodiments that utilize larger chase volumes, cells are spread and move toward the IC outlet. The distribution of cells may be promoted across the membrane via IC circulation, such as through the IC circulation pump, with no IC inlet flow, for example.

After completion of the load cells with circulating distribution task 1114, the waste bag is replaced with a media bag 1116. In an embodiment, the media bag comprises about 500 mL of base media. In another embodiment, the media bag comprises any type of replacement fluid. In a further embodiment, step 1116 is optional, in which the outlet or waste bag stays connected and is not replaced with another bag. In yet a further embodiment, step 1116 is optional, in which the outlet or waste bag stays connected and desired constituents or other fluid(s) are added to the outlet or waste bag for passively adding such constituents/other fluid to the system.

In embodiments, one or more pumps, e.g., the IC Inlet Pump, the IC Circulation Pump, and the EC Inlet Pump, may then be turned "OFF" or may otherwise be indicated to stop or deactivate 1118. Any adherent cells in the bioreactor are then allowed to attach to the bioreactor membrane 1120 for a period of time, such as for about eighteen (18) to about twenty-four (24) hours, according to an embodiment of the present disclosure. During this timeframe, flow may continue on the EC circulation loop, in which the EC circulation rate may be maintained at about 30 mL/min, according to an embodiment. A non-zero EC circulation rate helps to maintain the proper or desired gas concentration across the fibers of the bioreactor membrane by continuing to pump fluid in the EC loop through the gas transfer module or oxygenator. While the proper or desired gas concentration is maintained through the use of the gas transfer module, evaporation of fluid also occurs at the gas transfer module. By keeping the EC Waste Valve open, however, media from the substitute media bag (replacing the waste bag) may back-flow into the system and be pumped by the EC Circulation Pump through the EC loop. The media may thus replace fluid lost due to evaporation from the gas transfer module at the rate of evaporation. Thus, membrane fibers in the bioreactor will not be diluted with excess fluid, and the transition of cell growth out of the lag phase will not be inhibited.

After the attaching of any adherent cells, an add molecule phase 1122 is performed. The molecule may be a protein molecule that is added to promote expansion of the cells. For example, the molecule may be a signaling molecule, such as one or more cytokines or growth factors that are involved in intercellular communications. The molecule may signal the cells to expand. In other embodiments, the molecule may not be directly involved in signaling but may help create an environment that is conducive to cell growth, in which examples of such molecules include carrier proteins, buffers, pH modifiers, etc. In embodiments, the molecule is added to the space where the cells are being grown, e.g., the IC or EC space. In embodiments, the molecules are added directly to the IC loop from a direct source of such molecules. Such direct addition may occur at a sampling coil or at a sample port, for example, according to embodiments. Cytokines, or other type of cell-signaling protein molecules, may be added to the bioreactor by, for example, welding a tubing line or other material connected to a cytokine source to a sampling coil or sample coil of the cell expansion system. The cytokines may thus be added to the bioreactor at the sample coil. Such direct addition results in a significant savings of cytokines, which may be costly, because a much higher amount of cytokines would need to be added to a media bag to compensate for dilution of the cytokines by the media than are needed when only the cytokine source itself replenishes the bioreactor, according to an embodiment. Further, cytokines tend to degrade quickly, in which such degradation may be minimized by adding cytokines closer to the expanding cell population, e.g., at the sample coil of the bioreactor itself. In such embodiments, the cytokines in the bioreactor may thus be maintained at a certain level while conserving resources. Through such a source, i.e., direct source, cytokines may be added to the IC loop without diluting such proteins, in which such dilution may occur where the cytokines are added instead at the IC Media bag, for example.

As noted above, the add molecule phase 1122 may be performed after the waste bag is replaced with a media bag 1116, according to an embodiment. In some embodiments, the molecule that is added at operation 1122 may be relatively expensive, and it is desirable to use the minimum amount required to promote growth of the cells. Performing operation 1116 first allows media from the media bag (replacing the waste bag) to back-flow into the system and be pumped by the EC Circulation Pump through the EC loop. According to an embodiment, only the media that is lost due to evaporation from the gas transfer module is replaced and at the rate of evaporation. Thus, the molecule may not be diluted with excess fluid. Accordingly, in an embodiment, only an amount of the molecule that may be effective at promoting growth may be added at operation 1122 since dilution by excess fluid may not be occurring.

After operation 1122, cells are grown at operation 1124. It is noted that, in embodiments, operation 1124 may involve a number of sub-operations. In some embodiments, the sub-operations include operations performed in process 1000 (FIG. 10). For example, in one embodiment, a circulating media operation may be performed to feed the cells. The IC circulation pump may be activated or turned "ON" to provide even the furthest fibers of the bioreactor membrane with media. The IC circulation pump may be activated to adjust the IC circulation rate to about 20 mL/min, according to an embodiment of the present disclosure. In some embodiments, even though the IC circulation pump is turned on, the IC inlet rate remains at 0 mL/min. Rather, the media bag (substitute media bag in replacement of the waste bag) continues to provide any necessary fluid replacement to the system while not diluting the molecule or otherwise inhibiting chemical signaling. In embodiments, operation 1124 allows cell attachment and cell growth to occur without disruption of chemical signaling by dilution of the molecules. This continued cell attachment and growth may continue, according to embodiments, for some predetermined period of time or may be based on a lactate generation of the cells, e.g., 6 mmol/L (in an embodiment). In these embodiments, additional sub-operations, such as determining lactate concentration(s) or that a predetermined period of time has elapsed, may be performed.

Operation 1124 may further involve a sub-operation of activating the IC inlet pump to maintain a predetermined IC inlet rate, e.g., 0.1 mL/min. This sub-operation may be triggered based on a predetermined period of time having elapsed or on a measurement, such as lactate concentration, for example.

In some embodiments, operation 1124 may involve a number of sub-operations to determine when to stop growing cells and begin releasing and harvesting cells. In one embodiment, this may include measuring a parameter, such as glucose consumption. In some embodiments, a predetermined glucose concentration, e.g., greater than 70 mg/L, may trigger subsequent operations, e.g., 1126 and 1128. In other embodiments, other parameters or the passage of a predetermined period of time may trigger subsequent operations.

At operation 1126, any adherent cells are released from the membrane of the bioreactor and are suspended, e.g., in the IC loop. In embodiments, an IC/EC washout task in preparation for adding a reagent to release the cells may be performed as part of operation 1126. For example, IC/EC media may be replaced with PBS to remove protein, calcium ($Ca^{2+}$), and magnesium ($Mg^{2+}$) in preparation for adding trypsin, or other chemical-releasing agent, to release any adherent cells. A reagent may be loaded into the system until the reagent bag is empty. The reagent may be chased into the IC loop, and the reagent may be mixed within the IC loop. Following the release of any adherent cells, harvest operation 1128 transfers the cells in suspension from the IC circulation loop, including any cells remaining in the bioreactor, to a harvest bag(s). Process 1100 then terminates at END operation 1130.

Figure 12:
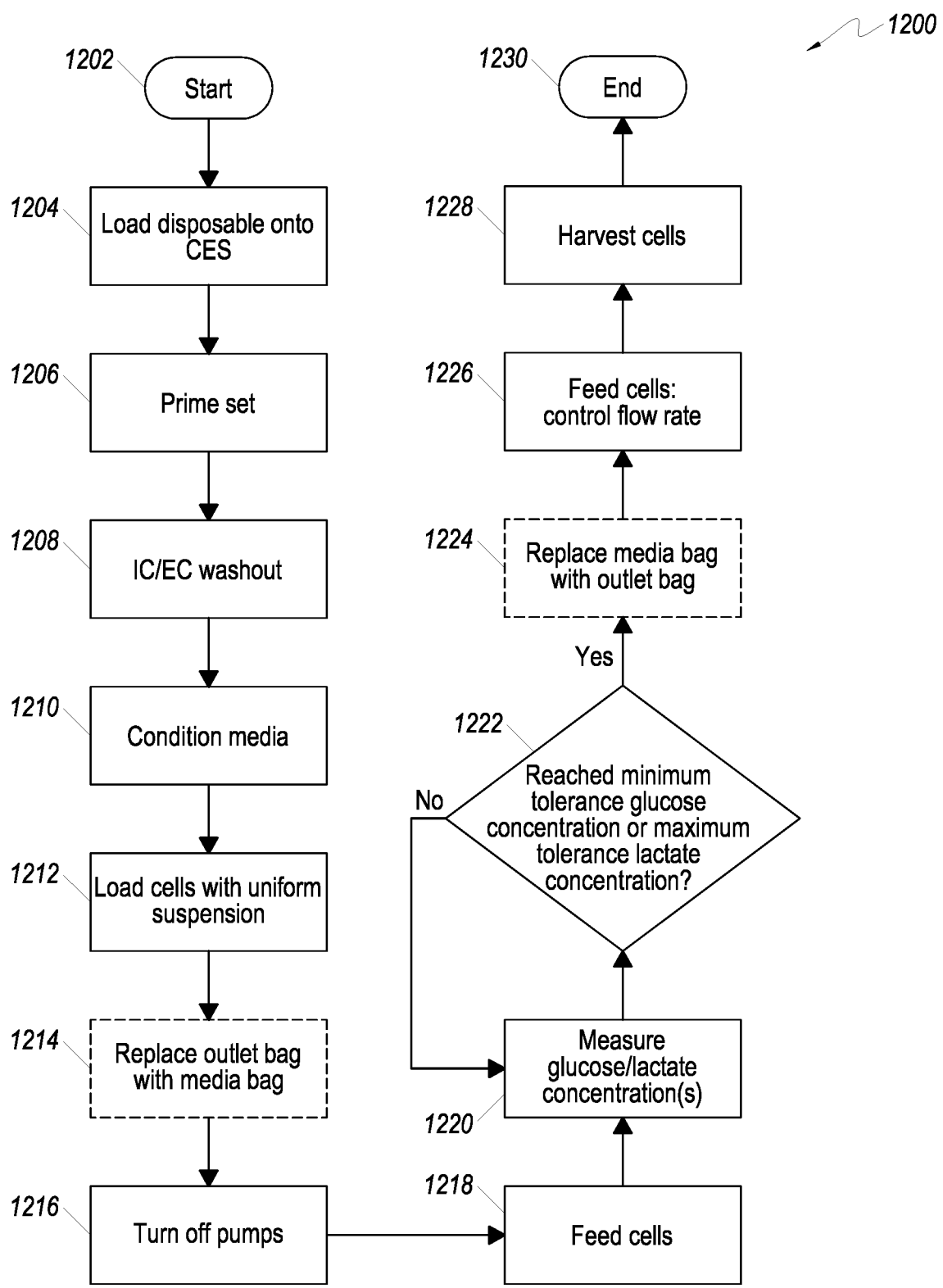
FIG. 12 illustrates a flow diagram depicting the operational characteristics of another embodiment of a process for passively replacing media in a cell expansion system.

Turning to FIG. 12, example operational steps 1200 for passively replacing fluid to control chemical signaling in a closed cell expansion system are shown, in accordance with embodiments of the present disclosure. START operation 1202 is initiated, and process 1200 proceeds to load the disposable tubing set 1204 onto a cell expansion system. Next, the system is primed 1206, such as by having a user or operator instruct the system to prime by selecting a task for priming, for example. In another embodiment, the system is primed 1206 automatically without any selection of a task or instruction from a user or operator. After priming the set, process 1200 proceeds to IC/EC washout 1208, in which fluid on the IC and EC circulation loops may be replaced in preparation for cell culturing. The replacement volume may be specified by the number of IC Volumes and EC Volumes exchanged, according to embodiments. Next, to allow media to reach equilibrium with the gas supply prior to the loading of cells, process 1200 proceeds to condition media task 1210. For example, rapid contact between the media and the gas supply may be provided by using a high EC circulation rate. In an embodiment, the system may then be maintained in a proper state until the user or operator is ready to load cells into the bioreactor. In embodiments, a user or operator may not be needed to perform the noted steps/operations; rather, the steps/operations may be performed automatically by the cell expansion system.

Process 1200 next proceeds to loading cells with uniform suspension 1212. In an embodiment, cells may be loaded from a cell inlet bag. IC circulation may be used to distribute the cells. In an embodiment, cells are loaded into the bioreactor from a cell inlet bag. Cells are then chased from the air removal chamber to the IC loop. The distribution of cells is promoted across the membrane via IC circulation with no IC inlet, for example, and thus no ultrafiltration, according to embodiments.

Next, process 1200 proceeds to the optional (shown in a dashed-line format) step of replacing an outlet or waste bag with a media bag (e.g., a substitute media bag) 1214. In an embodiment, the substitute media bag comprises about 0.2 L of media without protein. Other volumes and types of replacement fluid in the substitute media bag may be used in accordance with embodiments of the present disclosure. Process 1200 next proceeds to turning "OFF" or otherwise deactivating one or more pumps 1216. In an embodiment, the IC inlet pump and the EC inlet pump are turned "OFF" or otherwise indicated to stop or deactivate 1216. Such pump deactivation allows chemical signals, such as CCK, to increase in concentration by turning the inlet media flow rate "OFF" to the IC circulation loop and the EC circulation loop. In such embodiments, fluid from the substitute bag may be passively added to the system at the rate of evaporation during conditions of no active inlet fluid flow. In embodiments where the outlet or waste bag is not replaced, fluid may be passively replaced in the system by interrupting protocol procedures being executed and allowing any fluid in the outlet or waste bag (assuming no constituents toxic to cell growth are present in the outlet or waste bag) to be passively added to the system at the rate of evaporation during conditions of no active inlet fluid flow. Such passive addition of fluid avoids adding an excess amount of fluid and, thus, avoids diluting chemical signaling. In an embodiment, the EC circulation pump may remain "ON." In further embodiments, both the IC circulation pump and the EC circulation pump remain activated or "ON."

Next, process 1200 proceeds to feeding the cells 1218. In an embodiment, the cell culture may be sampled for cell counts as well by excising a length of tubing to provide a representative cell concentration sample of the IC loop. In other embodiments, cells may be counted by withdrawing a sample from the sampling coil or sample port, for example.

Process 1200 next proceeds to measuring the glucose and/or lactate concentration(s) 1220. At query 1222, it is determined whether the cell culture conditions have reached a minimum tolerance glucose concentration or a maximum tolerance lactate concentration. Such tolerance concentrations may occur earlier or later than day 4, according to embodiments. If the tolerance concentration(s) have not been reached, process 1200 proceeds NO to continue to measure the glucose/lactate concentration(s) 1220. If the tolerance concentration(s) have been reached, process 1200 proceeds YES to the optional (shown in a dashed-line format) step of replacing the substitute media bag (from optional step 1214) with the waste or outlet bag 1224. In an embodiment, the original waste or outlet bag removed at optional step 1214 is used to replace the substitute media bag at optional step 1224. In another embodiment, a different waste or media bag is used to replace the substitute media bag at optional step 1224.

Following optional step 1224, process 1200 proceeds to feed the cells by adding a controlled flow rate to the IC circulation loop and/or the EC circulation loop 1226 once the cell culture conditions have reached a minimum tolerance glucose concentration or a maximum tolerance lactate concentration, for example. In an embodiment, a low flow rate is continuously added to the IC circulation loop and/or the EC circulation loop. Such feeding with the continuous addition of a low flow rate, for example, may occur earlier or later than day 4, according to embodiments.

Harvest operation 1228 next transfers cells in suspension from the IC circulation loop, including cells in the bioreactor, to a harvest bag. Process 1200 then terminates at END operation 1230.

With respect to the processes illustrated in FIGS. 10, 11, and 12, the operational steps depicted are offered for purposes of illustration and may be rearranged, combined into other steps, used in parallel with other steps, etc., according to embodiments of the present disclosure. Thus, although the processes have been described with steps listed in a particular order, the present disclosure is not limited to such order. In other embodiments, steps may be performed in a different order, in parallel, or any different number of times, e.g., before and after another step. Further, fewer or additional steps may be used in embodiments without departing from the spirit and scope of the present disclosure. For example, where only suspension or non-adherent cells are present, some steps may not be used as they may be used with adherent cells, such as coating the bioreactor 1008 and 1108, allowing cells to attach 1020 and 1120, and releasing cells 1036 and 1126, for example. Even without such steps, FIGS. 10 and 11, for example, may still apply to the expansion of suspension or non-adherent cells, for example, according to embodiments. As a further example, although not shown in FIGS. 10 and 11, an additional step(s) may include replacing the substitute media bag (previously used to replace the outlet or waste bag) with an outlet or waste bag. Such outlet or waste bag may be the original outlet or waste bag used with the system, according to an embodiment. In another embodiment, a different outlet or waste bag may be used to replace the substitute media bag. Also, the parameters, such as lapse of a predetermined period of time, lactate concentration, glucose consumption, and circulation rates, for example, may also be different than those described above, which are provided merely for illustrative purposes. In addition, as indicated above, process 1200 includes some optional steps/sub-steps shown with dashed-line format. However any steps listed above (in any of processes 1000, 1100, and/or 1200) that are not indicated as optional should not be considered as essential to the one or more present inventions, but may be performed in some embodiments of the one or more present inventions and not in others. Further, while some steps, operations and/or sub-operations are described with reference to an operator or user, such steps, operations and/or sub-operations may be performed automatically, according to embodiments.

Figure 13:
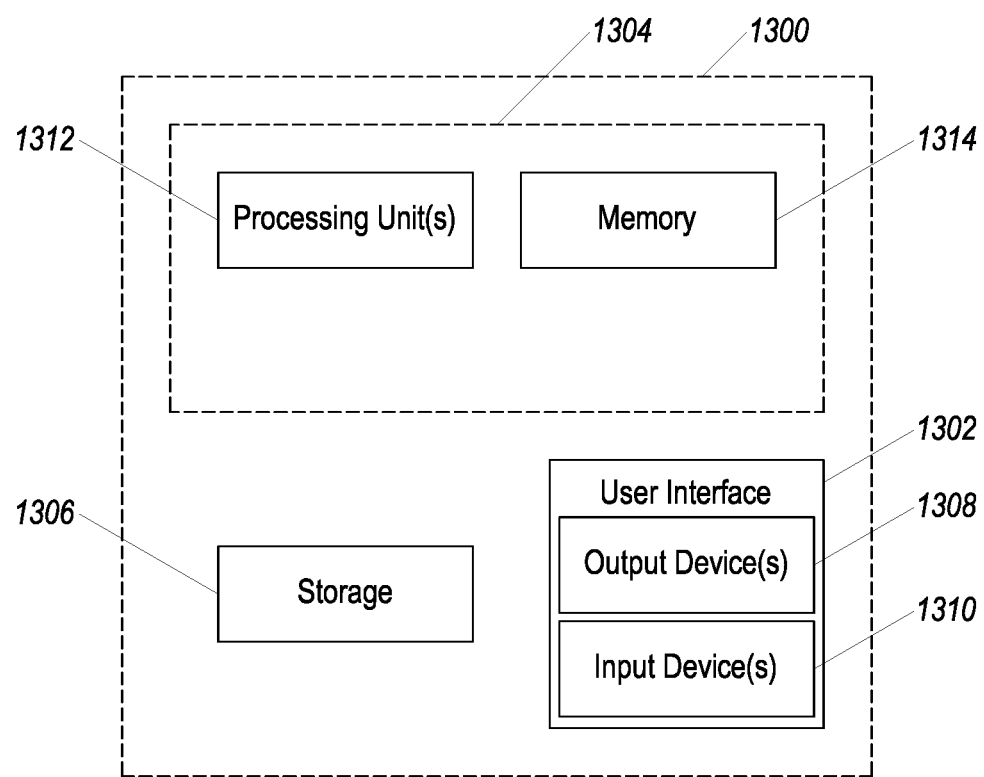
FIG. 13 depicts an example processing system of a cell expansion system upon which embodiments of the present disclosure may be implemented.

Finally, FIG. 13 illustrates example components of a computing system 1300 upon which embodiments of the present disclosure may be implemented. Computing system 1300 may be used in embodiments, for example, where a cell expansion system uses a processor to execute tasks, such as custom tasks or pre-programmed tasks performed as part of processes, such as processes 1000, 1100, and 1200 described above. For example, a pre-programmed task may include, "Feed Cells."

The computing system 1300 may include a user interface 1302, a processing system 1304, and/or storage 1306. The user interface 1302 may include output device(s) 1308, and/or input device(s) 1310 as understood by a person of skill in the art. Output device(s) 1308 may include one or more touch screens, in which the touch screen may comprise a display area for providing one or more application windows. The touch screen may also be an input device 1310 that may receive and/or capture physical touch events from a user or operator, for example. The touch screen may comprise a liquid crystal display (LCD) having a capacitance structure that allows the processing system 1304 to deduce the location(s) of touch event(s), as understood by those of skill in the art. The processing system 1304 may then map the location of touch events to user interface (UI) elements rendered in predetermined locations of an application window. The touch screen may also receive touch events through one or more other electronic structures, according to embodiments. Other output devices 1308 may include a printer, speaker, etc. Other input devices 1310 may include a keyboard, other touch input devices, mouse, voice input device, etc., as understood by a person of skill in the art.

Processing system 1304 may include a processing unit 1312 and/or a memory 1314, according to embodiments of the present disclosure. The processing unit 1312 may be a general purpose processor operable to execute instructions stored in memory 1314. Processing unit 1312 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits, etc., as understood by a person of skill in the art.

The memory 1314 may include any short-term or long-term storage for data and/or processor executable instructions, according to embodiments. The memory 1314 may include, for example, Random Access Memory (RAM), Read-Only Memory (ROM), or Electrically Erasable Programmable Read-Only Memory (EEPROM), as understood by a person of skill in the art. Other storage media may include, for example, CD-ROM, tape, digital versatile disks (DVD) or other optical storage, tape, magnetic disk storage, magnetic tape, other magnetic storage devices, etc., as understood by a person of skill in the art.

Storage 1306 may be any long-term data storage device or component. Storage 1306 may include one or more of the systems described in conjunction with the memory 1314, according to embodiments. The storage 1306 may be permanent or removable. In embodiments, storage 1306 stores data generated or provided by the processing system 1304.

EXAMPLES

Below are examples of protocols that may be used with a cell expansion system, such as CES 500 (FIG. 5), CES 600

(FIG. 6), CES 700 (FIG. 7), CES 800 (FIG. 8), or CES 900 (FIG. 9), for example, that implements features of this disclosure. It is noted that the example protocols below are provided for illustrative purposes and are not intended to limit other embodiments, which may include different steps, parameters, or other features. The example protocols, including the steps (and any sub-steps) of loading cells and distributing cells, for example, may be performed automatically in some embodiments, such as by a processor executing pre-programmed tasks stored in memory. In other embodiments, the steps (and any sub-steps) are performed through the combination of automated and manual execution of operations. In further embodiments, the steps (and any sub-steps) are performed by an operator(s) or user(s) or through other manual means.

Example 1: Protocol 1

Day: −1 Coat Bioreactor

This part of the example protocol coats a bioreactor with a reagent. The bioreactor may include a hollow fiber membrane.
Step 1: loads a reagent into the IC loop until the bag is empty.
Step 2: chases the reagent from the ARC into the IC loop.
Step 3: circulates the reagent in the IC loop.
Before starting this task, the following preconditions may be satisfied:
Include a minimum of 40 mL of air in the cell inlet bag.
Table 1 describes the bags of solution that are attached to each line when performing the Coat Bioreactor portion of the protocol. These solutions and corresponding volumes are provided as one example of default settings that may be used.

TABLE 1

Solutions for Coat Bioreactor

| Bag | Solution in Bag | Volume (estimation) |
|---|---|---|
| Cell Inlet | None | N/A |
| Reagent | Fibronectin | about 5 mg Fibronectin in about 100 mL PBS |
| IC Media | None | N/A |
| Wash | PBS | about 0.1 L + 6 mL/hr (overnight) |
| EC Media | None | N/A |

The values for each setting for step 1 may be used as shown in Table 2.

TABLE 2

Step 1 for Coat Bioreactor

| Setting | Example Factory Default | Example Laboratory Default | Modifications |
|---|---|---|---|
| IC Inlet | Reagent | | |
| IC Inlet Rate | about 10 mL/min | | |
| IC Circulation Rate | about 100 mL/min | | |
| EC Inlet | None | | |
| EC Inlet Rate | about 0 mL/min | | |
| EC Circulation Rate | about 30 mL/min | | |
| Outlet | EC Waste | | |
| Rocker Control | Stationary, approximately (0°) | | |
| Stop Condition | Empty Bag | | |

Values for each setting for step 2 shown in Table 3 may be used.

TABLE 3

Step 2 Settings for Coat Bioreactor

| Setting | Example Factory Default | Example Laboratory Default | Modifications |
|---|---|---|---|
| IC Inlet | Wash | | |
| IC Inlet Rate | about 10 mL/min | | |
| IC Circulation Rate | about 100 mL/min | | |
| EC Inlet | None | | |
| EC Inlet Rate | about 0 mL/min | | |
| EC Circulation Rate | about 30 mL/min | | |
| Outlet | EC Waste | | |
| Rocker Control | Stationary, approximately (0°) | | |
| Stop Condition | about IC Volume (22 mL) | | |

Values for each setting for step 3 shown in Table 4 may be used.

TABLE 4

Step 3 Settings for Coat Bioreactor

| Setting | Example Factory Default | Example Laboratory Default | Modifications |
|---|---|---|---|
| IC Inlet | None | | |
| IC Inlet Rate | about 0 mL/min | | |
| IC Circulation Rate | about 20 mL/min | | |
| EC Inlet | Wash | | |
| EC Inlet Rate | about 0.1 mL/min | | |
| EC Circulation Rate | about 30 mL/min | | |
| Outlet | EC Waste | | |
| Rocker Control | Stationary, approximately (0°) | | |
| Stop Condition | Manual | | |

Day: 0 IC EC Washout

This part of the example protocol is performed to replace the fluid on both the IC circulation loop and the EC circulation loop. The replacement volume may be specified by the number of IC Volumes and EC Volumes exchanged.

Table 5 describes the bags of solution that are attached to each line when performing IC EC Washout of this example protocol. These solutions and corresponding volumes are provided as one example of default settings that may be used.

TABLE 5

Solutions for IC EC Washout

| Bag | Solution in Bag | Volume (estimation) |
|---|---|---|
| Cell Inlet | None | N/A |
| Reagent | None | N/A |
| IC Media | Media with Protein | about 1.4 L |
| Wash | None | N/A |
| EC Media | None | N/A |

The values for IC EC Washout shown in Table 6 may be used.

TABLE 6

Task Settings for IC EC Washout

| Setting | Example Factory Default | Example Laboratory Default | Modifications |
|---|---|---|---|
| IC Inlet | IC Media | | |
| IC Inlet Rate | about 100 mL/min | | |
| IC Circulation Rate | about −17 mL/min | | |
| EC Inlet | EC Media | IC Media | |
| EC Inlet Rate | about 148 mL/min | | |
| EC Circulation Rate | about −1.7 mL/min | | |
| Outlet | IC and EC Waste | | |
| Rocker Control | In Motion approximately (−90°, 180°, 1 sec) | | |
| Stop Condition | Exchange (about 2.5 IC Volumes) (about 2.5 EC Volumes) | | |

Day: 0 Condition Media

This part of the example protocol is performed to allow the media to reach equilibrium with the provided gas supply before loading the cells. This task may include two separate steps:
Step 1: provides rapid contact between the media and the gas supply by using a high EC circulation rate.
Step 2: maintains the system in a proper state until the operator is ready to load the cells.

Table 7 describes the bags of solution that are attached to each line when performing Condition Media. These solutions and corresponding volumes are provided as one example of default settings that may be used.

TABLE 7

Solutions for Condition Media

| Line | Solution in Bag | Volume (estimation) |
|---|---|---|
| Cell Inlet | None | N/A |
| Reagent | None | N/A |
| IC Media | None | N/A |
| Wash | None | N/A |
| EC Media | Media without Protein | about 0.1 L plus 6 mL/hour |

The values for step 1 shown in Table 8 may be used.

TABLE 8

Step 1 Settings for Condition Media

| Setting | Example Factory Default | Example Laboratory Default | Modifications |
|---|---|---|---|
| IC Inlet | None | | |
| IC Inlet Rate | about 0 mL/min | | |
| IC Circulation Rate | about 100 mL/min | | |
| EC Inlet | EC Media | IC Media | |
| EC Inlet Rate | about 0.1 mL/min | | |
| EC Circulation Rate | about 250 mL/min | | |
| Outlet | EC Waste | | |
| Rocker Control | Stationary, approximately (0°) | | |
| Stop Condition | Time (about 10 min) | | |

The values for step 2 shown in Table 9 may be used.

TABLE 9

Step 2 Settings for Condition Media

| Setting | Example Factory Default | Example Laboratory Default | Modifications |
|---|---|---|---|
| IC Inlet | None | | |
| IC Inlet Rate | 0 | | |
| IC Circulation Rate | about 100 mL/min | | |
| EC Inlet | EC Media | IC Media | |
| EC Inlet Rate | about 0.1 mL/min | | |
| EC Circulation Rate | about 30 mL/min | | |
| Outlet | EC Waste | | |
| Rocker Control | Stationary, approximately (0°) | | |
| Stop Condition | Manual | | |

Day: 0 Load Cells with Circulating Distribution

This part of the example protocol is performed to loads cells into the bioreactor from a cell inlet bag. IC circulation may be used to distribute the cells and may not attempt to chase the cells from the line into the bioreactor. This task may include three separate steps.
Step 1: loads the cells from the cell inlet bag into the bioreactor.
Step 2: chases the cells from the ARC to the bioreactor. Larger chase volumes spread the cells and move them towards the IC outlet.
Step 3: promotes distribution of cells across membrane via IC circulation and no IC inlet thus no ultrafiltration.

Before starting this task, the following preconditions may be satisfied:
Include a minimum of 40 mL of air in the cell inlet bag.

Table 10 describes the bags of solution attached to each line when performing Load Cells with Circulating Distribution. These solutions and corresponding volumes are provided as one example of default settings that may be used.

TABLE 10

Solutions for Load Cells With Circulating Distribution

| Line | Solution in Bag | Volume (estimation) |
|---|---|---|
| Cell Inlet | Cells | Cells in about 100 mL complete media |
| Reagent | None | N/A |
| IC Media | Media with Protein | about 0.1 L |
| Wash | None | N/A |
| EC Media | None | N/A |

The values for step 1 shown in Table 11 may be used.

TABLE 11

Step 1 Settings for Load Cells With Circulating Distribution

| Setting | Example Factory Default | Example Laboratory Default | Modifications |
|---|---|---|---|
| IC Inlet | None | | Cells |
| IC Inlet Rate | about 0 mL/min | | about 25 mL/min |
| IC Circulation Rate | about 0 mL/min. | | about 150 mL/min |
| EC Inlet | None | | |
| EC Inlet Rate | about 0 mL/min | | |

TABLE 11-continued

Step 1 Settings for Load Cells With Circulating Distribution

| Setting | Example Factory Default | Example Laboratory Default | Modifications |
|---|---|---|---|
| EC Circulation Rate | about 0 mL/min | | about 30 mL/min |
| Outlet | EC Waste | | |
| Rocker Control | Stationary, approximately | | In Motion, approximately (−90°, 180°, 1 sec) |
| Stop Condition | Manual | | Empty Bag |

The values for step 2 shown in Table 12 may be used.

TABLE 12

Step 2 Settings for Load Cells with Circulating Distribution

| Setting | Example Factory Default | Example Laboratory Default | Modifications |
|---|---|---|---|
| IC Inlet | None | | IC Media |
| IC Inlet Rate | about 0 mL/min | | about 25 mL/min |
| IC Circulation Rate | about 0 mL/min. | | about 150 mL/min |
| EC Inlet | None | | |
| EC Inlet Rate | about 0 mL/min | | |
| EC Circulation Rate | about 0 mL/min | | about 30 mL/min |
| Outlet | EC Waste | | |
| Rocker Control | Stationary, approximately | | In Motion, approximately (−90°, 180°, 1 sec) |
| Stop Condition | Manual | | IC Volume (about 47 mL) |

The values for step 3 shown in Table 13 may be used.

TABLE 13

Step 3 Settings for Load Cells with Circulating Distribution

| Setting | Factory Default | Laboratory Default | Modifications |
|---|---|---|---|
| IC Inlet | None | | |
| IC Inlet Rate | about 0 mL/min | | |
| IC Circulation Rate | about 0 mL/min. | | about 200 mL/min |
| EC Inlet | None | | |
| EC Inlet Rate | about 0 mL/min | | |
| EC Circulation Rate | about 0 mL/min | | about 30 mL/min |
| Outlet | EC Waste | | |
| Rocker Control | Stationary, approximately | | In Motion, approximately (−90°, 180°, 1 sec) |
| Stop Condition | Manual | | Time (about 2.0 min) |

Day: 0 Attach Cells

This part of the example protocol is performed to enable adherent cells to attach to the bioreactor membrane while allowing flow on the EC circulation loop. The pump flow rate to the IC loop is set to approximately zero.

Table 14 describes the bags of solution attached to each line when performing Attach Cells. These solutions and corresponding volumes are provided as one example of default settings that may be used.

TABLE 14

Solutions for Attach Cells

| Bag | Solution in Bag | Volume (estimation based on factory default values) |
|---|---|---|
| Cell Inlet | None | N/A |
| Reagent | None | N/A |
| IC Media | None | N/A |
| Wash | None | N/A |
| EC Media | None | N/A |
| Waste | Base Media | 500 mL |

The values for Attach Cells shown in Table 15 may be used.

TABLE 15

Task Settings for Attach Cells

| Setting | Example Factory Default | Example Laboratory Default | Modifications |
|---|---|---|---|
| IC Inlet | None | | |
| IC Inlet Rate | about 0 mL/min | | |
| IC Circulation Rate | about 0 mL/min | | |
| EC Inlet | EC Media | None | |
| EC Inlet Rate | about 0.1 mL/min | 0 | |
| EC Circulation Rate | about 30 mL/min | | |
| Outlet | EC Waste | | |
| Rocker Control | Stationary, approximately (0°) | | |
| Stop Condition | Manual | | |

Day: 1 Feed Cells

This part of the example protocol is performed to continuously add a low flow rate to the IC circulation loop and/or the EC circulation loop. There are several outlet settings that may used to remove the fluid added to the system.

Table 16 describes the bags of solution attached to each line when performing Feed Cells. These solutions and corresponding volumes are provided as one example of default settings that may be used.

TABLE 16

Solutions for Feed Cells

| Bag | Solution in Bag | Volume (estimation) |
|---|---|---|
| Cell Inlet | None | N/A |
| Reagent | None | N/A |
| IC Media | Media with Protein | about 6 mL/hour |
| Wash | None | N/A |
| EC Media | None | N/A |
| Waste | Base Media | about 500 mL |

The values for step 1 shown in Table 17 may be used.

TABLE 17

Task Settings for Feed Cells

| Setting | Example Factory Default | Example Laboratory Default | Modifications |
|---|---|---|---|
| IC Inlet | IC Media | | |
| IC Inlet Rate | about 0.1 mL/min | 0 mL/min | |
| IC Circulation Rate | about 20 mL/min | | |
| EC Inlet | None | | |
| EC Inlet Rate | about 0 mL/min | | |
| EC Circulation Rate | about 30 mL/min | | |
| Outlet | IC Waste | | |
| Rocker Control | Stationary, approximately (0°) | | |
| Stop Condition | Manual | | |

The IC Inlet rate may be increased as needed. As one example, the IC inlet rate may be increased as follows: Day 1-Day 2: 0.0 mL/min; Day 2-Day 3: 0.1 mL/min; Day 3-Day 4: 0.2 mL/min; Day 4-Day 5: 0.4 mL/min; and Day 5-Day 6: 0.8 mL/min.

Release Adherent Cells

This part of the example protocol is performed to release cells from the membrane, leaving the cells in the IC loop.
- Step 1: performs the IC/EC Washout task in preparation for adding a reagent. For example, the system replaces IC/EC media with PBS to remove protein, Ca++, and Mg++ in preparation for adding trypsin.
- Step 2: loads a reagent into the system until the bag is empty.
- Step 3: chases the reagent into the IC loop.
- Step 4: mixes the reagent within the IC loop.

Before starting this task, the following preconditions may be satisfied:

Include a minimum of 40 mL of air in the cell inlet bag.

Table 18 describes the bags of solution attached to each line when performing Release Adherent Cells. These solutions and corresponding volumes are provided as one example of default settings that may be used.

TABLE 18

Solutions for Release Adherent Cells

| Bag | Solution in Bag | Volume (estimation) |
|---|---|---|
| Cell Inlet | None | N/A |
| Reagent | Trypsin | about 180 mL |
| IC Media | None | N/A |
| Wash | PBS | about 1.4 L |
| EC Media | None | N/A |

The values for step 1 shown in Table 19 may be used.

TABLE 19

Step 1 Settings for Release Adherent Cells

| Setting | Example Factory Default | Example Laboratory Default | Modifications |
|---|---|---|---|
| IC Inlet | Wash | | |
| IC Inlet Rate | about 100 mL/min | | |
| IC Circulation Rate | about −17 mL/min | | |
| EC Inlet | Wash | | |
| EC Inlet Rate | about 148 mL/min | | |
| EC Circulation Rate | about −1.7 mL/min | | |
| Outlet | IC and EC Waste | | |
| Rocker Control | In Motion, approximately (−90°, 180°, 1 sec) | | |
| Stop Condition | Exchange (about 2.5 IC Volumes) (about 2.5 EC Volumes) | | |

The values for step 2 shown in Table 20 may be used.

TABLE 20

Step 2 Settings for Release Adherent Cells

| Setting | Example Factory Default | Example Laboratory Default | Modifications |
|---|---|---|---|
| IC Inlet | Reagent | | |
| IC Inlet Rate | about 50 mL/min | | |
| IC Circulation Rate | about 300 mL/min | | |
| EC Inlet | None | | |
| EC Inlet Rate | about 0 mL/min | | |
| EC Circulation Rate | about 30 mL/min | | |
| Outlet | EC Waste | | |
| Rocker Control | In Motion, approximately (−90°, 180°, 1 sec) | | |
| Stop Condition | Empty Bag | | |

The values for step 3 shown in Table 21 may be used.

TABLE 21

Step 3 Settings for Release Adherent Cells

| Setting | Example Factory Default | Example Laboratory Default | Modifications |
|---|---|---|---|
| IC Inlet | Wash | | |
| IC Inlet Rate | about 50 mL/min | | |
| IC Circulation Rate | about 300 mL/min | | |
| EC Inlet | None | | |
| EC Inlet Rate | about 0 mL/min | | |
| EC Circulation Rate | about 30 mL/min | | |
| Outlet | EC Waste | | |
| Rocker Control | In Motion, approximately (−90°, 180°, 1 sec) | | |
| Stop Condition | IC Volume (22 mL) | | |

The values for step 4 shown in Table 22 may be used.

TABLE 22

Step 4 Settings for Release Adherent Cells

| Setting | Example Factory Default | Example Laboratory Default | Modifications |
|---|---|---|---|
| IC Inlet | None | | |
| IC Inlet Rate | about 0 mL/min | | |
| IC Circulation Rate | about 300 mL/min | | |
| EC Inlet | None | | |

TABLE 22-continued

Step 4 Settings for Release Adherent Cells

| Setting | Example Factory Default | Example Laboratory Default | Modifications |
|---|---|---|---|
| EC Inlet Rate | about 0 mL/min | | |
| EC Circulation Rate | about 30 mL/min | | |
| Outlet | EC Waste | | |
| Rocker Control | In Motion, approximately (−90°, 180°, 1 sec) | | |
| Stop Condition | Time (about 4 min) | | |

Samples may be taken from a sample coil and/or a sample port for a trypsin assay.

Harvest Cells

This part of the example protocol is performed to transfer cells in suspension from the IC circulation loop, including cells in the bioreactor, to the harvest bag.

Table 23 describes the bags of solution attached to each line when performing Harvest Cells. These solutions and corresponding volumes are provided as one example of default settings that may be used.

TABLE 23

Solutions for Harvest Cells

| Bag | Solution in Bag | Volume (estimation) |
|---|---|---|
| Cell Inlet | None | N/A |
| Reagent | None | N/A |
| IC Media | Harvest Media | about 0.6 L |
| Wash | None | N/A |
| EC Media | None | N/A |

The values for Harvest Cells shown in Table 24 may be used.

TABLE 24

Task Settings for Harvest Cells

| Setting | Example Factory Default | Example Laboratory Default | Modifications |
|---|---|---|---|
| IC Inlet | IC Media | | |
| IC Inlet Rate | about 400 mL/min | | |
| IC Circulation Rate | about −69 mL/min | | |
| EC Inlet | EC Media | IC Media | |
| EC Inlet Rate | about 60 mL/min | | |
| EC Circulation Rate | about 30 mL/min | | |
| Outlet | Harvest | | |
| Rocker Control | In Motion, approximately (−90°, 180°, 1 sec) | | |
| Stop Condition | IC Volume (about 378 mL) | | |

Example 2: Protocol 2

Cholecystokinin (CCK) is a regulatory hormone secreted by cells and, in many cases, may in part be responsible for cell culture maintenance and proliferation via chemical signaling. If CCK concentration in the culture media does not reach a threshold, the cell population can be compromised. Example 2 provides an example of a cell-secreted chemical signal used to maintain and proliferate a population of cells in vitro; in this case, CHO cells. According to an embodiment, the molecular weight of CCK of approximately 4,000 Daltons makes it small enough to readily pass through the microporous membrane of a hollow-fiber bioreactor. In an embodiment, regardless of inlet media addition to the IC circulation loop or EC circulation loop, dilution of the chemical signal may occur due to the freedom to pass through the membrane. However, through the passive replacement of media, according to embodiments, such dilution of chemical signaling can be minimized or eliminated altogether. The following protocol provides for the passive replacement of media during the cell expansion of non-adherent or suspension cells, such as CHO cells, for example, according to embodiments.

Day: 0 IC EC Washout

This part of the example protocol is performed to replace the fluid on both the IC circulation loop and the EC circulation loop in preparation for cell culturing. The replacement volume may be specified by the number of IC Volumes and EC Volumes exchanged.

Table 25 describes the bags of solution that are attached to each line when performing IC EC Washout of this example protocol. These solutions and corresponding volumes are provided as one example of default settings that may be used.

TABLE 25

Solutions for IC EC Washout

| Bag | Solution in Bag | Volume (estimation) |
|---|---|---|
| Cell Inlet | None | N/A |
| Reagent | None | N/A |
| IC Media | Media without Protein | about 1.4 L |
| Wash | None | N/A |
| EC Media | None | N/A |

The values for IC EC Washout shown in Table 26 may be used.

TABLE 26

Task Settings for IC EC Washout

| Setting | Example Factory Default | Example Laboratory Default | Modifications |
|---|---|---|---|
| IC Inlet | IC Media | | |
| IC Inlet Rate | about 100 mL/min | | |
| IC Circulation Rate | about −17 mL/min | | |
| EC Inlet | EC Media | IC Media | |
| EC Inlet Rate | about 148 mL/min | | |
| EC Circulation Rate | about −1.7 mL/min | | |
| Outlet | IC and EC Waste | | |
| Rocker Control | In Motion approximately (−90°, 180°, 1 sec) | | |
| Stop Condition | Exchange (about 2.5 IC Volumes) (about 2.5 EC Volumes) | | |

Day: 0 Condition Media

This part of the example protocol is performed to allow the media to reach equilibrium with the provided gas supply before loading the cells. This task may include two separate steps:
   Step 1: provides rapid contact between the media and the gas supply by using a high EC circulation rate.
   Step 2: maintains the system in a proper state until the operator is ready to load the cells.

Table 27 describes the bags of solution that are attached to each line when performing Condition Media. These solutions and corresponding volumes are provided as one example of default settings that may be used.

TABLE 27

Solutions for Condition Media

| Line | Solution in Bag | Volume (estimation) |
|---|---|---|
| Cell Inlet | None | N/A |
| Reagent | None | N/A |
| IC Media | Media without Protein | about 0.1 L plus 6 mL/hour |
| Wash | None | N/A |
| EC Media | None | N/A |

The values for step 1 shown in Table 28 may be used.

TABLE 28

Step 1 Settings for Condition Media

| Setting | Example Factory Default | Example Laboratory Default | Modifications |
|---|---|---|---|
| IC Inlet | None | | |
| IC Inlet Rate | about 0 mL/min | | |
| IC Circulation Rate | about 100 mL/min | | |
| EC Inlet | EC Media | IC Media | |
| EC Inlet Rate | about 0.1 mL/min | | |
| EC Circulation Rate | about 250 mL/min | | |
| Outlet | EC Waste | | |
| Rocker Control | Stationary, approximately (0°) | | |
| Stop Condition | Time (about 10 min) | | |

The values for step 2 shown in Table 29 may be used.

TABLE 29

Step 2 Settings for Condition Media

| Setting | Example Factory Default | Example Laboratory Default | Modifications |
|---|---|---|---|
| IC Inlet | None | | |
| IC Inlet Rate | 0 | | |
| IC Circulation Rate | about 100 mL/min | | |
| EC Inlet | EC Media | IC Media | |
| EC Inlet Rate | about 0.1 mL/min | | |
| EC Circulation Rate | about 30 mL/min | | |
| Outlet | EC Waste | | |
| Rocker Control | Stationary, approximately (0°) | | |
| Stop Condition | Manual | | |

Day: 0 Load Cells with Uniform Suspension

This part of the example protocol is performed to load cells into the bioreactor from a cell inlet bag. For example, in an embodiment, such cells comprise CHO cells. IC circulation may be used to distribute the cells and may not attempt to chase the cells from the line into the bioreactor. This task may include three separate steps.
   Step 1: loads the cells from the cell inlet bag into the bioreactor.
   Step 2: chases the cells from the ARC to the IC Loop.
   Step 3: promotes distribution of cells across membrane via IC circulation and no IC inlet, thus no ultrafiltration.

Before starting this task, the following preconditions may be satisfied:
   Include a minimum of 40 mL of air in the cell inlet bag.

Table 30 describes the bags of solution attached to each line when performing Load Cells with Uniform Suspension. These solutions and corresponding volumes are provided as one example of default settings that may be used.

TABLE 30

Solutions for Load Cells with Uniform Suspension

| Line | Solution in Bag | Volume (estimation) |
|---|---|---|
| Cell Inlet | Cells | 9.45E+07 Cells in about 100 mL media |
| Reagent | None | N/A |
| IC Media | Media without Protein | about 0.1 L |
| Wash | None | N/A |
| EC Media | None | N/A |

The values for step 1 shown in Table 31 may be used.

TABLE 31

Step 1 Settings for Load Cells with Uniform Suspension

| Setting | Example Factory Default | Example Laboratory Default | Modifications |
|---|---|---|---|
| IC Inlet | Cell Inlet | | |
| IC Inlet Rate | about 50 mL/min | | |
| IC Circulation Rate | about 200 mL/min. | | |
| EC Inlet | None | | |
| EC Inlet Rate | about 0 mL/min | | |
| EC Circulation Rate | about 30 mL/min | | |
| Outlet | EC Outlet | | |
| Rocker Control | In Motion, approximately (−90°, 180°, 1 sec) | | |
| Stop Condition | Empty Bag | | |

The values for step 2 shown in Table 32 may be used.

TABLE 32

Step 2 Settings for Load Cells with Uniform Suspension

| Setting | Example Factory Default | Example Laboratory Default | Modifications |
|---|---|---|---|
| IC Inlet | IC Media | | |
| IC Inlet Rate | about 50 mL/min | | |
| IC Circulation Rate | about 200 mL/min | | |
| EC Inlet | None | | |
| EC Inlet Rate | about 0 mL/min | | |
| EC Circulation Rate | about 30 mL/min | | |
| Outlet | EC Outlet | | |
| Rocker Control | In Motion (−90°, 180°, 1 sec) | | |
| Stop Condition | IC Volume (about 22 mL) | | |

The values for step 3 shown in Table 33 may be used.

TABLE 33

Step 3 Settings for Load Cells with Uniform Suspension

| Setting | Factory Default | Laboratory Default | Modifications |
|---|---|---|---|
| IC Inlet | None | | |
| IC Inlet Rate | about 0 mL/min | | |
| IC Circulation Rate | about 200 mL/min | | |
| EC Inlet | None | | |
| EC Inlet Rate | about 0 mL/min | | |
| EC Circulation Rate | about 30 mL/min | | |
| Outlet | EC Outlet | | |
| Rocker Control | In Motion (−90°, 180°, 1 sec) | | |
| Stop Condition | Time (about 2.0 min) | | |

Day: 0 Feed Cells

This part of the example protocol is performed to allow chemical signals, such as CCK, to increase in concentration by turning the inlet media flow rate "OFF" to the IC circulation loop and the EC circulation loop. IC or EC Outlet can be used in this configuration.

Table 34 describes the bags of solution attached to each line when performing Feed Cells. These solutions and corresponding volumes are provided as one example of default settings that may be used.

TABLE 34

Solutions for Feed Cells

| Bag | Solution in Bag | Volume (estimation) |
|---|---|---|
| Cell Inlet | None | N/A |
| Reagent | None | N/A |
| IC Media | None | N/A |
| Wash | None | N/A |
| EC Media | None | N/A |
| Outlet | Media without Protein | 0.2 L |

The values for step 1 shown in Table 35 may be used.

TABLE 35

Task Settings for Feed Cells

| Setting | Example Factory Default | Example Laboratory Default | Modifications |
|---|---|---|---|
| IC Inlet | IC Media | | None |
| IC Inlet Rate | about 0.1 mL/min | | about 0 mL/min |
| IC Circulation Rate | about 20 mL/min | | about 50 mL/min |
| EC Inlet | None | | |
| EC Inlet Rate | about 0 mL/min | | |
| EC Circulation Rate | about 30 mL/min | | |
| Outlet | IC Outlet | | EC Outlet |
| Rocker Control | Stationary, approximately (0°) | | In Motion (0°, 180°, about 60 sec) |
| Stop Condition | Manual | | |

In an embodiment, each day, the cell culture is sampled for cell counts using the following settings:

TABLE 36

Task Settings for Counting Cells

| Setting | Example Factory Default | Example Laboratory Default | Modifications |
|---|---|---|---|
| IC Inlet | None | | |
| IC Inlet Rate | about 0 mL/min | | |
| IC Circulation Rate | about 200 mL/min | | |
| EC Inlet | None | | |
| EC Inlet Rate | about 0 mL/min | | |
| EC Circulation Rate | about 30 mL/min | | |
| Outlet | IC Outlet | | EC Outlet |
| Rocker Control | In Motion (0°, 180°, 1 sec) | | |
| Stop Condition | Time (about 5.0 min) | | |

In an embodiment, immediately following the stop condition, a length of tubing of about six (6) inches long (1 mL) is excised. The volume in this sample provides a representative cell concentration sample of the entire IC loop. This allows the user(s) to monitor the cells throughout the duration of culturing.

Day: 4 Feed Cells

This part of the example protocol is performed to continuously add a low flow rate to the IC circulation loop and/or the EC circulation loop once the cell culture conditions have reached a minimum tolerance glucose concentration or maximum tolerance lactate concentration. This may occur earlier or later than day 4, in embodiments. There are several outlet settings that may used to remove the fluid added to the system.

Table 37 describes the bags of solution attached to each line when performing Feed Cells. These solutions and corresponding volumes are provided as one example of default settings that may be used.

TABLE 37

Solutions for Feed Cells

| Bag | Solution in Bag | Volume (estimation) |
|---|---|---|
| Cell Inlet | None | N/A |
| Reagent | None | N/A |
| IC Media | Media without Protein | about 6 mL/hour |
| Wash | None | N/A |
| EC Media | None | N/A |

The values for step 1 shown in Table 38 may be used.

TABLE 38

Task Settings for Feed Cells

| Setting | Example Factory Default | Example Laboratory Default | Modifications |
|---|---|---|---|
| IC Inlet | IC Media | | |
| IC Inlet Rate | about 0.1 mL/min | | |
| IC Circulation Rate | about 20 mL/min | | about 50 mL/min |
| EC Inlet | None | | |
| EC Inlet Rate | about 0 mL/min | | |

TABLE 38-continued

Task Settings for Feed Cells

| Setting | Example Factory Default | Example Laboratory Default | Modifications |
|---|---|---|---|
| EC Circulation Rate | about 30 mL/min | | |
| Outlet | IC Outlet | | EC Outlet |
| Rocker Control | Stationary, approximately (0°) | | In Motion (0°, 180°, about 60 sec) |
| Stop Condition | Manual | | |

In an embodiment, each day, the cell culture is sampled for cell counts (see Table 36, for example).

Day: 7 Harvest Cells

This part of the example protocol is performed to transfer cells in suspension from the IC circulation loop, including cells in the bioreactor, to the harvest bag.

Table 39 describes the bags of solution attached to each line when performing Harvest Cells. These solutions and corresponding volumes are provided as one example of default settings that may be used.

TABLE 39

Solutions for Harvest Cells

| Bag | Solution in Bag | Volume (estimation) |
|---|---|---|
| Cell Inlet | None | N/A |
| Reagent | None | N/A |
| IC Media | Harvest Media | about 0.6 L |
| Wash | None | N/A |
| EC Media | None | N/A |

The values for Harvest Cells shown in Table 40 may be used.

TABLE 40

Task Settings for Harvest Cells

| Setting | Example Factory Default | Example Laboratory Default | Modifications |
|---|---|---|---|
| IC Inlet | IC Media | | |
| IC Inlet Rate | about 400 mL/min | | |
| IC Circulation Rate | about −69 mL/min | | |
| EC Inlet | EC Media | IC Media | |
| EC Inlet Rate | about 60 mL/min | | |
| EC Circulation Rate | about 30 mL/min | | |
| Outlet | Harvest | | |
| Rocker Control | In Motion, approximately (−90°, 180°, 1 sec) | | |
| Stop Condition | IC Volume (about 378 mL) | | |

It will be apparent to those skilled in the art that various modifications and variations may be made to the apparatus, systems, structure, and methods described herein. Thus, it should be understood that the embodiments are not limited to the subject matter discussed in the present disclosure. Rather, the present disclosure is intended to cover modifications, variations, and/or equivalents. The acts, features, structures, and/or media are disclosed as illustrative embodiments for implementation of the claims.

What is claimed is:

1. A cell expansion system, comprising:
a bioreactor comprising a first fluid flow path having at least opposing ends, a first opposing end of the first fluid flow path fluidly associated with a first port of a hollow fiber membrane and a second end of the first fluid flow path fluidly associated with a second port of the hollow fiber membrane, wherein the first fluid flow path comprises an intracapillary portion of the hollow fiber membrane;
a fluid inlet path fluidly associated with the first fluid flow path, wherein a plurality of cells are introduced into the first fluid flow path through the first fluid inlet path;
a first pump that circulates fluid in the first fluid flow path of the bioreactor;
an outlet line in fluid communication with the bioreactor, wherein the outlet line is attached, at a first time, to an outlet bag in the cell expansion system; and
a controller that controls operation of the first pump, wherein the controller is configured to control the first pump to:
circulate a fluid at a first rate within the first fluid flow path; and
stop, when the outlet bag is replaced with a media bag at a second time, the circulation of the fluid within the first fluid flow path after the plurality of the cells are loaded into the bioreactor, wherein the outlet line is attached to the media bag at the second time; and
wherein media from the media bag is added to the bioreactor while the circulation of the fluid within the first fluid flow path is stopped.

2. The cell expansion system of claim 1, wherein the media bag comprises base media.

3. The cell expansion system of claim 1, wherein the cell expansion system is closed.

4. The cell expansion system of claim 1, wherein the plurality of cells comprises adherent cells.

5. The cell expansion system of claim 1, wherein the plurality of cells comprises non-adherent cells.

6. The cell expansion system of claim 1, further comprising:
a second pump that transfers intracapillary inlet fluid from an intracapillary media bag to the first fluid flow path;
a second controller that controls operation of the second pump, wherein the second controller is configured to control the second pump to:
transfer the plurality of cells from a cell inlet bag to the first fluid flow path; and
stop, at the second time, the transfer of the plurality of cells from the cell inlet bag after the plurality of the cells are loaded into the bioreactor.

7. The cell expansion system of claim 1, wherein the bioreactor further comprises:
a second fluid flow path comprising an extracapillary portion of the hollow fiber membrane, wherein the outlet line is in fluid communication with the bioreactor via the second fluid flow path.

8. The cell expansion system of claim 7, wherein the media from the media bag is added to the bioreactor by pumping the media through the second fluid flow path.

9. The cell expansion system of claim 8, further comprising:
an extracapillary pump that pumps the media from the media bag along the outlet line and through the second fluid flow path.

10. A cell expansion system, comprising:
a bioreactor comprising:
- a first fluid flow path having at least opposing ends, a first opposing end of the first fluid flow path fluidly associated with a first port of a hollow fiber membrane and a second end of the first fluid flow path fluidly associated with a second port of the hollow fiber membrane, wherein the first fluid flow path comprises an intracapillary portion of the hollow fiber membrane; and
- a second fluid flow path comprising an extracapillary portion of the hollow fiber membrane;

a fluid inlet path fluidly associated with the first fluid flow path, wherein a plurality of cells are introduced into the first fluid flow path through the fluid inlet path;
a first pump that circulates fluid in the first fluid flow path of the bioreactor;
a second pump that circulates fluid in the second fluid flow path of the bioreactor;
an outlet line in fluid communication with the bioreactor via the second fluid flow path wherein the outlet line comprises an attachment to one of an outlet bag or a media bag;
a processor coupled with the first pump; and
a memory coupled with and readable by the processor and storing therein instructions that, when executed by the processor, cause the processor to:
- circulate, via operating the first pump, a fluid at a first rate within the first fluid flow path while the outlet line is attached to the outlet bag;
- stop, via turning off the first pump, the circulation of the fluid within the first fluid flow path after the plurality of the cells are loaded into the bioreactor and when the outlet line is attached to the media bag instead of the outlet bag; and
- add, via operating the second pump while the first pump is turned off, media from the media bag to the bioreactor when the outlet line is attached to the media bag instead of the outlet bag.

11. The cell expansion system of claim 10, wherein the media bag comprises base media, and wherein the cell expansion system is closed.

12. The cell expansion system of claim 10, wherein at least one of the first pump and the second pump are peristaltic pumps.

13. The cell expansion system of claim 10, wherein an amount of the media from the media bag added to the bioreactor replaces an amount of fluid evaporated from the bioreactor.

14. The cell expansion system of claim 10, further comprising:
a valve fluidly interconnected to the outlet line, wherein the valve selectively controls a flow of the media from the media bag.

15. The cell expansion system of claim 14, wherein, prior to adding the media from the media bag to the bioreactor, the instructions further cause the processor to maintain the valve in an open state.

16. The cell expansion system of claim 10, further comprising:
an intracapillary media bag comprising intracapillary inlet fluid;
a cell inlet bag comprising the plurality of cells; and
a third pump that transfers the intracapillary inlet fluid from the intracapillary media bag to the first fluid flow path.

17. The cell expansion system of claim 16, wherein the instructions further cause the processor to:
transfer, via operating the third pump, the plurality of cells from the cell inlet bag and the intracapillary inlet fluid from the intracapillary media bag to the first fluid flow path; and
stop, via turning off the first pump, the transfer of the plurality of cells from the cell inlet bag after the plurality of the cells are loaded into the bioreactor.

18. A cell expansion method, comprising:
loading a disposable tubing set onto a cell expansion system, the disposable tubing set comprising:
- a bioreactor comprising a first fluid flow path having at least opposing ends, a first opposing end of the first fluid flow path fluidly associated with a first port of a hollow fiber membrane and a second end of the first fluid flow path fluidly associated with a second port of the hollow fiber membrane, wherein the first fluid flow path comprises an intracapillary portion of the hollow fiber membrane;
- a fluid inlet path fluidly associated with the first fluid flow path; and
- an outlet bag; and
- an outlet line attached to the outlet bag and in fluid communication with the bioreactor;

pumping, by a first pump of the cell expansion system, a plurality of cells into the first fluid flow path through the fluid inlet path;
circulating, by the first pump, a fluid at a first rate within the first fluid flow path;
stopping, by a processor when the outlet bag is replaced with a media bag at a second time, the circulation of the fluid within the first fluid flow path after the plurality of the cells are loaded into the bioreactor, wherein the outlet line is attached to the media bag at the second time; and
pumping, by a second pump of the cell expansion system, media from the media bag through the outlet line to the bioreactor while the circulation of the fluid within the first fluid flow path is stopped.

19. The method of claim 18, wherein stopping the circulation of the fluid within the first fluid flow path after the plurality of the cells are loaded into the bioreactor comprises:
deactivating, by the processor, the first pump causing the first pump to turn off.

20. The method of claim 18, wherein pumping the plurality of cells into the first fluid flow path through the fluid inlet path further comprises:
pumping, via a third pump of the cell expansion system, the plurality of cells from a cell inlet bag and intracapillary inlet fluid from an intracapillary media bag to the first fluid flow path.

* * * * *